United States Patent
Cho et al.

(10) Patent No.: US 11,141,135 B2
(45) Date of Patent: Oct. 12, 2021

(54) ULTRASOUND APPARATUS AND METHOD OF DISPLAYING ULTRASOUND IMAGES

(71) Applicant: SAMSUNG ELECTRONICS CO., LTD., Suwon-si (KR)

(72) Inventors: Eun-jin Cho, Seoul (KR); Eun-ho Yang, Hongcheon-gun (KR); Su-jin Kim, Yongin-si (KR); Woong Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1242 days.

(21) Appl. No.: 15/049,227

(22) Filed: Feb. 22, 2016

(65) Prior Publication Data
US 2016/0345936 A1     Dec. 1, 2016

(30) Foreign Application Priority Data
May 29, 2015   (KR) .................. 10-2015-0076617

(51) Int. Cl.
*A61B 8/00* (2006.01)
*G01S 7/52* (2006.01)
*A61B 8/08* (2006.01)

(52) U.S. Cl.
CPC ............ *A61B 8/463* (2013.01); *A61B 8/0866* (2013.01); *A61B 8/461* (2013.01); *A61B 8/469* (2013.01); *G01S 7/52033* (2013.01); *G01S 7/52063* (2013.01); *G01S 7/52068* (2013.01); *G01S 7/52074* (2013.01); *G01S 7/52082* (2013.01);
(Continued)

(58) Field of Classification Search
CPC ........ A61B 2503/40; A61B 2560/0475; A61B 2560/0487; A61B 8/0866; A61B 8/4405; A61B 8/461; A61B 8/463; A61B 8/465; A61B 8/467; A61B 8/469; A61B 8/5207; A61B 8/5269
See application file for complete search history.

(56) References Cited

U.S. PATENT DOCUMENTS

| 5,482,045 A | 1/1996 | Rust et al. |
| 5,997,478 A | 12/1999 | Jackson et al. |

(Continued)

FOREIGN PATENT DOCUMENTS

| CN | 103202712 A | 7/2013 |
| CN | 103300887 A | 9/2013 |

(Continued)

OTHER PUBLICATIONS

Communication dated Oct. 31, 2016 issued by the European Patent Office in counterpart European Patent Application No. 16171337.5.
(Continued)

*Primary Examiner* — Christopher L Cook
(74) *Attorney, Agent, or Firm* — Sughrue Mion, PLLC

(57) ABSTRACT

A method of displaying an ultrasound image includes reading, based on a user's input, the ultrasound image stored in a storage medium; displaying, on a screen, the ultrasound image and TGC information that is matched to the ultrasound image; receiving an input of modifying the TGC information by adjusting a TGC value in the TGC information, the at least one TGC value corresponding to a depth value; and updating the ultrasound image based on the modified TGC information.

30 Claims, 37 Drawing Sheets

(52) U.S. Cl.
CPC ......... *G01S 7/52084* (2013.01); *A61B 8/4405* (2013.01); *A61B 8/465* (2013.01); *A61B 8/467* (2013.01); *A61B 8/5207* (2013.01); *A61B 8/5269* (2013.01); *A61B 2503/40* (2013.01); *A61B 2560/0475* (2013.01); *A61B 2560/0487* (2013.01)

(56) References Cited

U.S. PATENT DOCUMENTS

| | | |
|---|---|---|
| 6,468,212 B1 | 10/2002 | Scott et al. |
| 6,511,426 B1 | 1/2003 | Hossack et al. |
| 6,951,543 B2 | 10/2005 | Roundhill |
| 10,595,827 B2 | 3/2020 | Yang et al. |
| 2003/0163045 A1* | 8/2003 | Gatzke ................ A61B 8/565 600/437 |
| 2004/0267124 A1* | 12/2004 | Roundhill ............ A61B 8/465 600/443 |
| 2006/0030775 A1 | 2/2006 | Adams et al. |
| 2007/0161898 A1 | 7/2007 | Hao et al. |
| 2008/0021834 A1* | 1/2008 | Holla ................ G06F 21/602 705/51 |
| 2010/0217126 A1 | 8/2010 | Yawata et al. |
| 2013/0184587 A1 | 7/2013 | Eom et al. |
| 2014/0031694 A1* | 1/2014 | Solek ................ A61B 8/461 600/459 |
| 2014/0088428 A1 | 3/2014 | Yang et al. |
| 2014/0143690 A1 | 5/2014 | Roncalez et al. |
| 2014/0164965 A1 | 6/2014 | Lee et al. |
| 2015/0035959 A1* | 2/2015 | Amble ................ G16H 30/40 348/74 |
| 2015/0265250 A1* | 9/2015 | Madore ................ A61B 8/5269 600/440 |
| 2015/0359516 A1 | 12/2015 | Yang et al. |
| 2016/0231900 A1* | 8/2016 | Meaney ................ G06F 16/954 |

FOREIGN PATENT DOCUMENTS

| | | |
|---|---|---|
| CN | 103654860 A | 3/2014 |
| EP | 2710960 A1 | 3/2014 |
| EP | 2927707 A1 | 10/2015 |
| KR | 10-2014-0039954 A | 4/2014 |
| KR | 10-2014-0090283 A | 7/2014 |
| WO | 2016/068604 A1 | 5/2016 |

OTHER PUBLICATIONS

Communication dated May 9, 2016, issued by the International Searching Authority in counterpart International Application No. PCT/KR2016/001384.

Communication dated Jan. 19, 2020 issued by the State Intellectual Property Office of P.R. China in counterpart Chinese Application No. 201680030937.0.

Communication dated Jul. 30, 2020 issued by the State Intellectual Property Office of P.R. China in counterpart Chinese Application No. 201680030937.0.

* cited by examiner

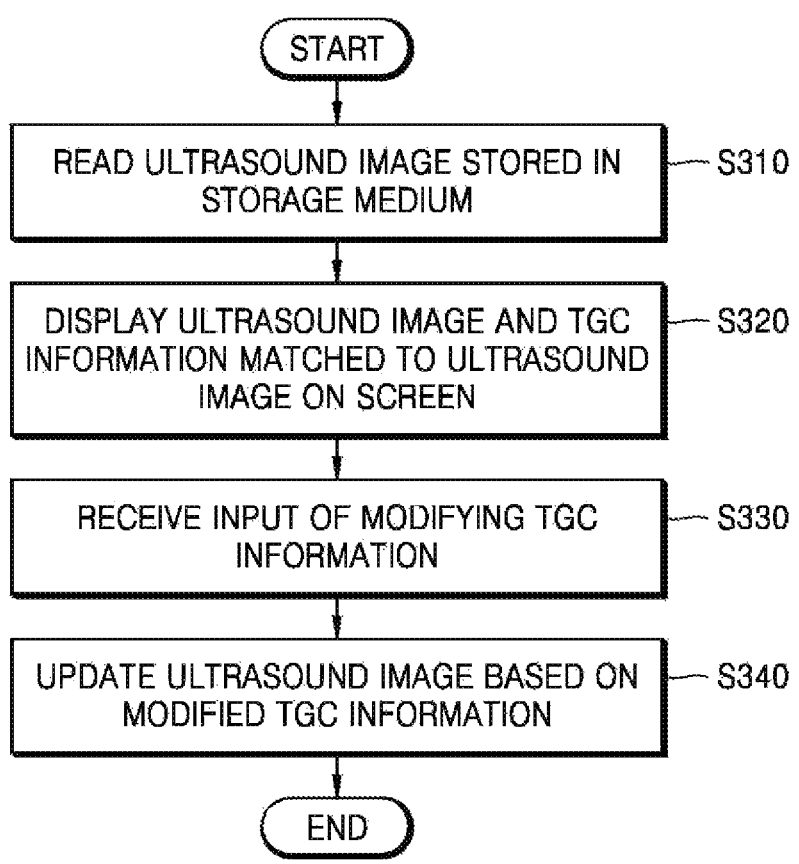

<STORED IMAGE>

<FIRST ULTRASOUND IMAGE FRAME>

<SECOND ULTRASOUND IMAGE FRAME>

ULTRASOUND APPARATUS AND METHOD OF DISPLAYING ULTRASOUND IMAGES

CROSS-REFERENCE TO RELATED APPLICATION

This application claims priority from Korean Patent Application No. 10-2015-0076617, filed on May 29, 2015, in the Korean Intellectual Property Office, the disclosure of which is incorporated herein in its entirety by reference.

BACKGROUND

1. Field

Apparatuses and methods consistent with exemplary embodiments relate to adjusting parameters related to ultrasound echo signal data and displaying ultrasound images.

2. Description of the Related Art

Ultrasound diagnostic apparatuses transmit ultrasound signals from a surface of a body of an object towards a part in the body and receive echo signals reflected from the object, thereby obtaining images of an internal part of the object (e.g., soft tissues or blood flow).

The ultrasound diagnostic apparatuses are small, cost-efficient, and capable of real-time displaying of images. Also, the ultrasound diagnostic apparatuses provide a high level of stability because there is no radioactive exposure. Therefore, the ultrasound diagnostic apparatuses are widely used.

In ultrasound, an amplitude and intensity of ultrasound beams that penetrate through the tissues decrease as a transmission distance increases. Attenuation is a phenomenon in which the amplitude decreases by a greater degree as the ultrasound beams penetrate through a longer distance. Due to the attenuation, intensity of received ultrasound echo signals may be irregular. That is, ultrasound images based on the ultrasound echo signals might not have uniform brightness or some ultrasound images may be of bad quality. Therefore, there is a need for apparatuses and methods to allow a user to easily compensate for sensitivity of ultrasound images.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide an ultrasound apparatus that reads ultrasound images from a storage medium, adjusts parameters related to ultrasound echo signal data of the read ultrasound images, and compensates for sensitivity of stored ultrasound images, and a method of displaying the ultrasound images.

According to an aspect of an exemplary embodiment, a method of displaying an ultrasound image includes reading, based on a user's input, the ultrasound image stored in a storage medium; displaying, on a screen, the ultrasound image and time gain compensation (TGC) information that is matched to the ultrasound image; receiving an input of modifying the TGC information by adjusting at least one TGC value in the TGC information, the at least one TGC value corresponds to at least one depth value; and updating the ultrasound image based on the modified TGC information.

In an exemplary embodiment, the storage medium includes an external storage medium provided outside an ultrasound apparatus.

In an exemplary embodiment, the reading of the ultrasound image includes reading the TGC information that is matched to the ultrasound image and stored in the storage medium.

In an exemplary embodiment, the reading of the ultrasound image includes displaying a list of a plurality of ultrasound images stored in the storage medium; and receiving an input of selecting the ultrasound image from the list of the plurality of ultrasound images.

In an exemplary embodiment, the reading of the ultrasound image includes receiving the ultrasound image, stored in an external device, from the external device.

In an exemplary embodiment, the displaying of the TGC information includes displaying, on an area of the screen, a TGC line that indicates a first TGC value set included in the TGC information, and the receiving of the input of modifying the TGC information includes receiving an input of modifying the first TGC value set to a second TGC value set via the TGC line.

In an exemplary embodiment, the receiving of the input of modifying the first TGC value set to the second TGC value set includes, when a plurality of slider bars are displayed in the area of the screen, receiving an input of moving at least one adjustment button among adjustment buttons located at an intersection of the TGC line and the slider bars.

In an exemplary embodiment, the receiving of the input of modifying the first TGC value set to the second TGC value set includes displaying a list of a plurality of TGC preset values sets; and receiving an input of selecting the second TGC value set from the list.

In an exemplary embodiment, the displaying of the list includes displaying text that indicates the plurality of TGC preset value sets.

In an exemplary embodiment, the method of displaying the list includes displaying TGC line images that respectively represent the plurality of TGC preset value sets.

In an exemplary embodiment, the updating of the ultrasound image includes applying the at least one adjusted TGC value to ultrasound echo signal data of the ultrasound image.

In an exemplary embodiment, the updating of the ultrasound image includes selecting a second ultrasound image frame that corresponds to the second TGC value set among a plurality ultrasound image frames that respectively correspond to a plurality of TGC value sets; and displaying the second ultrasound image instead of a first ultrasound image frame that corresponds to the first TGC value set.

In an exemplary embodiment, the method further includes matching the updated ultrasound image to the modified TGC information and storing the updated ultrasound image.

According to an aspect of an exemplary embodiment, an ultrasound apparatus includes a touch screen configured to display an ultrasound image read from a storage medium and TGC information that is matched to the ultrasound image, and receive an input of modifying the TGC information by adjusting at least one TGC value in the TGC information, the at least one TGC value corresponds to at least one depth value; and a controller configured to control the touch screen such that the ultrasound image is updated based on the modified TGC information.

In an exemplary embodiment, the controller is further configured to read, from the storage medium, the ultrasound image and the TGC information that is matched to the ultrasound image and stored in the storage medium.

In an exemplary embodiment, the ultrasound apparatus further includes a communication interface configured to receive the ultrasound image, stored in an external device, from the external device.

In an exemplary embodiment, the touch screen is further configured to display, on an area of the touch screen, a TGC line that indicates a first TGC value set included in the TGC information, and receive an input of modifying the first TGC value set to a second TGC value set via the TGC line.

In an exemplary embodiment, the touch screen is further configured to display a list of a plurality of TGC preset values sets, and receive an input of selecting the second TGC value set from the list.

In an exemplary embodiment, in order to display the list of the plurality of TGC preset value sets, the touch screen is further configured to display text or TGC line images that represent the plurality of TGC preset value sets.

In an exemplary embodiment, the controller is further configured to update the ultrasound image by applying the at least one adjusted TGC value to ultrasound echo signal data of the ultrasound image.

In an exemplary embodiment, the controller is further configured to update the ultrasound image by selecting a second ultrasound image frame that corresponds to the second TGC value set among a plurality ultrasound image frames that respectively correspond to a plurality of TGC value sets, and displaying, on the touch screen, the second ultrasound image instead of a first ultrasound image frame that corresponds to the first TGC value set.

In an exemplary embodiment, the controller is further configured to match the updated ultrasound image to the modified TGC information and store the updated ultrasound image.

According to an aspect of an exemplary embodiment, a method of displaying an ultrasound image includes reading an ultrasound image that is matched to a first TGC value set from a storage medium; displaying, on a first area of a screen, the ultrasound image matched to a first TGC value set; displaying, on a second area of the screen, a gain setting window for adjusting TGC values that correspond to a plurality of depth values of the ultrasound image; receiving a second TGC value set via the gain setting window; and updating the ultrasound image matched to a first TGC value set, based on the second TGC value set.

In an exemplary embodiment, the displaying of the gain setting window includes displaying a plurality of slider bars respectively corresponding to a plurality of depth values; and initializing locations of buttons on the plurality of slider bars.

In an exemplary embodiment, the receiving of the second TGC value set via the gain setting window includes receiving an input of adjusting the locations of the buttons on the plurality of slider bars to corresponding locations in the second TGC value set.

In an exemplary embodiment, the receiving of the second TGC value set via the gain setting window includes displaying a list of a plurality of TGC preset value sets; and receiving an input of selecting the second TGC value set from the list.

In an exemplary embodiment, the updating of the ultrasound image includes applying second TGC values in the second TGC value set to ultrasound echo signal data of the ultrasound image.

In an exemplary embodiment, the method further includes matching the updated ultrasound image to the second TGC value set and storing the updated ultrasound image.

According to an aspect of an exemplary embodiment, an ultrasound apparatus includes a touch screen configured to display, on a first area, an ultrasound image that is read from a storage medium and matched to a first TGC value set, display, on a second area, a gain setting window for adjusting TGC values that respectively correspond to a plurality of depth values of the ultrasound image that is matched to the first TGC value set, and receive a second TGC value set via the gain setting window; and a controller configured to update the ultrasound image matched to the first TGC value set, based on the second TGC value set.

BRIEF DESCRIPTION OF THE DRAWINGS

The above and/or other aspects will become more apparent by describing certain exemplary embodiments with reference to the accompanying drawings, in which:

FIG. 3 is a flowchart for describing a method of displaying an ultrasound image, according to an exemplary embodiment;

DETAILED DESCRIPTION

Figure 1:
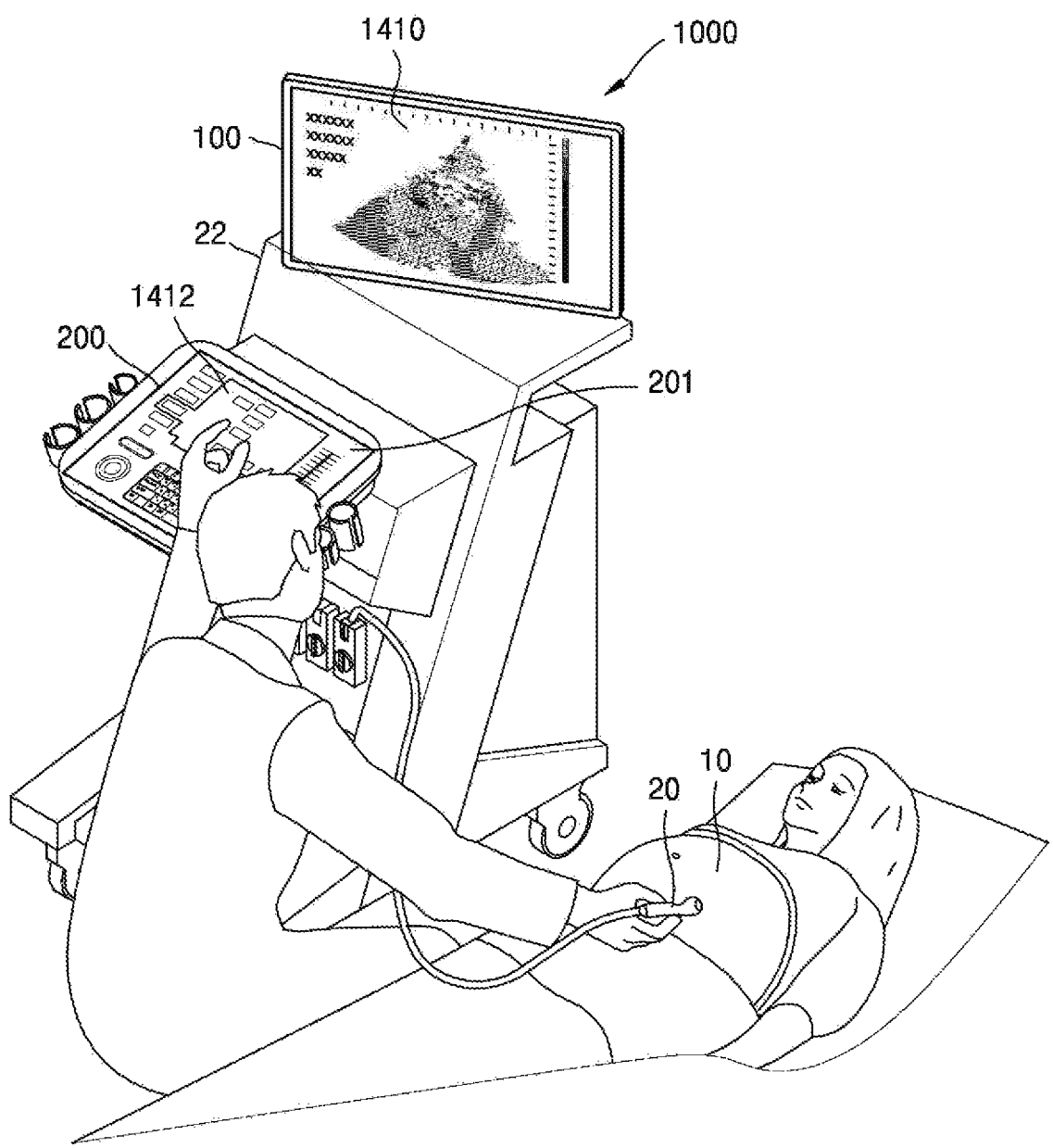
FIGS. 1, 2A, and 2B are diagrams of an ultrasound apparatus according to an exemplary embodiment.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

The terms used in this specification are those general terms currently widely used in the art in consideration of functions regarding the inventive concept, but the terms may vary according to the intention of one of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the inventive concept.

Throughout the specification, it will also be understood that when a component "includes" an element, unless there is another opposite description thereto, it should be understood that the component does not exclude another element and may further include another element. In addition, terms such as " . . . unit," " . . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), or an embryo.

Ultrasound images may be at least one of, for example, brightness (B) mode images, color (C) mode images, and Doppler (D) mode images. Also, according to an exemplary embodiment, ultrasound images may be two-dimensional (2D) or three-dimensional (3D) images. Alternatively, ultrasound images may be still images or moving images.

Furthermore, throughout the specification, a "user" may be, but is not limited to, a medical expert, such as a medical doctor, a nurse, a medical laboratory technologist, or a medical image expert.

Expressions such as "at least one of," when preceding a list of elements, modify the entire list of elements and do not modify the individual elements of the list.

Figure 2A:
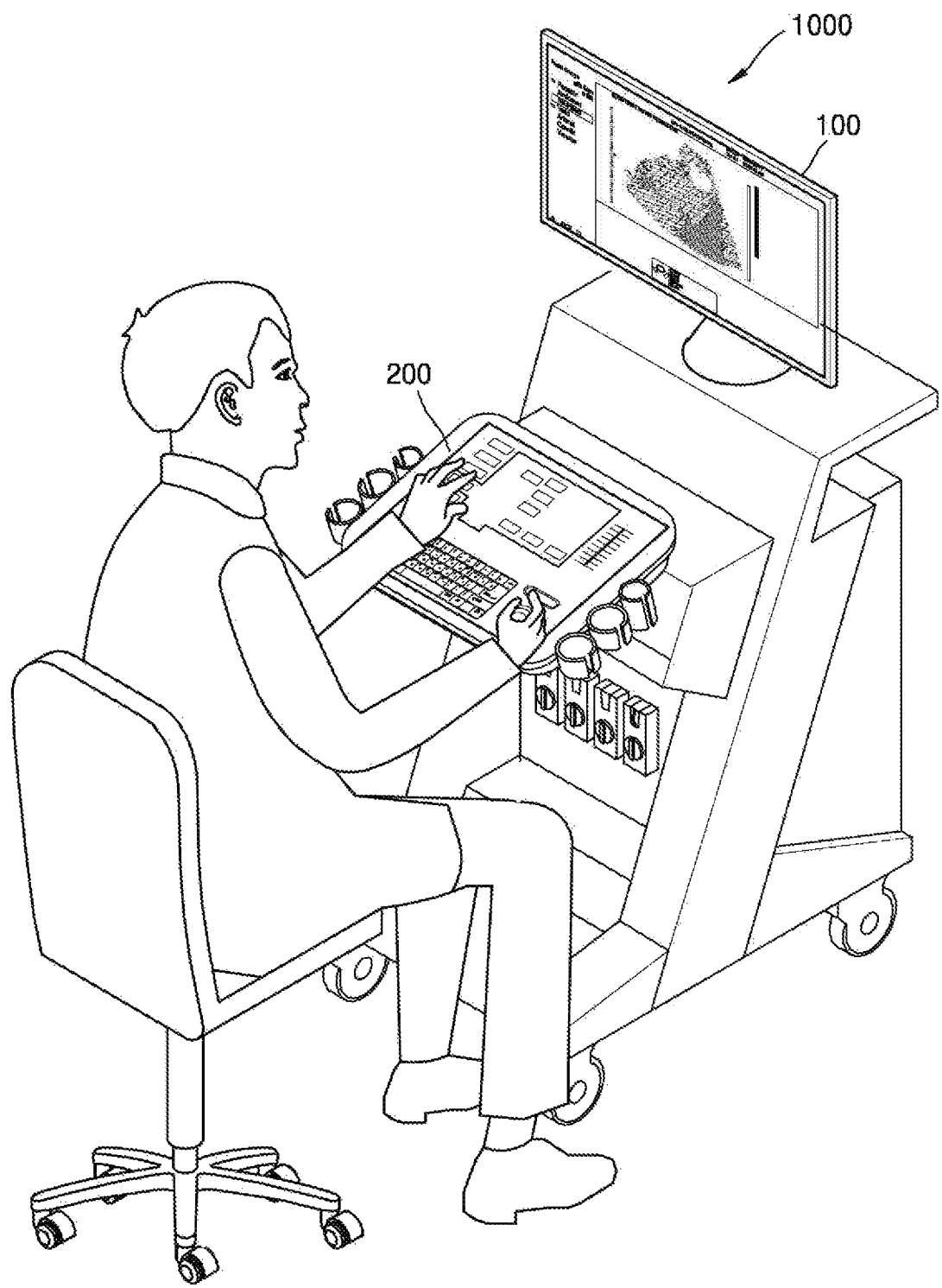
Figure 2B:
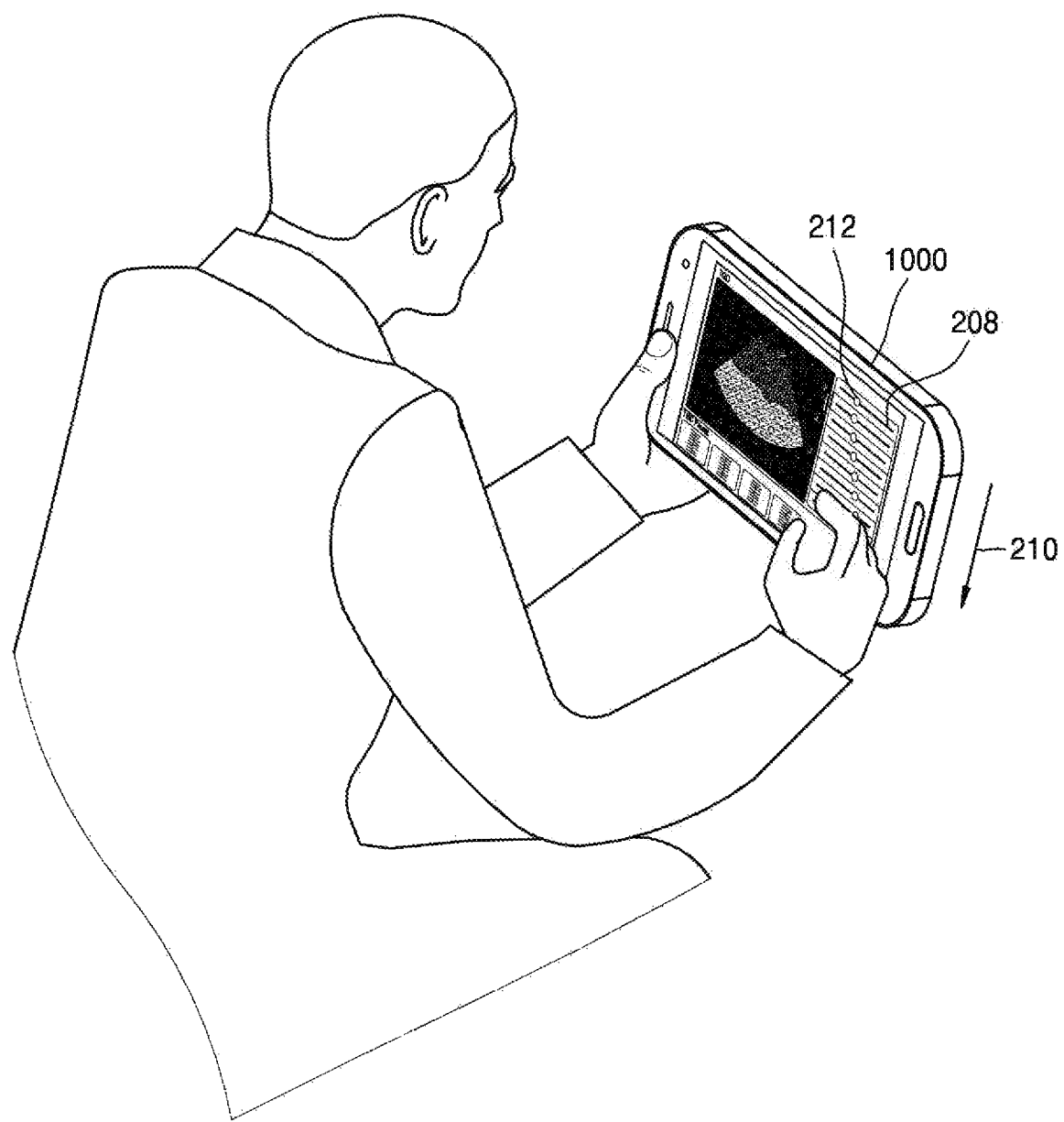

FIGS. 1, 2A, and 2B are diagrams of an ultrasound apparatus 1000 according to an exemplary embodiment.

According to an exemplary embodiment, the ultrasound apparatus 1000 may be a display apparatus for displaying an ultrasound image, and adjusting parameter values related to ultrasound echo signal data. For example, the ultrasound apparatus 1000 may receive an ultrasound echo signal reflected by an object 10, and provide a graphic user interface (GUI) to a user so that the user may set a gain value, e.g., a TGC or LGC value, of the ultrasound echo signal.

In an exemplary embodiment, the ultrasound echo signal data may include ultrasound radio frequency (RF) data, in-phase/quadrature (I/Q) phase data, and magnitude data showing intensity of the echo signal. For convenience, the ultrasound echo signal data may be referred to as raw data.

In an exemplary embodiment, parameters related to the ultrasound echo signal data refer to parameters that may be applied to the ultrasound echo signal data to compensate for sensitivity of an ultrasound image, including for example, a TGC, an LGC, a reject level, a dynamic range, and a post-processing filter. However, the parameters are not limited thereto.

TGC is a parameter for compensating for a magnitude of an ultrasound signal that decreases according to depth of a signal traveling in a human body. LGC is a parameter for compensating for uneven attenuation caused by various transmission paths of ultrasound beams.

The reject level is a parameter for removing noise of an ultrasound image. For example, the user may set the reject level by selecting any one value from 1 to 64.

The dynamic range is a parameter for adjusting brightness by modifying a ratio between a minimum value and a maximum value of an input signal. For example, the user may set a value of the dynamic range by selecting any one value from 50 to 200.

Hereinafter, an example in which a parameter related to the ultrasound echo signal data is TGC will be described for convenience.

Referring to FIG. 1, the ultrasound apparatus 1000 according to an exemplary embodiment may include a display 100, a control panel 200, a probe 20, a main body 22, and an interface for connecting the components above. Hereinafter, the components of the ultrasound apparatus 1000 will be described.

The display 100 according to an exemplary embodiment may include, but is not limited to, any one of a liquid crystal display (LCD), a thin film transistor-liquid crystal display (TFT-LCD), an organic light-emitting diode (OLED), a flexible display, and a 3D display. The display 100 may include a touch panel 1410 of a certain type (e.g., capacitive, resistive, infrared, surface acoustic wave, integral strain gauge, piezoelectric, etc.).

The display 100 may indicate a main screen for displaying an ultrasound image. The display 100 may provide real-time display of an ultrasound image obtained via the probe 20, or read and display a prestored ultrasound image. Also, the display 100 may display an ultrasound image that is received from an external server or an external device.

The control panel 200 may be a device that includes control items for controlling functions provided by the ultrasound apparatus 1000. For example, the control items may include, but is not limited to, a menu, an adjustment button, a mode selection button, a shortcut icon, an adjustment interface, function keys, and a setting window (e.g., a TGC setting window 201).

According to an exemplary embodiment, the control panel 200 may include a touch screen 1412. For example, the control panel 200 and a touch pad may be provided in a layered structure to configure a touch screen.

The touch screen may be configured to detect a touch input location, a touched area, and a touch input force. Also, the touch screen may be configured to detect a real touch and a proximity touch.

In an exemplary embodiment, the term "real touch" refers to a pointer actually touching a screen, and the term "proximity touch" refers to the pointer not actually touching the screen, but being a predetermined distance away from the screen. In an exemplary embodiment, the 'pointer' is a touch device for touching or proximity touching a certain portion of a displayed screen, for example, an electronic pen or a finger. For convenience, an example in which the pointer is a finger will be described below.

According to an exemplary embodiment, the control panel 200 may detect a touch gesture of the user via the touch screen. In an exemplary embodiment, the touch gesture (touch input) of the user may include tapping, touch and hold, double tapping, dragging, panning, flicking, drag and drop, swiping, and pinching.

"Tapping" is when the user touches a screen with a finger or an electronic pen without moving and immediately lifts the finger or the electronic pen away from the screen.

"Touch and hold" is when the user touches the screen with the finger or the electronic pen and maintains a touch input of a threshold time (e.g., 2 seconds) or more. That is, a time difference between a touch-in moment and a touch-out moment is at least the threshold time (e.g., 2 seconds). When the touch input is maintained for a threshold time, a visual, auditory, or tactile feedback signal may be provided to the user so that the user may recognize whether a touch input is tapping or touch and hold. The threshold time may vary according to exemplary embodiments.

"Double tap" is when the user touches the screen with the finger or the electronic pen twice.

"Dragging" is when the user touches the screen with the finger or the electronic pen, and moves the finger or the electronic pen to another location on the screen while maintaining the touch. Due to dragging, an object is moved or panning is performed.

"Panning" is when the user performs a dragging motion without selecting an object. Since a certain object is not selected by the panning motion, the object is not moved in a page, but the page itself may move on the screen or a group of objects may move within a page.

"Flicking" is when the user drags with the finger or the electronic pen at a threshold speed (e.g., 100 pixels/seconds) or above. Dragging (or panning and flicking) may be distinguished based on whether a moving speed of the finger or the electronic pen is equal to or greater than the threshold speed (e.g., 100 pixels/seconds).

"Drag and drop" is when the user drags an object to a location in the screen by using the finger or the electronic pen and releasing the object.

"Pinching" is when the user touches the screen with two fingers and moves the fingers in different directions. Pinching is for enlarging (pinch open) or reducing (pinch close) an object or a page, and an enlarging degree or reducing degree is determined according to a distance between the two fingers.

"Swiping" is when the user touches an object on the screen with the finger or the electronic pen and moves a predetermined distance in a horizontal or a vertical direction. For example, a diagonal motion is not detected as a swipe event.

According to an exemplary embodiment, the control panel 200 may include a hardware button (physical button). For example, the control panel 200 may include a hardware button such as, but not limited to, a trackball, a probe button, a power button, a scan button, a patient button, and an ultrasound image selection button.

According to an exemplary embodiment, the control panel 200 may be entirely formed as a touch screen, or partially include a touch screen. When the control panel 200 partially includes a touch screen, the control panel 200 may include a touch screen for displaying a GUI and hardware buttons.

The user may be able to easily select a hardware button in the control panel 200 by touching without visually identifying the control panel 200. However, since locations of software buttons on the touch screen may vary, it may be difficult for the user to identify the locations of the software buttons without looking at the software buttons. Also, the user might not be able to distinguish peripheries between the software buttons when touching. Therefore, the user has to select a software button on the touch screen while identifying locations of his/her fingers on the touch screen.

For example, in order for the user to select a button displayed on a touch screen while performing ultrasound diagnosis (e.g., scanning an ultrasound image), the user has to move his/her viewpoint from a direction toward an ultrasound image on a main screen to a direction toward the touch screen. In this case, the viewpoint of the user may be split between the display 100 displaying the ultrasound image and the control panel 200 displaying control items (e.g., menus). Therefore, the user might not be able to adjust parameters for compensating for sensitivity of the ultrasound image while scanning the ultrasound image. However, a related art ultrasound system allows an adjustment of parameters related to ultrasound echo signals only during real-time scanning of ultrasound images.

Also, since a diagnosis target is disposed nearby while scanning the ultrasound image, the user might not be able to precisely adjust parameters related to ultrasound echo signal data.

Referring to FIG. 2A, the ultrasound apparatus 1000 according to an exemplary embodiment may display a prestored ultrasound image on the display 100. Also, the ultrasound apparatus 1000 may display information of parameters related to ultrasound echo signal data of the displayed ultrasound image, on the control panel 200. In this case, since the user is not scanning the ultrasound image of the object 10, the user may precisely adjust parameters related to sensitivity of the prestored ultrasound image. The ultrasound apparatus 1000 may display the prestored ultrasound image and information of parameters corresponding to the prestored ultrasound image so that the user may accurately adjust the sensitivity of the ultrasound image. This will be described below with reference to FIG. 3.

The ultrasound apparatus 1000 according to an exemplary embodiment may be provided in various ways. For example, the ultrasound apparatus 1000 may be a fixed terminal or a mobile terminal. Examples of the mobile terminal may include a laptop computer, a personal digital assistant (PDA), a tablet personal computer (PC), and a smartphone.

Referring to FIG. 2B, the ultrasound apparatus 1000 may be a tablet PC. In this case, the control panel 200 and the display 100 may be implemented as a single touch screen. That is, a touch screen of the ultrasound apparatus 1000 may provide functions of both the control panel 200 and the display 100.

The ultrasound apparatus 1000 may transmit and receive data to and from a server connected via a medical image information system (e.g., a picture archiving and communication system (PACS)). Also, the ultrasound apparatus 1000 may perform data communication according to the Digital Imaging and Communications in Medicine (DICOM) standard.

The ultrasound apparatus 1000 may display a prestored ultrasound image or an ultrasound image received from an external source, on the touch screen. In this case, the ultrasound apparatus 1000 may display, on the touch screen, an ultrasound image and information (e.g., TGC information) of a parameter matched to the ultrasound image. In this case, since the user is not scanning an ultrasound image of the object 10, the user may precisely adjust parameters related to sensitivity of the ultrasound image displayed on the touch screen.

Although not illustrated in FIGS. 1, 2A, and 2B, the ultrasound apparatus 1000 according to an exemplary embodiment may include a stand (not shown) for attaching and detaching the control panel 200. The control panel 200 may be attached to or detached from the ultrasound apparatus 1000 by using the stand.

According to an exemplary embodiment, the ultrasound apparatus 1000 may include a sensor for detecting whether the control panel 200 is attached or detached. For example, a sensor or an interface for detecting whether the control panel 200 is attached or detached may be provided inside or outside the stand.

According to an exemplary embodiment, when the control panel 200 is detached from the ultrasound apparatus 1000, the control panel 200 may perform short distance communication with the ultrasound apparatus 1000. Examples of the short distance communication may include, but is not limited to, Wi-Fi, Bluetooth, ZigBee, Wi-Fi Direct (WFD), ultra wideband (UWB), infrared data association (IrDA), Bluetooth low energy (BLE), and near field communication (NFC).

For example, the control panel 200 may detect a location of a pointer (e.g., a finger) that touches the control panel 200, and transmit information of a location of the pointer to a communicator of the ultrasound apparatus 1000. Then, the ultrasound apparatus 1000 may select at least one control item that corresponds to the location of the pointer among a plurality of control items in the control panel 200. Alternatively, the control panel 200 may transmit information of a control item that corresponds to the location of the pointer to the communicator of the ultrasound apparatus 1000.

It may be difficult to quickly and precisely adjust parameters while scanning an ultrasound image. Therefore, hereinafter, a method of reading a stored ultrasound image after a predetermined time and compensating for sensitivity of the stored ultrasound image will be described.

FIG. 3 is a flowchart for describing a method of displaying an ultrasound image, according to an exemplary embodiment.

In operation S310, the ultrasound apparatus 1000 may read an ultrasound image stored in a storage medium.

According to an exemplary embodiment, the storage medium may be a memory in the ultrasound apparatus 1000 or an external server (e.g., a medical facility server or a cloud server) that is connected with the ultrasound apparatus 1000. According to an exemplary embodiment, the storage medium may include an external storage medium (e.g., a secure digital (SD) card or a universal serial bus (USB) device) provided outside the ultrasound apparatus 1000.

According to an exemplary embodiment, the ultrasound image stored in the storage medium may include an ultrasound image that is permanently stored in the memory, or an ultrasound image that is temporarily stored in a still image mode (e.g., a freeze mode). Also, the ultrasound image stored in the storage medium may include an ultrasound image that is received from an external device. The ultrasound image received from an external device will be described below with reference to FIG. 19.

According to an exemplary embodiment, the ultrasound apparatus 1000 may read the ultrasound image stored in the storage medium based on a user's input. For example, the ultrasound apparatus 1000 may display a list of ultrasound images (e.g., thumbnail images) stored in the storage medium. In this case, the ultrasound apparatus 1000 may receive an input of selecting at least one ultrasound image from the list. Then, the ultrasound apparatus 1000 may read the selected ultrasound image from the storage medium.

According to an exemplary embodiment, the ultrasound apparatus 1000 may receive a keyword for searching for an ultrasound image. For example, the ultrasound apparatus 1000 may receive keywords such as identification information of a diagnosis target, lesion information, annotation information, and/or a diagnosis date.

The ultrasound apparatus 1000 may read an ultrasound image that corresponds to the keyword, among the ultrasound images stored in the storage medium.

According to an exemplary embodiment, the ultrasound image that is read from the storage medium may be an ultrasound image including a lesion or an ultrasound image that is bookmarked by the user.

According to an exemplary embodiment, the ultrasound apparatus 1000 may read the ultrasound image together with TGC information which has been previously matched to the ultrasound image, and raw data (e.g., ultrasound echo signal data) of the ultrasound image.

The TGC information matched to the ultrasound image is information of digital TGC that is applied to ultrasound echo signal data to adjust brightness of the ultrasound image. The TGC information may include TGC values that respectively correspond to depth values of the ultrasound image. Hereinafter, 'TGC values that respectively correspond to depth values' will be referred to as 'TGC value set', for convenience of description.

In operation S320, the ultrasound apparatus 1000 may display the ultrasound image and the TGC information matched to the ultrasound image.

According to an exemplary embodiment, the ultrasound apparatus 1000 may display the ultrasound image and the TGC information matched to the ultrasound image on a single screen or separate screens. For example, the ultrasound apparatus 1000 may display both the ultrasound image and the TGC information on the control panel 200. Alternatively, the ultrasound apparatus 1000 may display the ultrasound image on the display 100, and display the TGC information on the control panel 200.

According to an exemplary embodiment, the ultrasound apparatus 1000 may display the TGC information on a plurality of slider bars 208. The slider bars may be arranged in parallel at predetermined intervals along a depth direction 210 of the ultrasound image. The depth direction may refer to a direction from a periphery of the object 10 to an inner area of soft tissues, i.e., a direction in which a depth value in the object increases. The slider bars may respectively correspond to the depth values of the ultrasound image.

According to an exemplary embodiment, based on TGC values in the TGC information which correspond to depth values, the ultrasound apparatus 1000 may display TGC values that are matched to the ultrasound image by moving adjustment buttons 212 on the slider bars.

According to an exemplary embodiment, the ultrasound apparatus 1000 may display a TGC line on a predetermined area of a screen. The TGC line may represent the TGC value set in the TGC information. For example, the ultrasound apparatus 1000 may display the TGC line on an area defined as a gain setting area. In this case, the TGC line may connect the TGC values that respectively correspond to the depth values.

According to an exemplary embodiment, the TGC line may be a GUI for adjusting at least one TGC value that corresponds to at least one depth value. For convenience of description, the TGC line may also be referred to as a 'TGC curve.'

According to an exemplary embodiment, when the ultrasound image and the TGC line are displayed on a single screen, the ultrasound apparatus 1000 may display the TGC line at a side of the ultrasound image such that the depth values indicated by points on the TGC line matches with the depth values of the ultrasound image. According to an exemplary embodiment, the ultrasound apparatus 1000 may display the TGC line in an area including the slider bars.

According to an exemplary embodiment, the user may identify the prestored ultrasound image and TGC information that corresponds to the prestored ultrasound image.

In operation S330, the ultrasound apparatus 1000 may receive an input of modifying the TGC information. For example, the ultrasound apparatus 1000 may receive an input of adjusting the at least one TGC value in the TGC information which corresponds to the at least one depth value.

According to an exemplary embodiment, the ultrasound apparatus 1000 may receive an input of moving the adjustment buttons on the slider bars. For example, the ultrasound apparatus 1000 may receive an input of dragging an adjustment button on the slider bar or tapping a location on the slider bar to adjust the TGC value. Also, when the user draws and drags a line or a curve in a direction perpendicular to the slider bars, the ultrasound apparatus 1000 may determine TGC values with respect to dragged locations and set the determined TGC values as TGC values corresponding to the depth values.

According to an exemplary embodiment, the ultrasound apparatus 1000 may receive an input of modifying a first TGC value set to a second TGC value set, via the TGC line. For example, the ultrasound apparatus 1000 may receive an input of touching a point on the TGC line and dragging leftward or rightward. If the user touches the point on the TGC line and drags rightward, a TGC value corresponding to a depth value at the point may increase.

Also, the ultrasound apparatus 1000 may receive a drag input in a depth axis direction within an area (e.g., gain setting area) where the TGC line is displayed. In this case, new TGC values may be set based on a location of the drag input.

According to an exemplary embodiment, when the TGC line is displayed on the slider bars, the ultrasound apparatus 1000 may receive an input of moving at least one adjustment button located at an intersection of the TGC line and the slider bars.

According to an exemplary embodiment, the ultrasound apparatus 1000 may receive an input of selecting one TGC value set from a list of TGC preset value sets. The list of TGC preset value sets will be described below with reference to FIG. 11.

In operation S340, the ultrasound apparatus 1000 may update the displayed ultrasound image based on the modified TGC information.

According to an exemplary embodiment, when the TGC information is modified, the ultrasound apparatus 1000 may apply at least one modified TGC value to ultrasound echo signal data of the displayed ultrasound image. In this case, brightness of a portion of or the entire ultrasound image may be modified. For example, as the user increases a TGC value corresponding to a first depth value, the ultrasound image may become brighter at the first depth value. As the user decreases a TGC value corresponding to a second depth value, the ultrasound image may become darker at the second depth value.

According to an exemplary embodiment, when a plurality of ultrasound image frames that respectively correspond to a plurality of TGC value sets are stored in the storage medium, the ultrasound apparatus 1000 may select a new ultrasound image frame that corresponds to a new TGC value set as the TGC information is modified. For example, when the TGC information is modified from a first TGC value set to a second TGC value set, the ultrasound apparatus 1000 may select a second ultrasound image frame that corresponds to the second TGC value set instead of a first ultrasound image frame that corresponds to the first TGC value set, e.g., the second TGC value set may be matched to the second ultrasound image frame. Also, the ultrasound apparatus 1000 may update the ultrasound image by displaying the second ultrasound image frame that corresponds to the second TGC value set instead of the first ultrasound image frame that corresponds to the first TGC value set.

The ultrasound image frames that respectively correspond to the TGC value sets may be frames generated from one piece of raw data (ultrasound echo signal data). For example, the first ultrasound image frame may be a frame obtained by applying the first TGC value set to a certain piece of ultrasound echo signal data, and the second ultrasound image frame may be a frame obtained by applying the second TGC value set to the certain piece of ultrasound echo signal data. The pieces of the ultrasound echo signal data may be the same or different. The operation of the ultrasound apparatus 1000 displaying the second ultrasound image frame instead of the first ultrasound image frame will be described below with reference to FIG. 7.

According to an exemplary embodiment, the ultrasound apparatus 1000 may match the updated ultrasound image to modified TGC information and store the updated ultrasound image in the storage medium. For example, when an ultrasound image with a desired level of sensitivity appears on a screen while adjusting the TGC values, the user may press a 'save' button. Then, in response to an input of pressing the save button, the ultrasound apparatus 1000 may match the currently displayed ultrasound image to the current TGC information (e.g., TGC values corresponding to depth values), and store the currently displayed ultrasound image in the storage medium.

Figure 4:
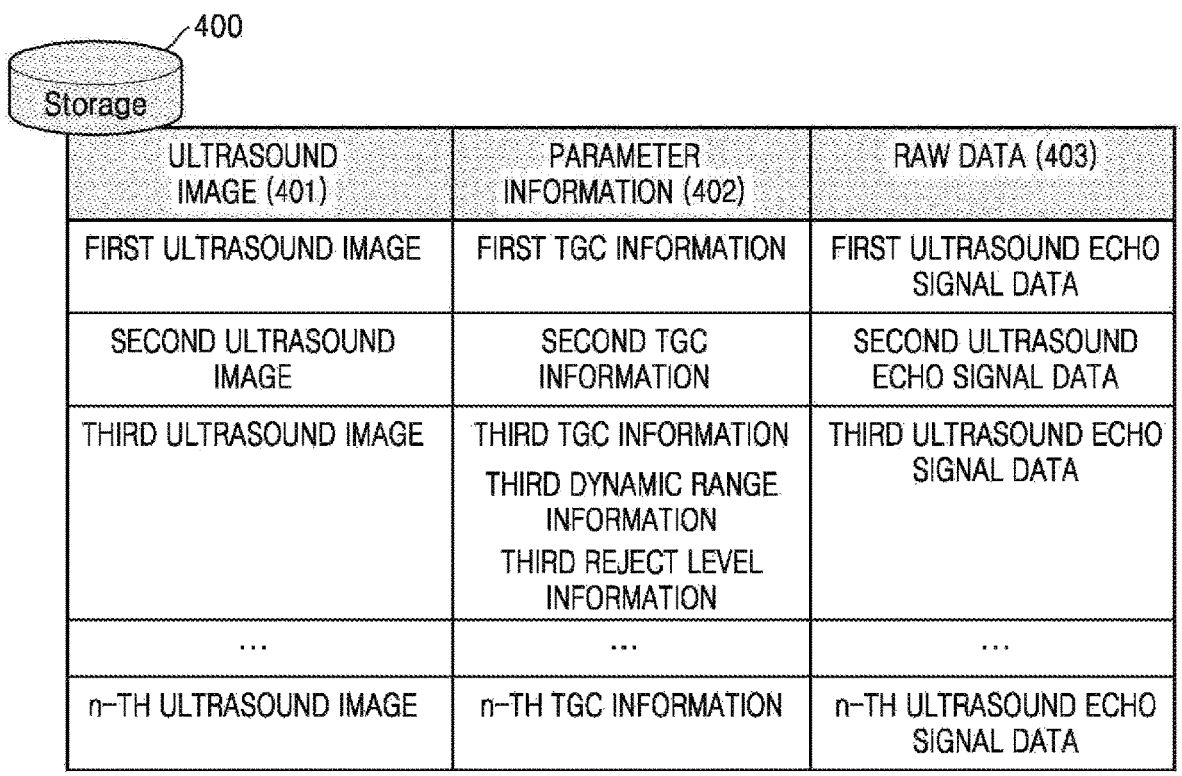
FIG. 4 is a diagram for describing an example of storing ultrasound echo signal data and TGC information in a storage medium.

FIG. 4 is a diagram for describing an example of storing ultrasound echo signal data and TGC information in a storage medium 400.

Referring to FIG. 4, an ultrasound image 401, parameter information 402, and raw data (e.g., ultrasound echo signal data) 403 may be matched and stored in the storage medium 400. For example, when a first ultrasound image is obtained by applying first TGC information to first ultrasound echo signal data, the first ultrasound image, the first TGC information, and the first ultrasound echo signal data may be matched and stored in the storage medium 400.

When a second ultrasound image is obtained by applying second TGC information and second LGC information to second ultrasound echo signal data, the second ultrasound image, the second TGC information, the second LGC information, and the second ultrasound echo signal data may be matched and stored in the storage medium 400.

When a third ultrasound image is obtained by applying third TGC information, third dynamic range information, and third reject level information to third ultrasound echo signal data, the third ultrasound image, the third TGC information, the third dynamic range information, and the third reject level information may be matched and stored in the storage medium 400. The data for the fourth to nth ultrasound images, the fourth to nth echo signal data, and the fourth to nth TGC information may be stored according to any of the above descriptions.

Hereinafter, an operation of the ultrasound apparatus 1000 modifying parameters of a prestored ultrasound image will be described with reference to FIGS. 5A to 5D.

Figure 5A:
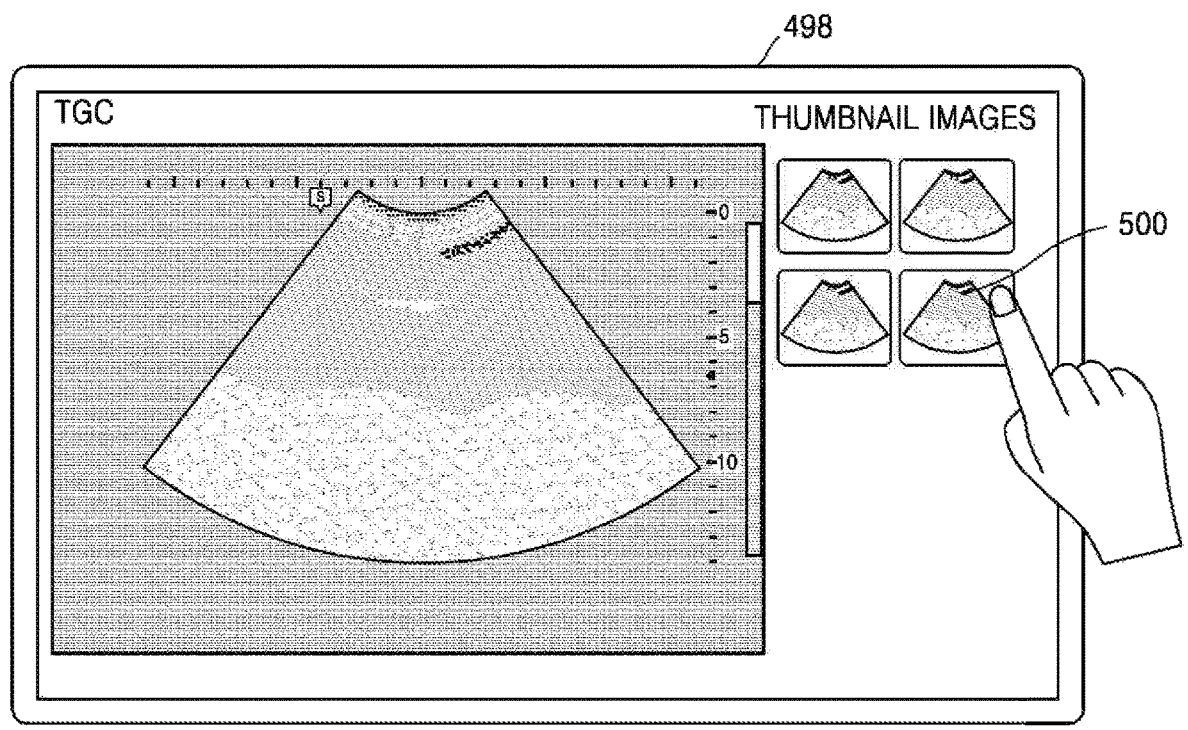
FIG. 5A is a diagram of a screen for selecting an ultrasound image stored in a storage medium.
Figure 5B:
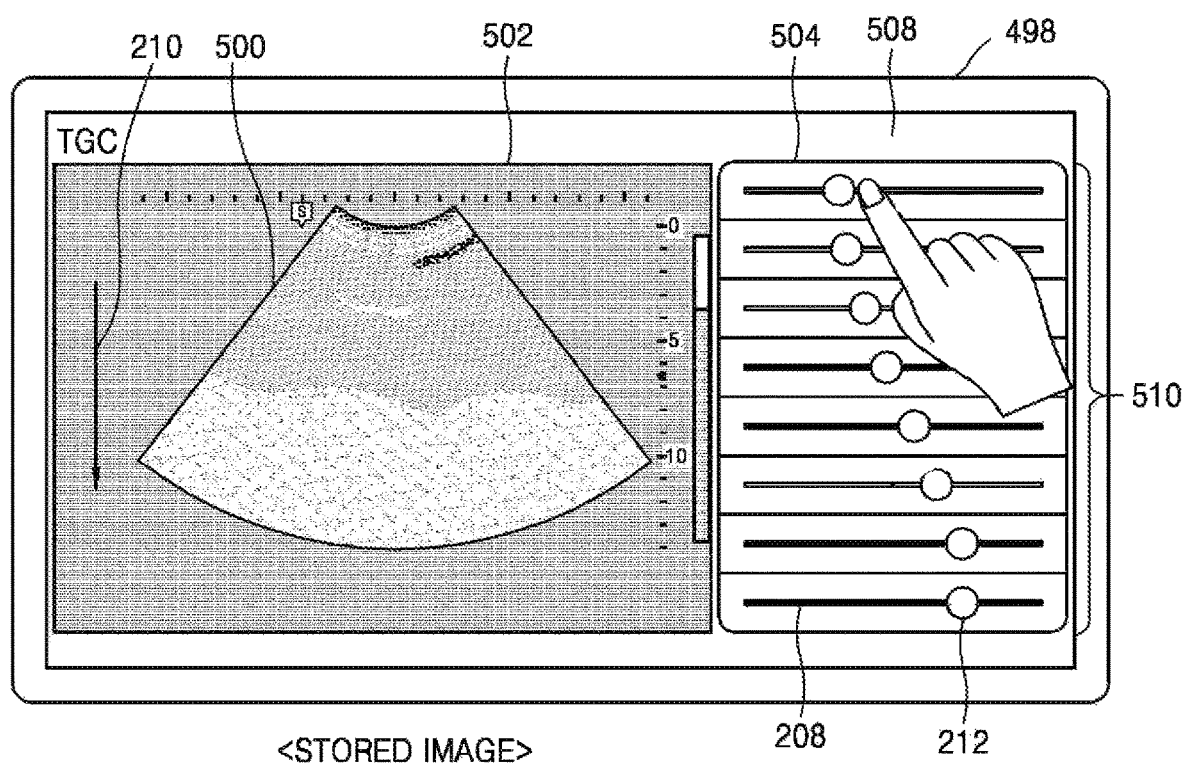
FIG. 5B is a diagram of a screen showing TGC information that is matched to a stored image.
Figure 5C:
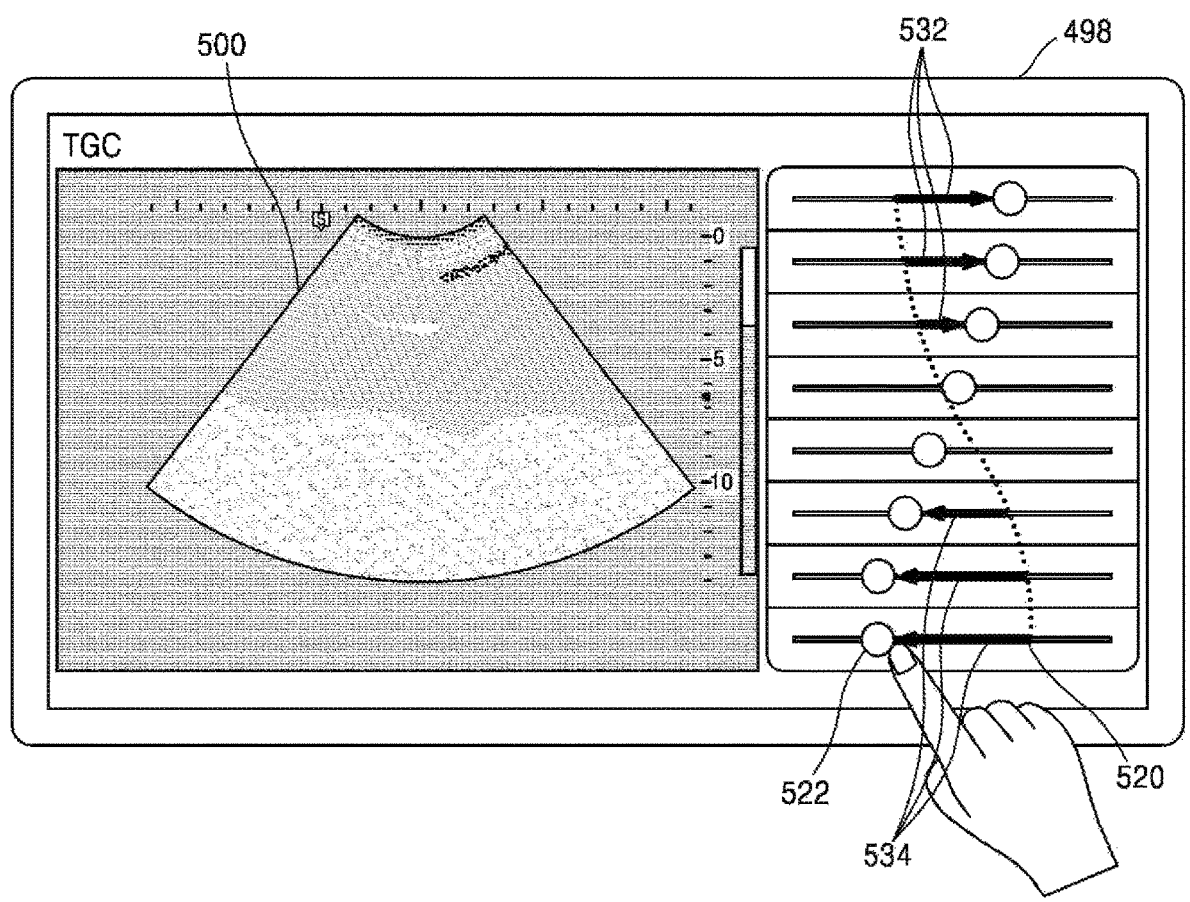
FIG. 5C is a diagram of a screen for receiving an input of modifying TGC information.
Figure 5D:
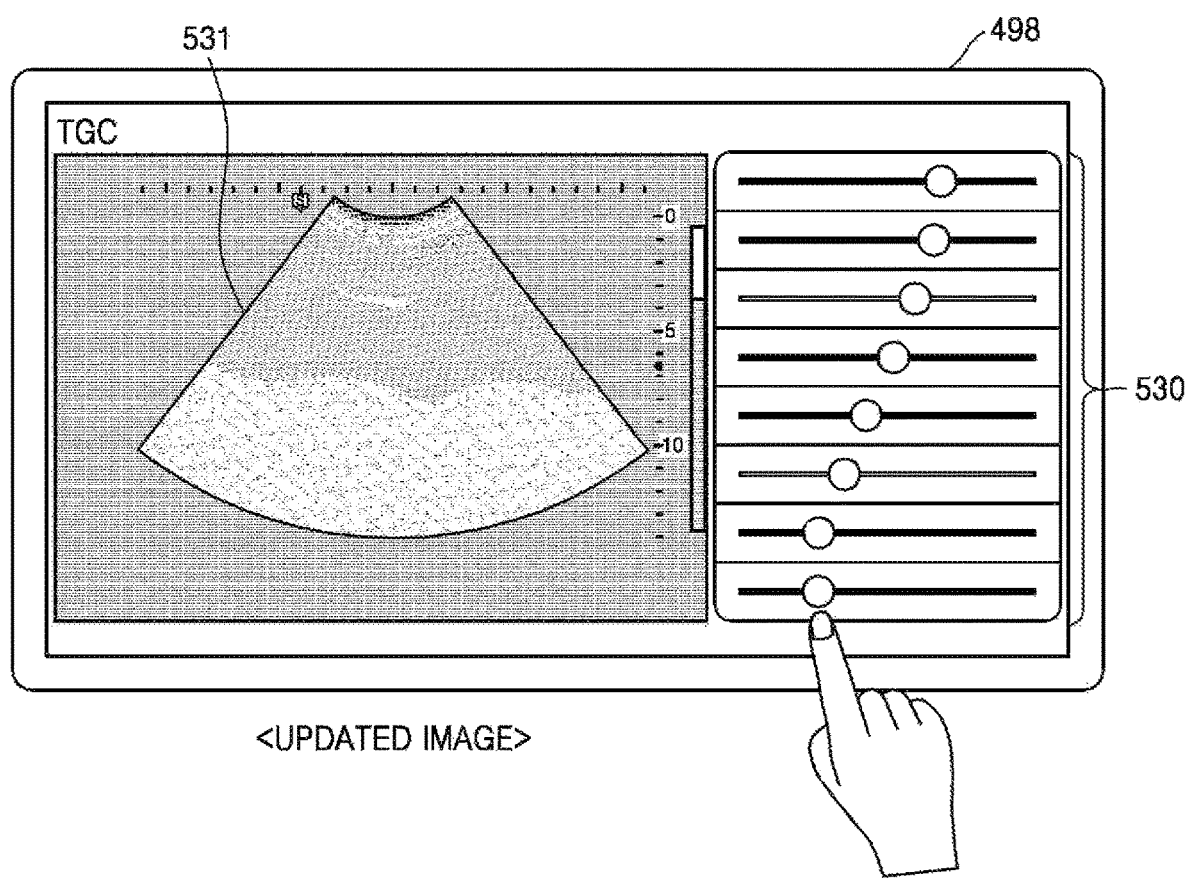
FIG. 5D is a diagram of a screen showing an ultrasound image that is updated according to modified TGC information.

FIG. 5A is a diagram of a screen for selecting an ultrasound image stored in a storage medium, FIG. 5B is a diagram of a screen showing TGC information that is matched to a stored image, FIG. 5C is a diagram of a screen for receiving an input of modifying TGC information, and FIG. 5D is a diagram of a screen showing an ultrasound image that is updated according to modified TGC information.

Referring to FIG. 5A, the ultrasound apparatus 1000 may display a list of ultrasound images stored in a storage medium. For example, the ultrasound apparatus 1000 may display respective thumbnail images of the ultrasound images stored in the storage medium on an area of a screen 498. According to an exemplary embodiment, when the user inputs a keyword, the ultrasound apparatus 1000 may filter the ultrasound images and display thumbnail images of the ultrasound images that correspond to the keyword.

The ultrasound apparatus 1000 may receive an input of selecting one of the thumbnail images from the user. For example, the ultrasound apparatus 1000 may receive an input of touching a thumbnail image of a first ultrasound image 500.

Although an example of the user selecting one of the thumbnail images has been described above with reference to FIG. 5A, an ultrasound image may be selected in various ways.

Referring to FIG. 5B, the ultrasound apparatus 1000 may display the stored ultrasound image, e.g., the first ultrasound image 500, which is selected by the user, on a first area 502 of the screen. Also, the ultrasound apparatus 1000 may display first TGC information 510 matched to the first ultrasound image 500, on a second area 508 of the screen. For example, the ultrasound apparatus 1000 may display, on a gain setting window or area 504 including slider bars 208, a TGC value set matched to depth values of the first ultrasound image 500. In this case, the user may identify TGC values that correspond to the depth values of the first ultrasound image 500 selected by the user.

Referring to FIG. 5C, the ultrasound apparatus 1000 may receive an input (reference numeral 520) of modifying the first TGC information 510 from the user. For example, the input may include an input of modifying at least one TGC value that corresponds to the depth values of the first ultrasound image 500. The user may move at least one adjustment button 522 on the slider bars and thus set a desired TGC value for each depth area.

Referring to FIG. 5D, when the first TGC information 510 is modified to second TGC information 530, the ultrasound apparatus 1000 may apply the second TGC information 530 to ultrasound echo signal data of the first ultrasound image 500, to obtain the updated first ultrasound image 531. In this case, brightness of the first ultrasound image 500 may be modified. For example, an upper area of the first ultrasound image 500 may become brighter because an increase of a TGC value in an upper depth area (arrows 532 in FIG. 5C), and a lower area of the first ultrasound image 500 may become darker because of a decrease of the TGC value in a deeper depth area (arrows 534 in FIG. 5C).

According to an exemplary embodiment, the user may modify the TGC values of the prestored ultrasound image to obtain an ultrasound image with a desired level of sensitivity.

Figure 6:
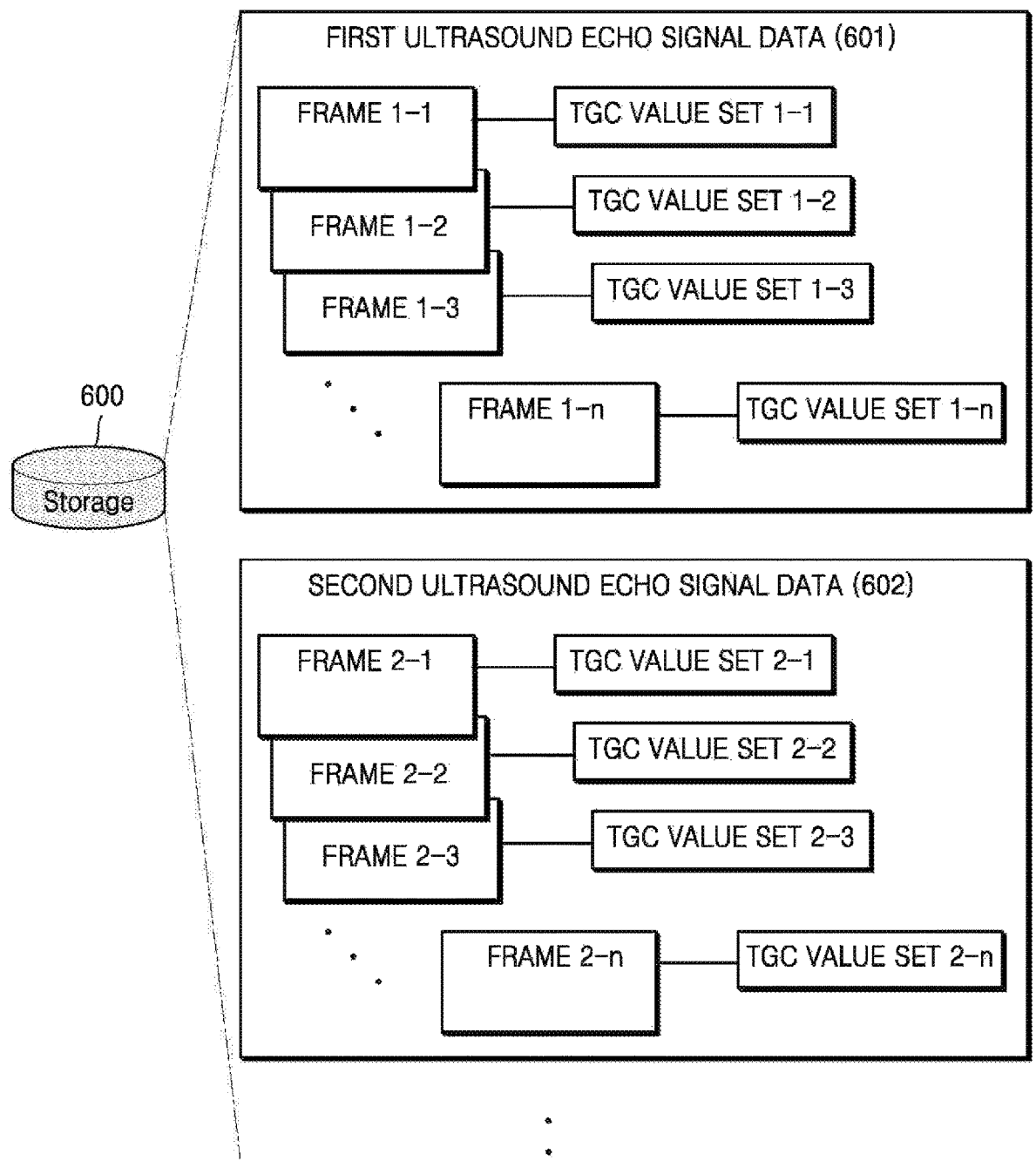
FIG. 6 is a diagram for describing an example of storing a plurality of ultrasound image frames related to ultrasound echo signal data in a storage medium.

FIG. 6 is a diagram for describing an example of storing a plurality of ultrasound image frames related to ultrasound echo signal data in a storage medium 600.

Referring to FIG. 6, a storage medium 600 may store a plurality of ultrasound image frames that correspond to a certain piece of ultrasound echo signal data. For example, the ultrasound apparatus 1000 may store first ultrasound echo signal data 601, a frame 1-1 obtained by applying a TGC value set 1-1 to the first ultrasound echo signal data 601, a frame 1-2 obtained by applying a TGC value set 1-2 to the first ultrasound echo signal data 601, a frame 1-3 obtained by applying a TGC value set 1-3 to the first ultrasound echo signal data 601, . . . a frame 1-$n$ obtained by applying a TGC value set 1-$n$ to the first ultrasound echo signal data 601. An identification value of the frame 1-1 may be matched to the TGC value set 1-1, an identification value of the frame 1-2 may be matched to the TGC value set 1-2, an identification value of the frame 1-3 may be matched to the TGC value set 1-3, and the identification values may be saved.

Also, when storing second ultrasound echo signal data 602, the ultrasound apparatus 1000 may store a frame 2-1 obtained by applying a TGC value set 2-1 to the second ultrasound echo signal data 602, a frame 2-2 obtained by applying a TGC value set 2-2 to the second ultrasound echo signal data 602, a frame 2-3 obtained by applying a TGC value set 2-3 to the second ultrasound echo signal data 602, . . . a frame 2-$n$ obtained by applying a TGC value set 2-$n$ to the second ultrasound echo signal data 602. An identification value of the frame 2-1 may be matched to the TGC value set 2-1, an identification value of the frame 2-2 may be matched to the TGC value set 2-2, an identification value of the frame 2-3 may be matched to the TGC value set 2-3, and the identification values may be saved.

According to an exemplary embodiment, the ultrasound apparatus 1000 may apply a plurality of TGC value sets to the ultrasound echo signal data, and thus generate, in advance, a plurality of ultrasound image frames that may be generated from the ultrasound echo signal data. The TGC value sets may be predefined sets. For example, the TGC value sets may be predefined with respect to identification information of the probe 20 that is connected to the ultrasound apparatus 1000. Alternatively, the TGC value sets may be defined by the user or sets of patterns that are frequently used by the user.

Figure 7:
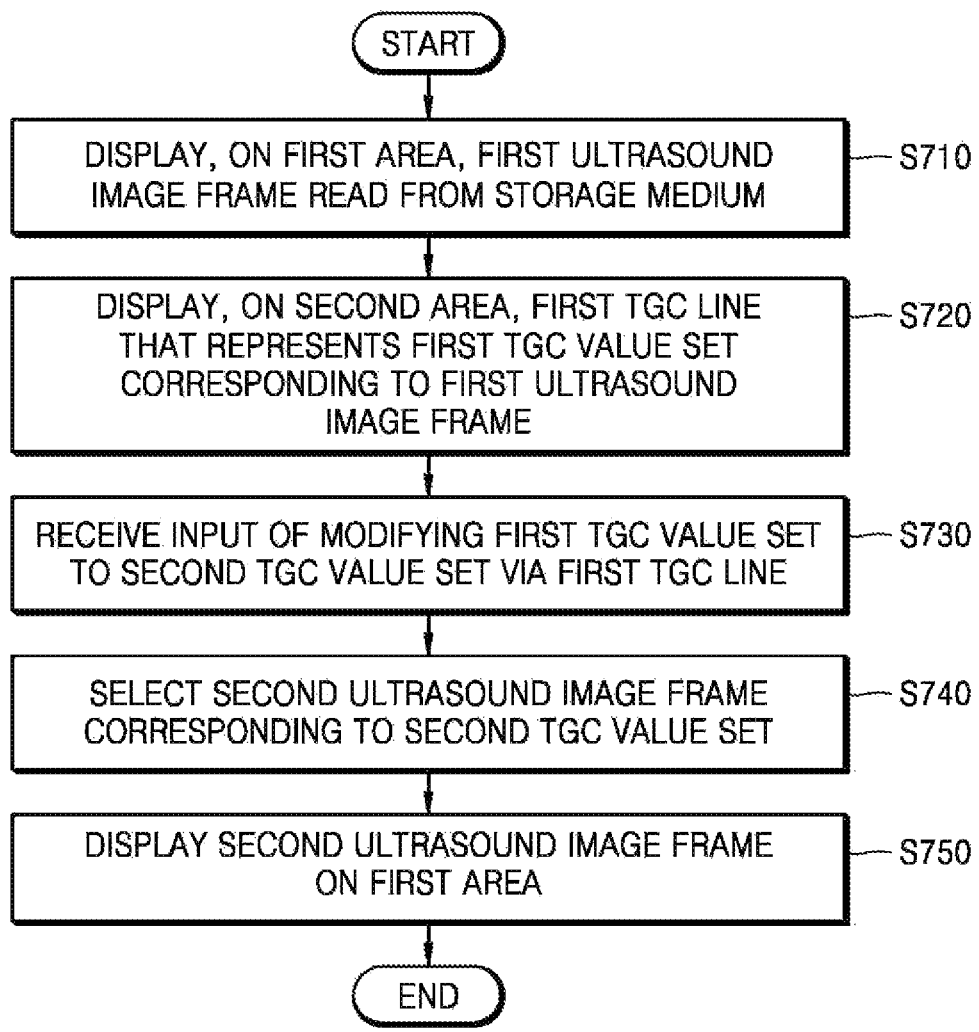
FIG. 7 is a flowchart of a method of selecting an ultrasound image frame corresponding to new TGC information, according to an exemplary embodiment.

FIG. 7 is a flowchart of a method of selecting an ultrasound image frame corresponding to new TGC information, according to an exemplary embodiment.

In operation S710, the ultrasound apparatus 1000 may display, on a first area of a screen, a first ultrasound image frame that is read from the storage medium 600. The first ultrasound image frame may be obtained by applying a first TGC value set to first ultrasound image echo signal data.

In operation S720, the ultrasound apparatus 1000 may display, on a second area of the screen, a first TGC line that represents a first TGC value set corresponding to the first ultrasound image frame. For example, the ultrasound apparatus 1000 may display the first TGC line in the second area that is defined as a gain setting area which includes the slider bars. The first TGC line may be a line that connects TGC values included in the first TGC value set.

According to an exemplary embodiment, the ultrasound apparatus 1000 may display the first TGC line at a side of the first ultrasound image frame such that depth values indicated by points on the first TGC line are matched to depth values of an ultrasound image. For example, the ultrasound apparatus 1000 may display the first TGC line at a side of the first ultrasound image frame such that a minimum depth value of the first ultrasound image frame is matched to a maximum value point of the first TGC line, and a maximum depth value of the first ultrasound image frame is matched to a minimum value point of the first TGC line.

According to an exemplary embodiment, the ultrasound apparatus 1000 may display the first TGC line at a second area that includes a plurality of slider bars.

In operation S730, the ultrasound apparatus 1000 may receive an input of modifying the first TGC value set to a second TGC value set via the first TGC line.

For example, the ultrasound apparatus 1000 may receive an input of selecting a depth value by dragging upward or downward along the first TGC line. Also, the ultrasound apparatus 1000 may receive an input of touching a first point corresponding to a certain depth value on a first TGC line and dragging leftward or rightward. For example, the user may adjust a TGC value corresponding to a first depth value by dragging downward along the first TGC line and dragging leftward or rightward at a first point that corresponds to the first depth value.

In operation S740, the ultrasound apparatus 1000 may select a second ultrasound image frame that corresponds to the second TGC value set.

According to an exemplary embodiment, the first and second ultrasound image frames may be obtained from an identical piece of ultrasound echo signal data. For example, the first ultrasound image frame may be obtained by applying the first TGC value set to the first ultrasound echo signal data, and the second ultrasound image frame may be obtained by applying the second TGC value set to the first ultrasound echo signal data.

Therefore, among a plurality of ultrasound image frames obtained from the first ultrasound echo signal data, the ultrasound apparatus 1000 may select the second ultrasound image frame that corresponds to the second TGC value set.

In operation S750, the ultrasound apparatus 1000 may display the second ultrasound image frame on the first area.

Figure 8A:
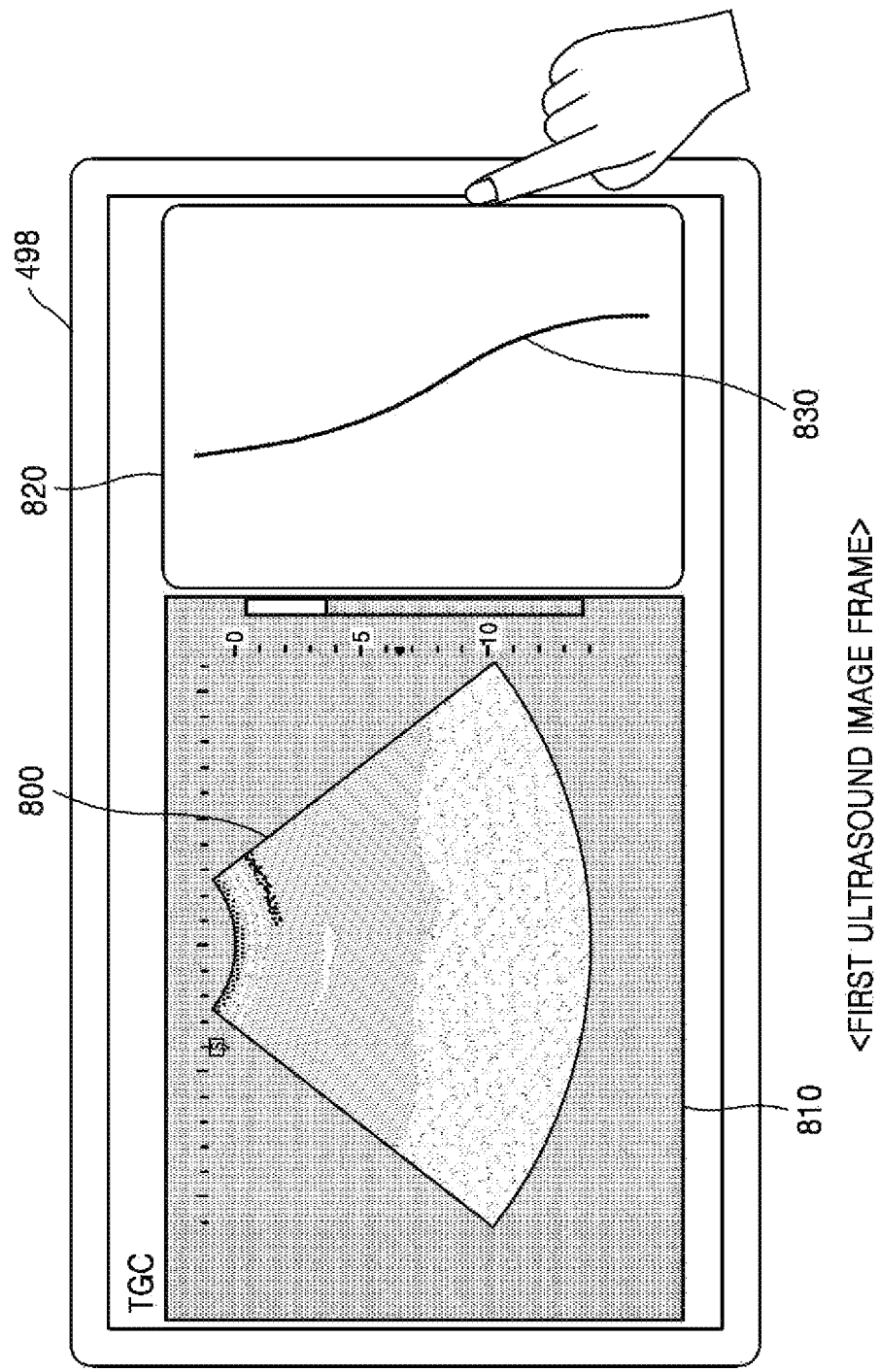
FIGS. 8A and 8B are examples of displaying, when a new TGC value is received via a TGC line, an ultrasound image frame corresponding to the new TGC value.
Figure 8B:
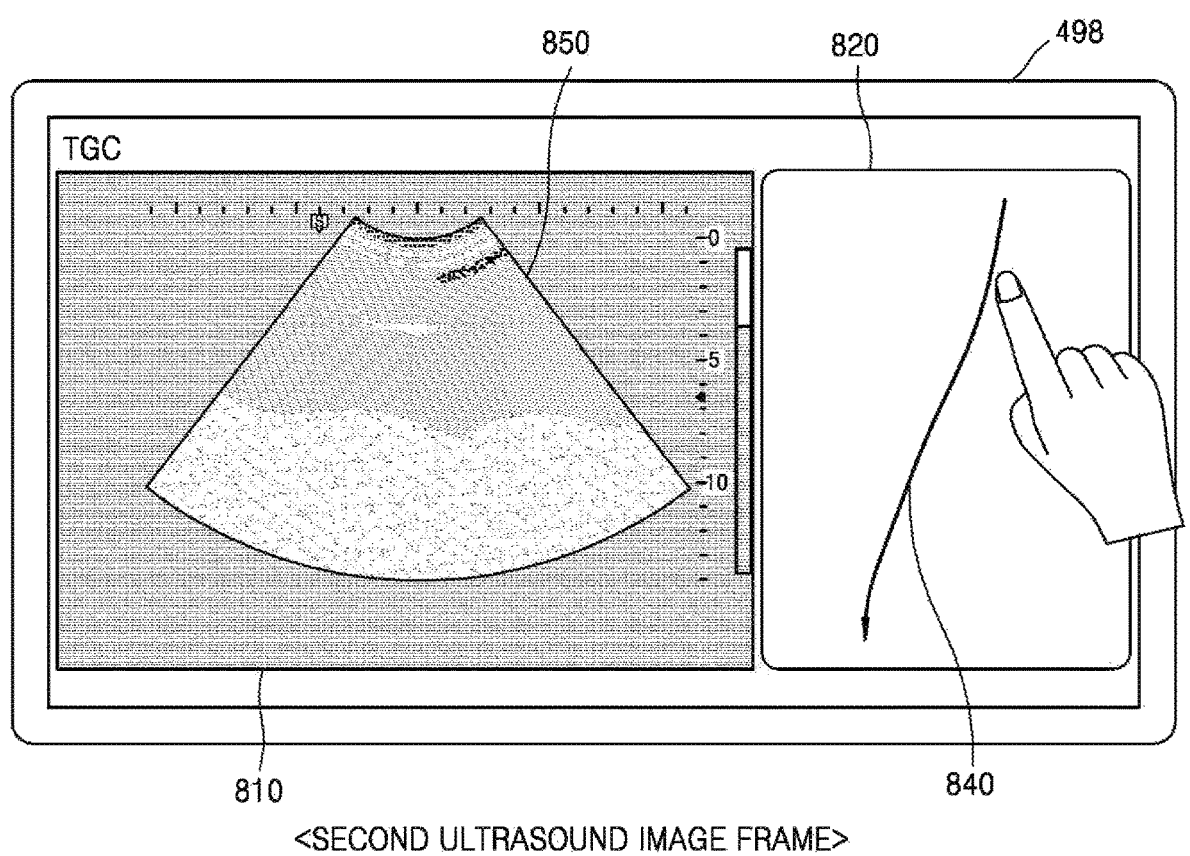

For example, the ultrasound apparatus 1000 may display, in the first area of the screen, the second ultrasound image frame instead of the first ultrasound image frame that corresponds to the first TGC value set. With reference to FIGS. 8A and 8B, an operation of the ultrasound apparatus 1000 updating an ultrasound image by displaying a second ultrasound image frame in a first area will be described below.

FIGS. 8A and 8B are examples of displaying, when a new TGC value is received via a TGC line, an ultrasound image frame corresponding to the new TGC value.

Referring to FIG. 8A, the ultrasound apparatus 1000 may display a prestored first ultrasound image frame 800 in a first area 810, and display a first TGC line 830, which represents a first TGC value set that is matched to the first ultrasound image frame 800, in a second area 820. The second area 820 may be defined as a gain setting area.

Referring to FIG. 8B, based on a user's input of dragging an inner portion of the first TGC line 830 on the second area 820, the ultrasound apparatus 1000 may modify the first TGC value set to a second TGC value set. In this case, in the second area 820, a second TGC line 840, which corresponds to the second TGC value set, may be displayed instead of the first TGC line 830 that corresponds to the first TGC value set. The second TGC line 840 may correspond to the dragged line.

Among a plurality of ultrasound image frames related to the first ultrasound image frame 800, the ultrasound apparatus 1000 may select a second ultrasound image frame that is generated by applying the second TGC value set to the ultrasound echo signal data. The ultrasound apparatus 1000 may display a second ultrasound image frame 850 in the first area 810, instead of the first ultrasound image frame 800.

According to an exemplary embodiment, when the ultrasound apparatus 1000 read a prestored ultrasound image and displays the read ultrasound image on a screen, the ultrasound apparatus 1000 does not display TGC information that corresponds to the read ultrasound image. An example in which the ultrasound apparatus 1000 does not display TGC information that is matched to an ultrasound image will be described below with reference to FIG. 9.

Figure 9:
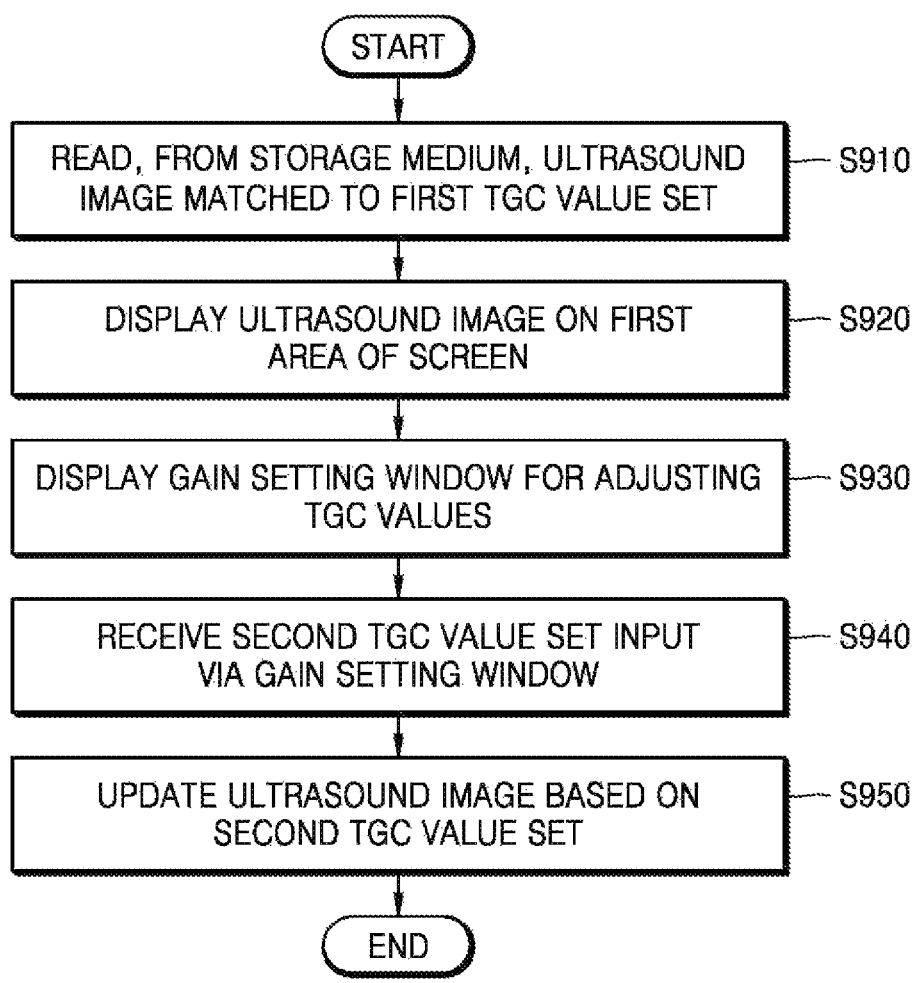
FIG. 9 is a flowchart of a method of displaying an ultrasound image, according to an exemplary embodiment.

FIG. 9 is a flowchart of a method of displaying an ultrasound image, according to an exemplary embodiment.

In operation S910, the ultrasound apparatus 1000 may read an ultrasound image, which is matched to a first TGC value set, from a storage medium.

According to an exemplary embodiment, the storage medium may be a memory in the ultrasound apparatus 1000 or an external server (e.g., a medical facility server or a cloud server) that is connected with the ultrasound apparatus 1000. According to an exemplary embodiment, the storage medium may include an external storage medium (e.g., an SD card or a USB device) provided outside the ultrasound apparatus 1000.

According to an exemplary embodiment, the ultrasound image stored in the storage medium may include an ultrasound image that is permanently stored in the memory, or an ultrasound image that is temporarily stored in a still image mode (e.g., a freeze mode). Also, the ultrasound image stored in the storage medium may include an ultrasound image that is received from an external device.

According to an exemplary embodiment, the ultrasound apparatus 1000 may read the ultrasound image stored in the storage medium based on a user's input. For example, the ultrasound apparatus 1000 may display a list of ultrasound images (e.g., thumbnail images) stored in the storage medium. In this case, the ultrasound apparatus 1000 may receive an input of selecting at least one ultrasound image from the list. Then, the ultrasound apparatus 1000 may read the selected ultrasound image from the storage medium.

According to an exemplary embodiment, the ultrasound apparatus 1000 may receive a keyword for searching for an ultrasound image. For example, the ultrasound apparatus 1000 may receive keywords such as identification information of a diagnosis target, lesion information, annotation information, and/or a diagnosis date.

The ultrasound apparatus 1000 may read an ultrasound image that corresponds to the keyword, among the ultrasound images stored in the storage medium.

According to an exemplary embodiment, the ultrasound image that is read from the storage medium may be an ultrasound image including lesion or an ultrasound image that is bookmarked by the user.

According to an exemplary embodiment, the ultrasound apparatus 1000 may read the ultrasound image together with TGC information matched to the ultrasound image, and raw data (e.g., ultrasound echo signal data) of the ultrasound image.

In operation S920, the ultrasound apparatus 1000 may display, on a first area of a screen, the ultrasound image that is matched to the first TGC value set.

In operation S930, the ultrasound apparatus 1000 may display, in a second area of the screen, a gain setting window for adjusting TGC values that correspond to depth values of the read ultrasound image.

According to an exemplary embodiment, the ultrasound apparatus 1000 may display a plurality of slider bars corresponding to the depth values on the gain setting window, and reset locations of buttons on the slider bars. For example, the ultrasound apparatus 1000 may align the buttons on the slider bars at the center positions of the slider bars.

According to an exemplary embodiment, a reference line may be vertically (in a depth direction) displayed in the gain setting window. The reference line may be a GUI for setting a TGC curve.

According to an exemplary embodiment, the first area and the second area may be included in a single screen or separate screens. For example, the first and second areas may both be included in the control panel 200. Alternatively, the first area may be included in the display 100, and the second area may be included in the control panel 200.

In operation S940, the ultrasound apparatus 1000 may receive a second TGC value set via the gain setting window.

According to an exemplary embodiment, the ultrasound apparatus 1000 may receive an input of moving adjustment buttons on the slider bars. For example, the ultrasound apparatus 1000 may receive an input of dragging an adjustment button on the slider bar or tapping a location on the slider bar to adjust the TGC value. Also, when the user draws and drags a line or a curve in a direction perpendicular to the slider bars, the ultrasound apparatus 1000 may determine TGC values with respect to dragged locations and set the determined TGC values as TGC values corresponding to the depth values.

According to an exemplary embodiment, the ultrasound apparatus 1000 may receive an input of modifying a first TGC value set to a second TGC value set, via a reference line in a vertical direction (hereinafter, referred to as 'vertical reference line'). For example, the ultrasound apparatus 1000 may receive an input of touching a point on the vertical reference line and dragging leftward or rightward. If the user touches the point on the vertical reference line and drags rightward, a TGC value corresponding to a depth value at the point may increase.

Also, the ultrasound apparatus 1000 may receive a drag input in a depth axis direction within a portion of the gain setting window that does not include the slider bars. In this case, new TGC values may be set based on a location of the drag input.

According to an exemplary embodiment, when the vertical reference line is displayed on the slider bars, the ultrasound apparatus 1000 may receive an input of moving at least one adjustment button located at an intersection of the vertical reference line and the slider bars.

According to an exemplary embodiment, the ultrasound apparatus 1000 may receive an input of selecting one TGC value set from a list of TGC preset value sets. The list of TGC preset value sets will be described below with reference to FIG. 11.

In operation S950, based on the second TGC value set, the ultrasound apparatus 1000 may update the ultrasound image that is matched to the second TGC value set. For example, the ultrasound apparatus 1000 may adjust brightness of the entire or a portion of the ultrasound image by applying second TGC values in the second TGC value set to the ultrasound echo signal data of the ultrasound image.

According to an exemplary embodiment, the ultrasound apparatus 1000 may match the updated ultrasound image to the second TGC value set and store the updated ultrasound image in the storage medium. For example, when an ultrasound image with a desired level of sensitivity appears in the first area while adjusting the TGC values in the gain setting window, the user may press a 'save' button. Then, in response to an input of pressing the save button, the ultrasound apparatus 1000 may match the ultrasound image displayed in the first area to current TGC information (e.g., TGC values corresponding to depth values) displayed in the second area, and store the ultrasound image in the storage medium.

Figure 10A:
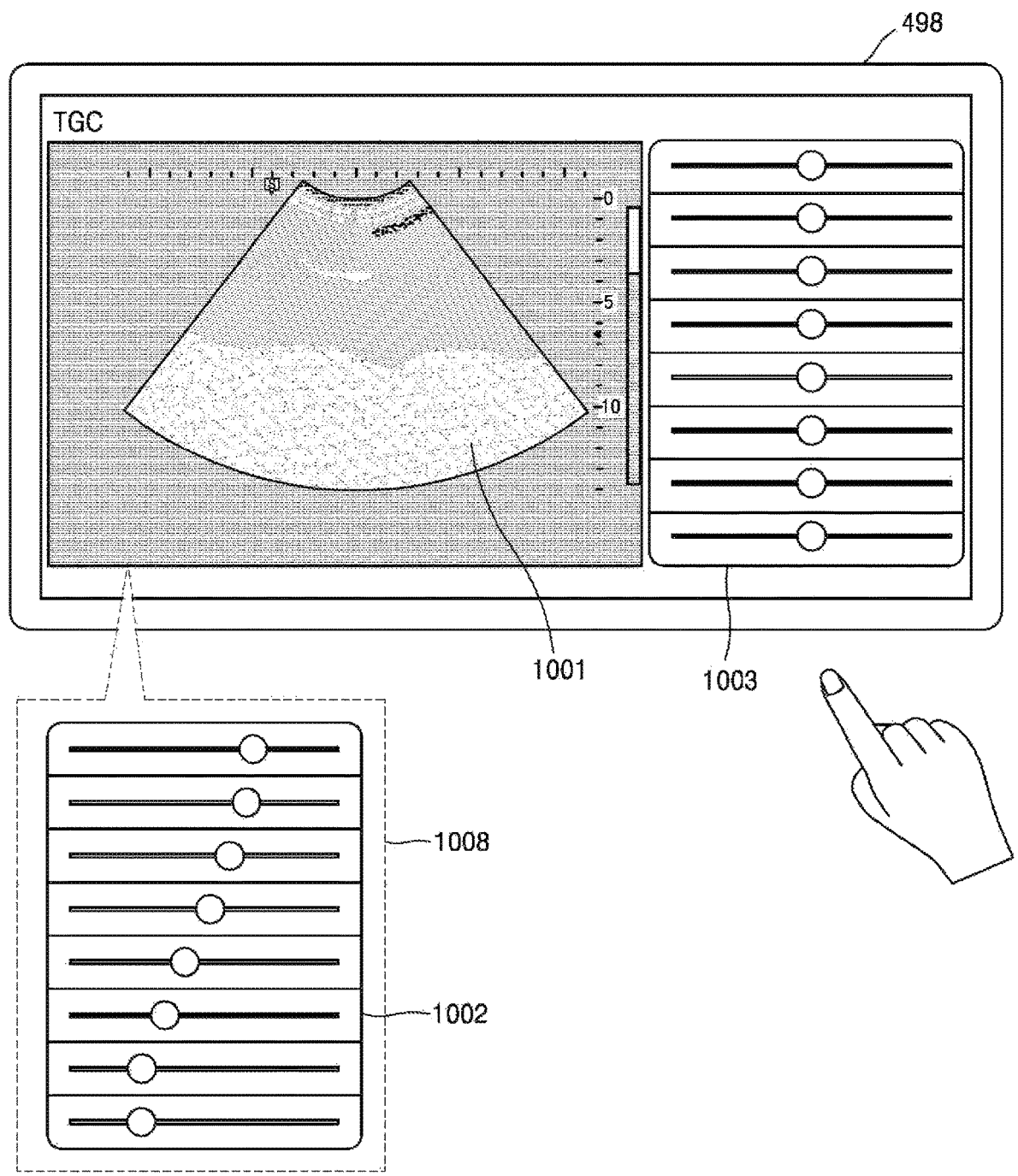
FIGS. 10A, 10B, and 10C are diagrams for describing an ultrasound apparatus updating an ultrasound image that is read from a storage medium based on a new TGC line that is input via a gain setting window.
Figure 10B:
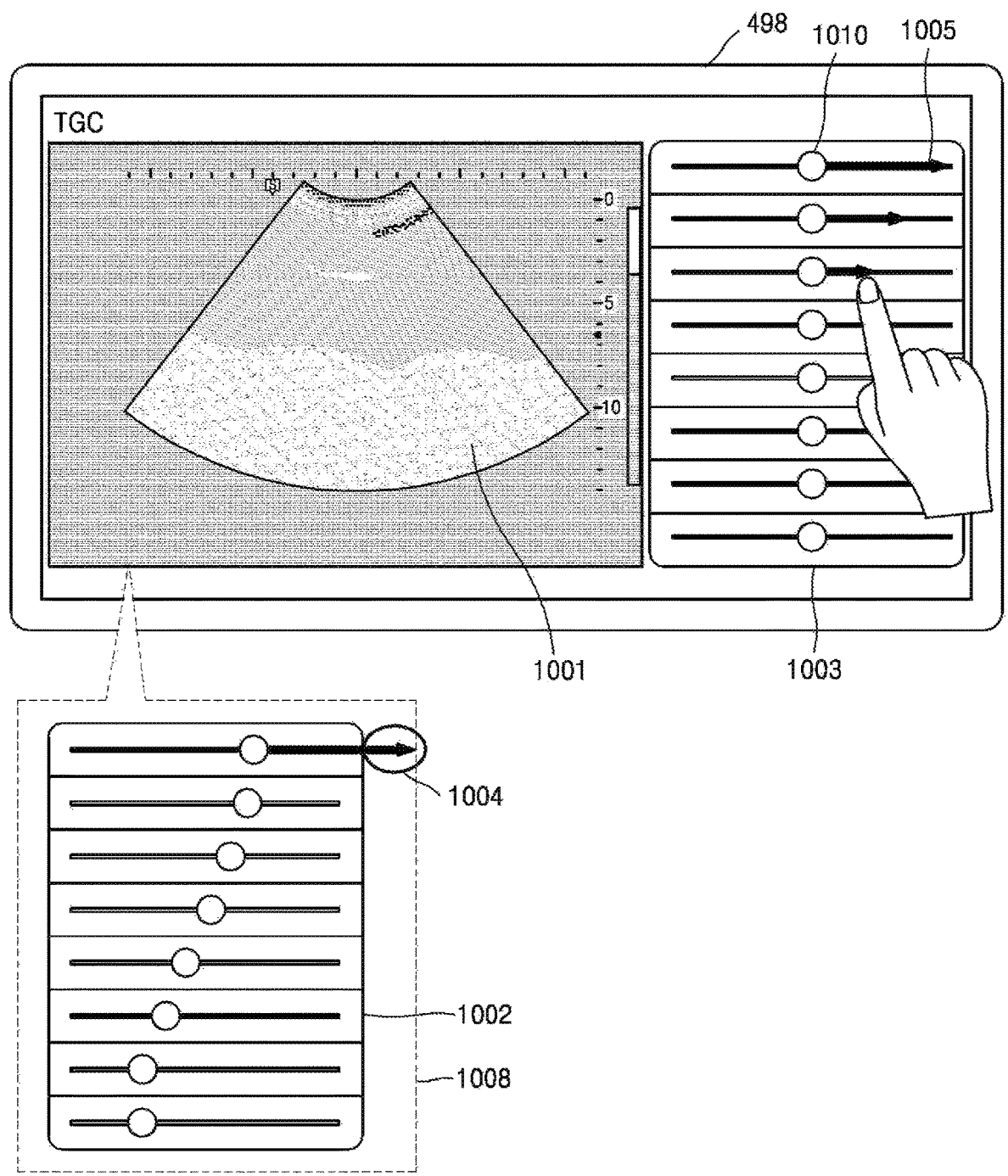
Figure 10C:
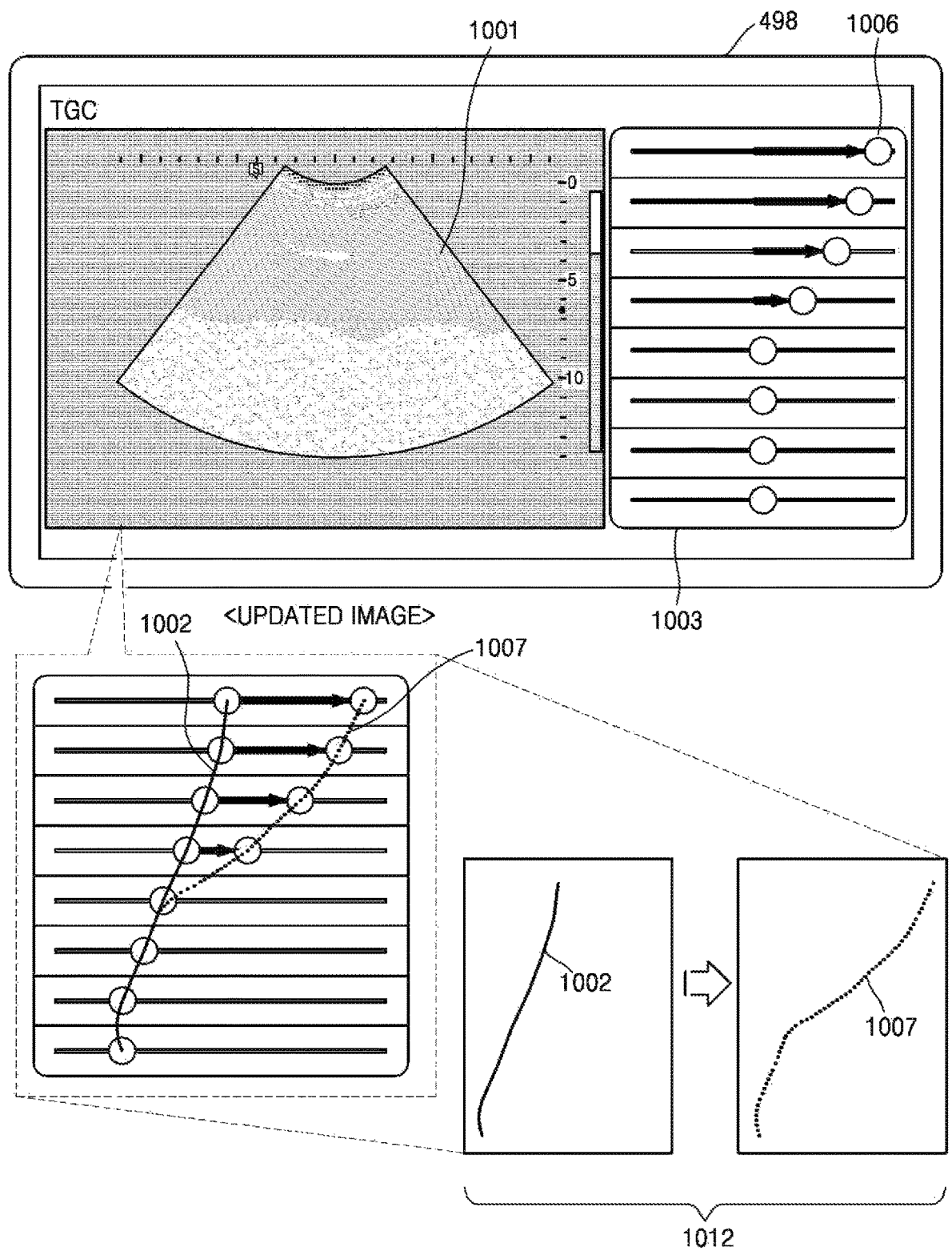

FIGS. 10A, 10B, and 10C are diagrams for describing the ultrasound apparatus 1000 updating an ultrasound image that is read from a storage medium based on a new TGC line that is input via a gain setting window.

Referring to FIG. 10A, the ultrasound apparatus 1000 may read an ultrasound image 1001 from a storage medium and display the ultrasound image 1001 in a first area. Along with the ultrasound image 1001, the ultrasound apparatus 1000 may read a first TGC value set 1002 (window 1008) and ultrasound echo signal data that correspond to the ultrasound image 1001.

The ultrasound apparatus 1000 may display, in a second area, a gain setting window 1003 for setting a TGC value according to a depth value. In this case, locations of adjustment buttons displayed in the gain setting window 1003 may be reset and the adjustment buttons may be aligned at the center positions of the slider bars.

Referring to FIG. 10B, the ultrasound apparatus 1000 may receive, via the gain setting window 1003, an input of adjusting at least one TGC value that corresponds to at least one depth value. For example, the ultrasound apparatus 1000 may receive an input 1005 of moving a first button 1010 rightward by 3 cm.

As shown in the window 1008, in the first TGC value set 1002, at first, the first button is located at the right of the center position. Thus, the user cannot move the first button rightward by 3 cm, but may only move the first button by 1 cm. That is, since the remaining 2 cm exceeds (reference numeral 1004) the gain setting window 1003, the user cannot move the first button by 3 cm. However, when the locations of the adjustment buttons in the gain setting window 1003 are reset, a TGC value adjustable range may be expanded.

Referring to FIG. 10C, the ultrasound apparatus 1000 may receive, via the gain setting window 1003, an input 1006 of modifying a first TGC value set 1002 to a second TGC value set 1007 (operation 1012). For example, the ultrasound apparatus 1000 may receive an input of moving a first button, a second button, a third button, and a fourth button in a rightward direction. In this case, TGC values, which correspond to depth values respectively indicated by the first to fourth buttons, may increase.

The ultrasound apparatus 1000 may update the ultrasound image by applying TGC values in the second TGC value set 1007 to the ultrasound echo signal data. For example, portions of the ultrasound image 1001 displayed in the first area, which correspond to the first to fourth buttons, may become brighter.

Figure 11:
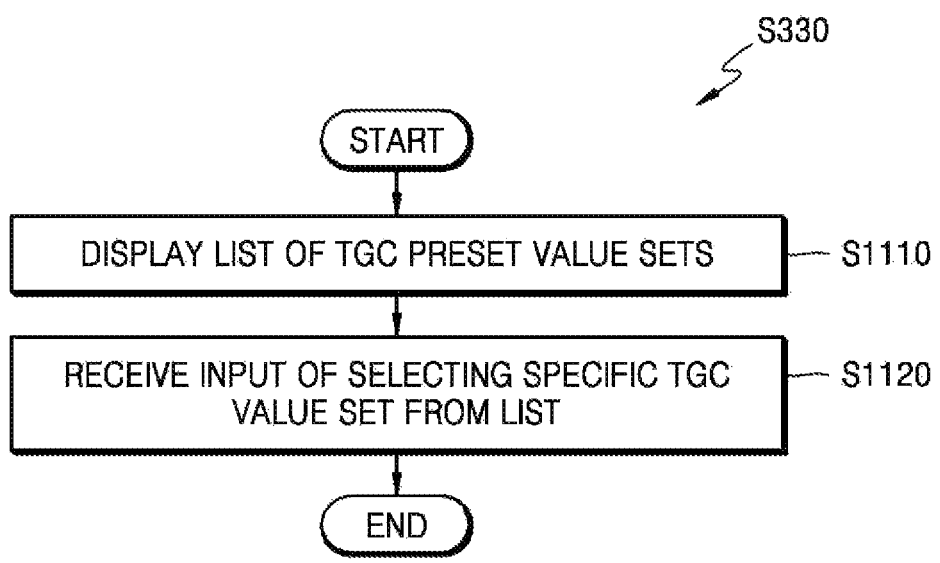
FIG. 11 is a flowchart of a method of modifying TGC information, according to an exemplary embodiment.

FIG. 11 is a flowchart of a method of modifying TGC information, according to an exemplary embodiment.

In operation S1110, the ultrasound apparatus 1000 may display a list of a plurality of TGC preset value sets. The TGC preset value sets may include a TGC value set that is predefined by the user.

According to an exemplary embodiment, the list of TGC preset value sets may include TGC line images that respectively represent the TGC preset value sets. Also, the list of TGC preset value sets may be displayed in text (e.g., numbers, characters, or indices) that represent the TGC preset value sets.

According to an exemplary embodiment, the ultrasound apparatus 1000 may display the list of TGC preset value sets in a portion of the screen or in a pop-up window.

According to an exemplary embodiment, the ultrasound apparatus 1000 may read at least one of the TGC preset value sets from a memory or a personal server (e.g., cloud server), and configure a list by using the at least read TGC preset value set. For example, the ultrasound apparatus 1000 may obtain the list of TGC preset value sets from an external storage medium or an internal storage medium.

According to an exemplary embodiment, the ultrasound apparatus 1000 may receive the list of TGC preset value sets from an external device via wired or wireless communication.

In operation S1120, the ultrasound apparatus 1000 may receive an input of selecting a certain TGC value set from the list of TGC preset value sets. For example, the ultrasound apparatus 1000 may detect a touch input (e.g., tap, double tap, touch and hold, swipe, or flick) or an audio command of the user related to an icon that represents the certain TGC value set. However, exemplary embodiments are not limited thereto.

Parameters other than TGC values may be preset. For example, the storage medium may store a list of preset LGC value sets, a list of preset reject levels, a list of preset dynamic ranges, a list of preset post-processing filters, etc.

Figure 12A:
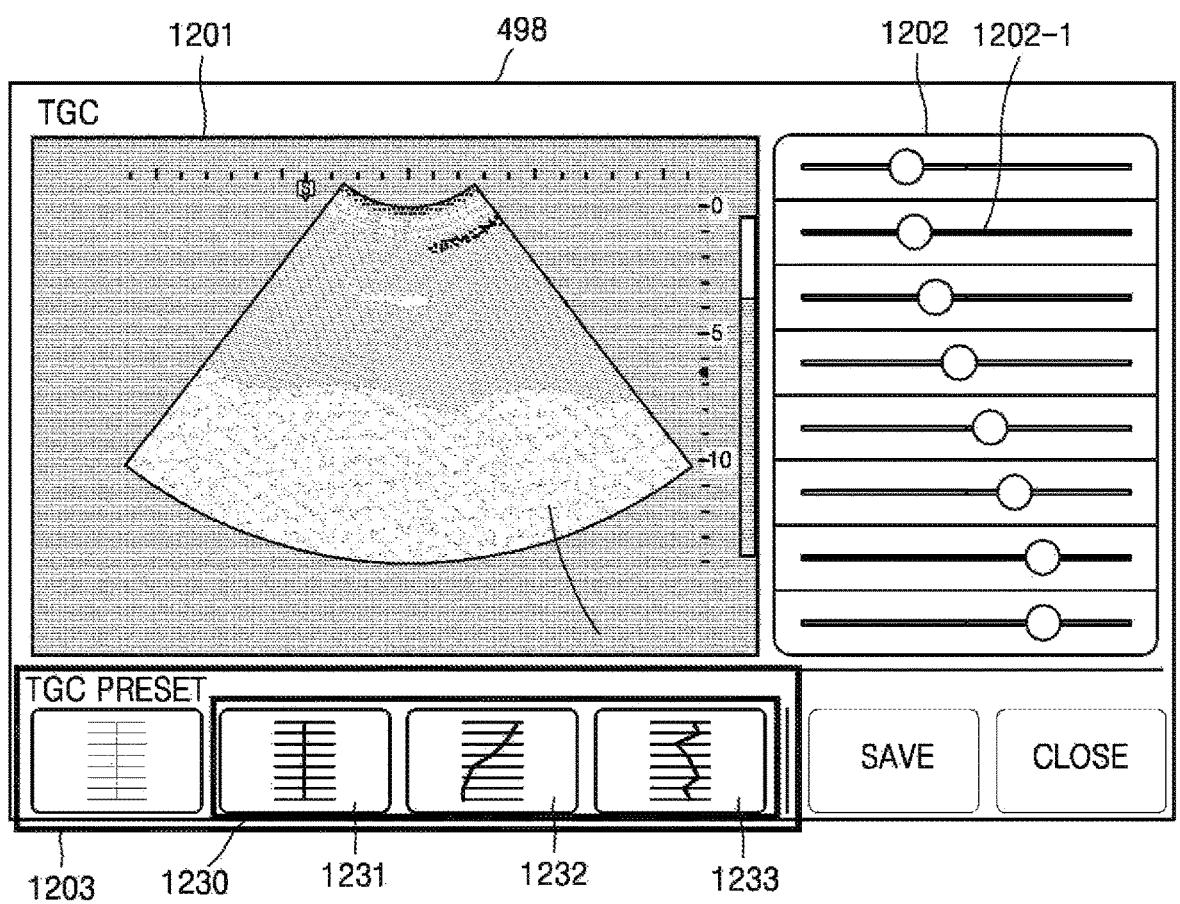
FIGS. 12A, 12B, and 12C are diagrams of examples of providing a list of prestored TGC values.
Figure 12B:
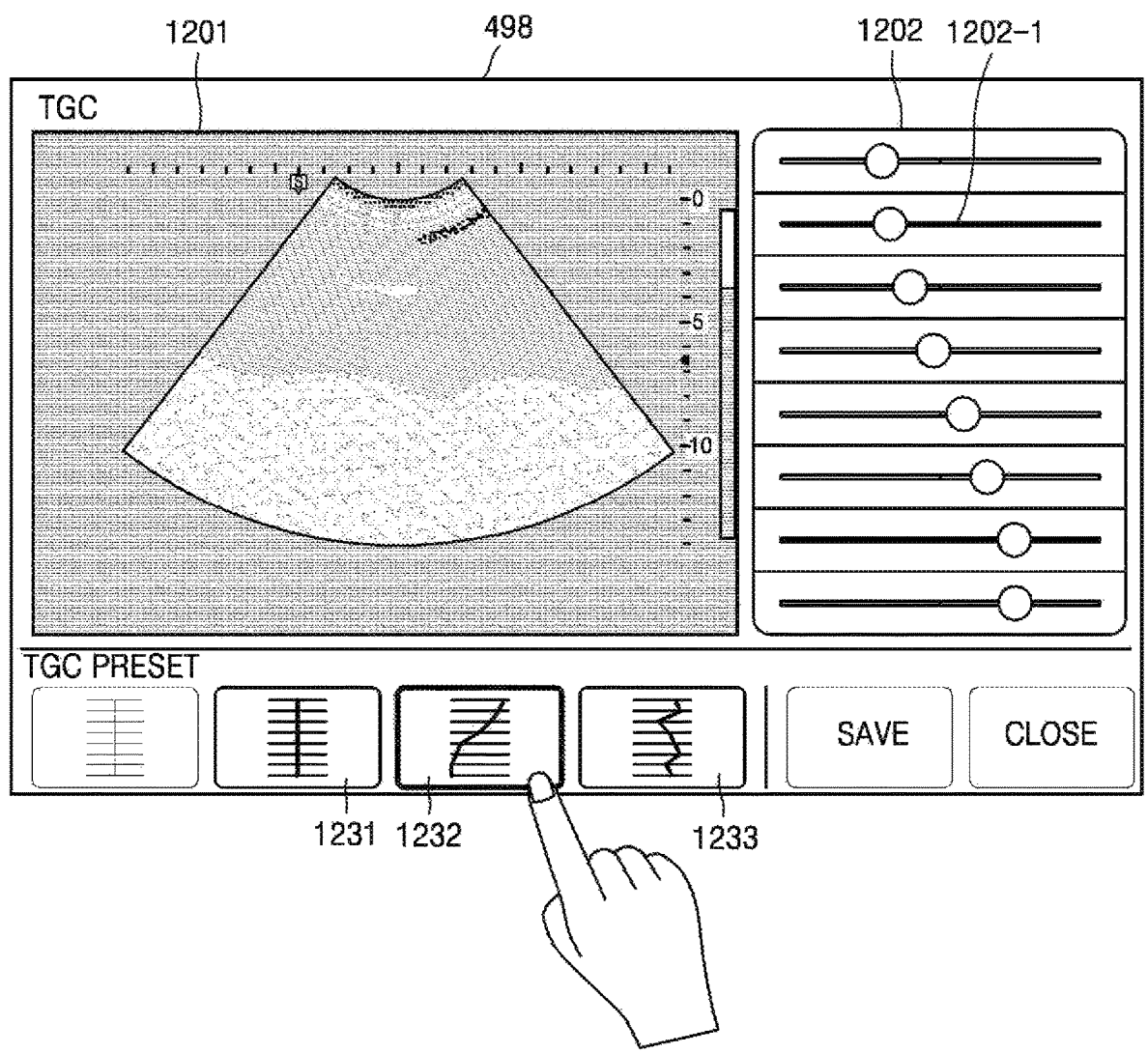
Figure 12C:
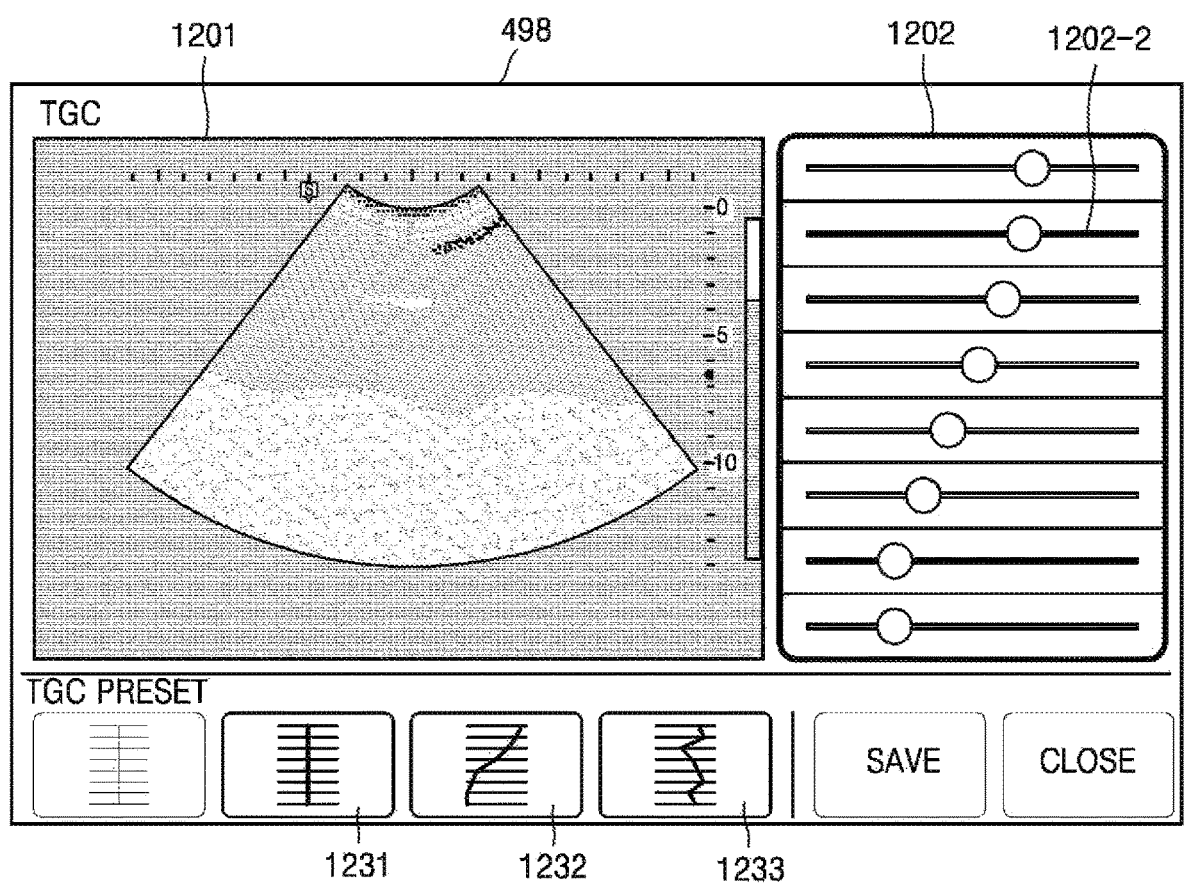

FIGS. 12A, 12B, and 12C are diagrams of examples of providing a list of prestored TGC values. Similarly, a list of prestored LGC values may be provided.

Referring to FIG. 12A, the ultrasound apparatus 1000 may display a prestored first ultrasound image in a first area 1201 of a screen, and display a first TGC value set 1202-1, which is matched to the first ultrasound image, in a second area 1202 of the screen.

The ultrasound apparatus 1000 may display a list of TGC preset value sets 1230 in a third area 1203 of the screen. According to an exemplary embodiment, the list of TGC preset value sets 1230 may be shown as images, e.g., icons or windows, including TGC lines that respectively correspond to TGC preset value sets. The TGC line may be shown in various ways, for example, a solid line, a dashed line, or a dot and dash line. The list of TGC preset value sets 1230 may be shown as an image including a plurality of slider bars with intersecting TGC lines. A point of each intersection corresponds to a TGC value at a respective depth in the ultrasound image.

For example, the list of TGC preset value sets 1230 may include a second icon 1231 that corresponds to a second TGC value set, a third icon 1232 that corresponds to a third TGC value set, and a fourth icon 1233 that corresponds to a fourth TGC value set.

Referring to FIG. 12B, the ultrasound apparatus 1000 may receive an input of selecting the third icon 1232 from the list of TGC preset value sets 1230. For example, the ultrasound apparatus 1000 may receive an input of touching the third icon 1232.

Referring to FIG. 12C, the ultrasound apparatus 1000 may display a third TGC value set 1202-2 that corresponds to the third icon 1232 selected by the user. Also, the ultrasound apparatus 1000 may update the first ultrasound image displayed on the first area by applying the third TGC value set 1202-2 to ultrasound echo signal data of the first ultrasound image. The brightness of the first ultrasound image may be modified in correspondence with values of the third TGC value set 1202-2.

According to an exemplary embodiment, the ultrasound apparatus 1000 may receive, from the user, an additional input of adjusting at least one TGC value in the third TGC value set 1202-2. That is, the user may adjust TGC values by entirely or partially modifying the third TGC value set 1202-2 in the second area 1202.

According to an exemplary embodiment, the ultrasound apparatus 1000 may provide some samples of TGC preset value sets so that the user may conveniently set TGC values.

Figure 13A:
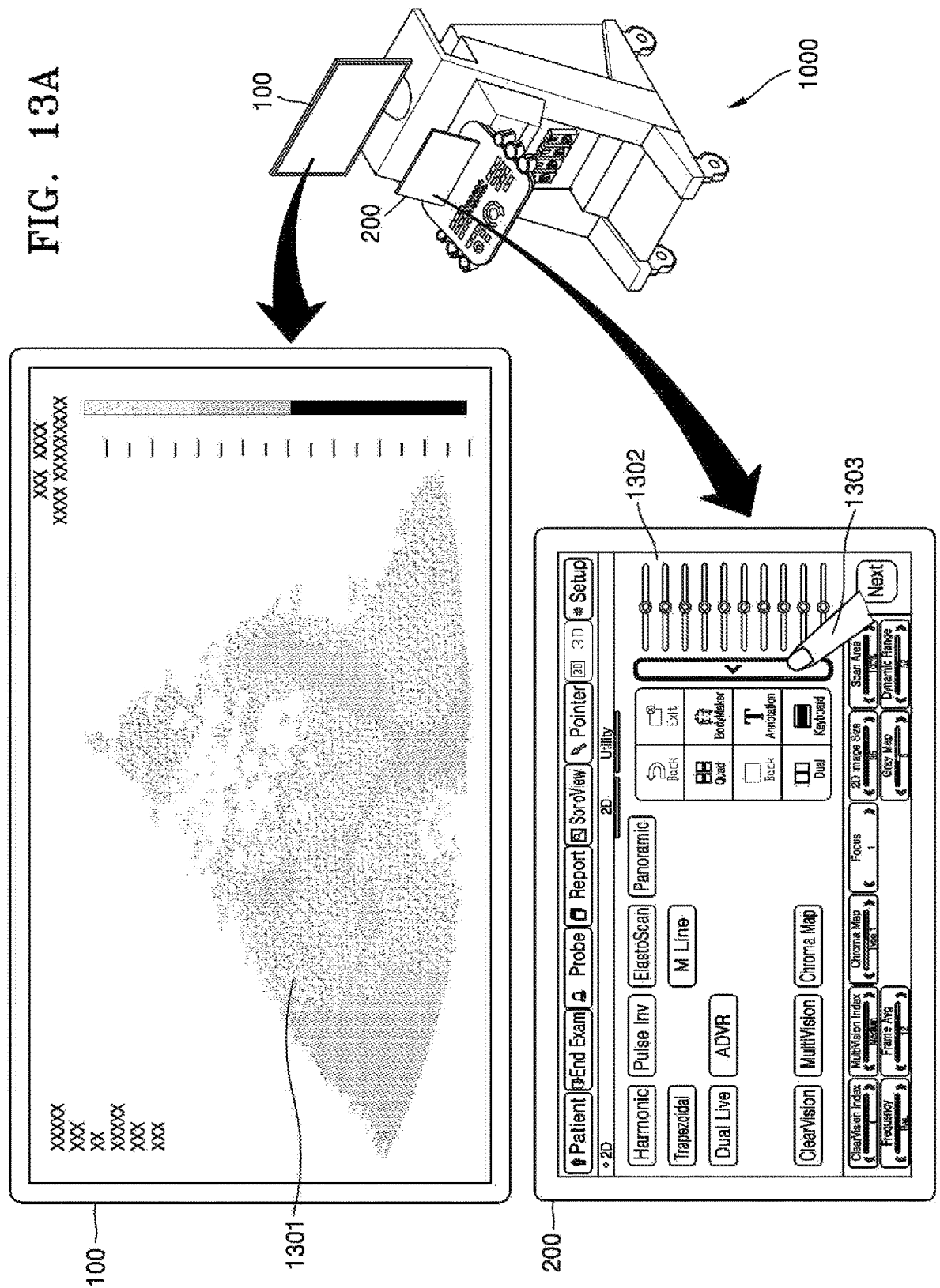
FIGS. 13A, 13B, and 13C are diagrams of examples for providing a list of prestored TGC values on a control panel, separately from a main screen displaying an ultrasound image.
Figure 13B:
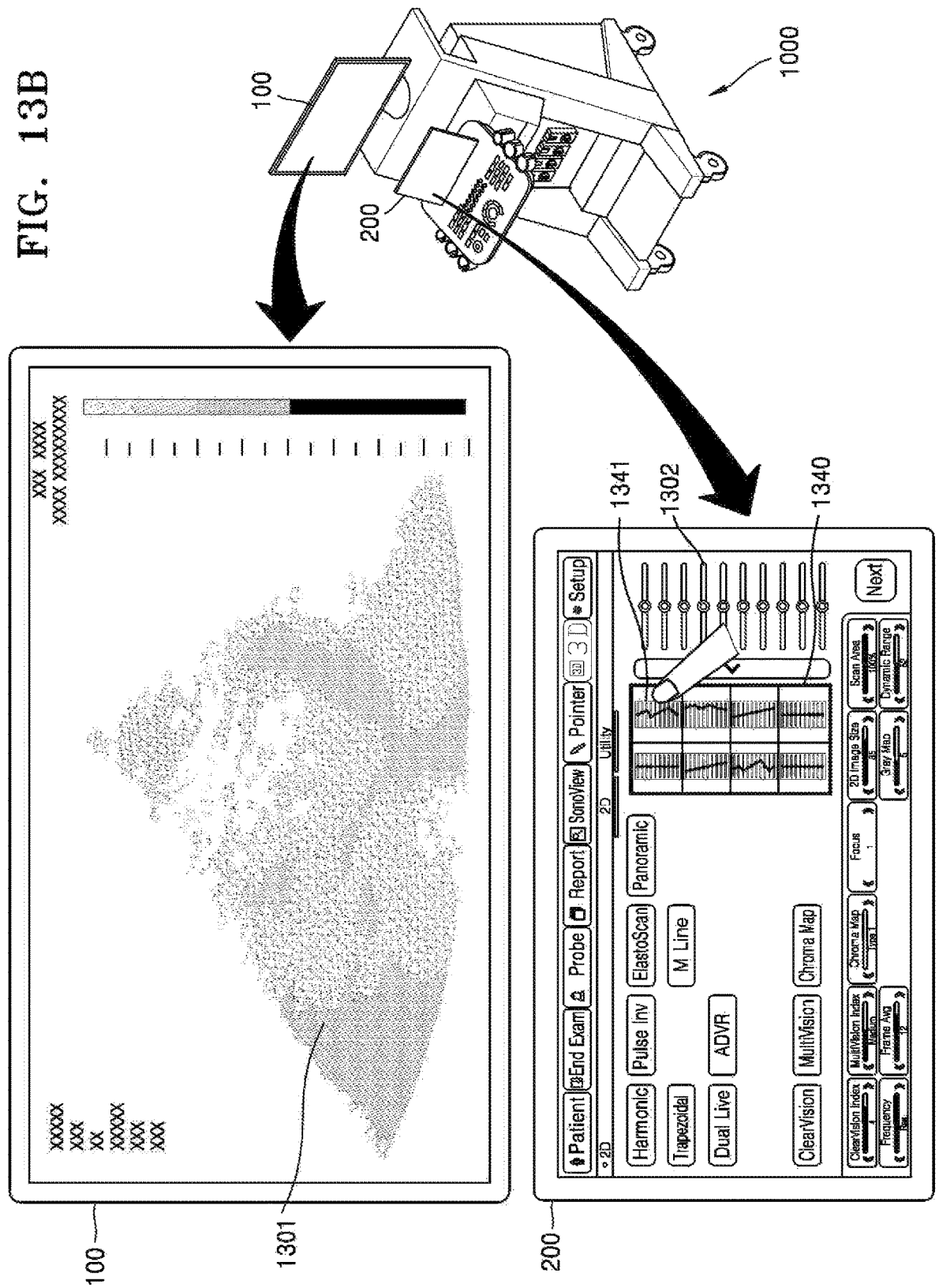
Figure 13C:
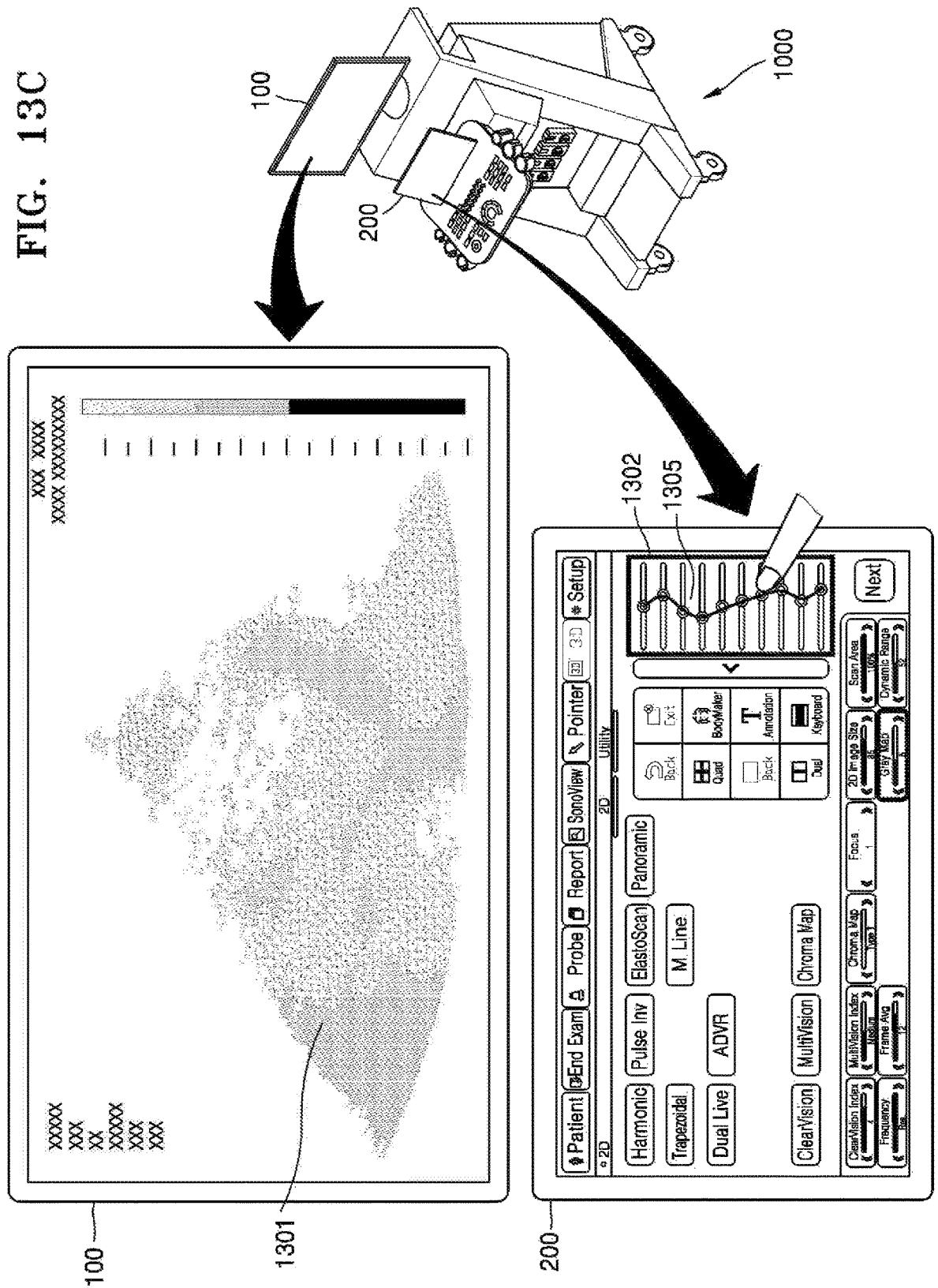

FIGS. 13A, 13B, and 13C are diagrams of examples for providing a list of prestored TGC values on a control panel, separately from a main screen displaying an ultrasound image. Similarly, a list of prestored LGC values may be provided separately from a main screen displaying an ultrasound image.

Referring to FIG. 13A, the ultrasound apparatus 1000 may read a first ultrasound image 1301 from a storage medium and display the first ultrasound image 1301 on the display 100. Also, the ultrasound apparatus 1000 may display, on the control panel 200, TGC information that is matched to the first ultrasound image 1301. For example, the ultrasound apparatus 1000 may display a first TGC value set, which is matched to the first ultrasound image 1301, on a plurality of slider bars 1302 on the control panel 200.

The ultrasound apparatus 1000 may receive a gesture of touching a preset button 1303 for a predetermined time or more.

Referring to FIG. 13B, in response to the gesture of touching the preset button 1303, the ultrasound apparatus 1000 may display a list 1340 of TGC preset value sets on the control panel 200. The list 1340 may include icons that respectively correspond to the TGC preset value sets.

According to an exemplary embodiment, the ultrasound apparatus 1000 may receive an input of selecting one TGC value set from the list 1340. For example, the ultrasound apparatus 1000 may receive an input of touching an icon 1341 that represents a second TGC value set.

Referring to FIG. 13C, in response to the input of touching the icon 1341, the ultrasound apparatus 1000 may read a second TGC value set 1305 from the storage medium (e.g., a memory, an external storage medium, or a cloud server). Also, the ultrasound apparatus 1000 may display the second TGC value set 1305 on the slider bars 1302. For example, locations of adjustment buttons on the slider bars 1302 may vary according to TGC values that correspond to depth values in the second TGC value set 1305.

Also, the ultrasound apparatus 1000 may update the first ultrasound image 1301 by applying the second TGC value set 1305 to ultrasound echo signal data of the first ultrasound image 1301. In this case, brightness of depth areas of the first ultrasound image 1301 may vary.

Figure 13D:
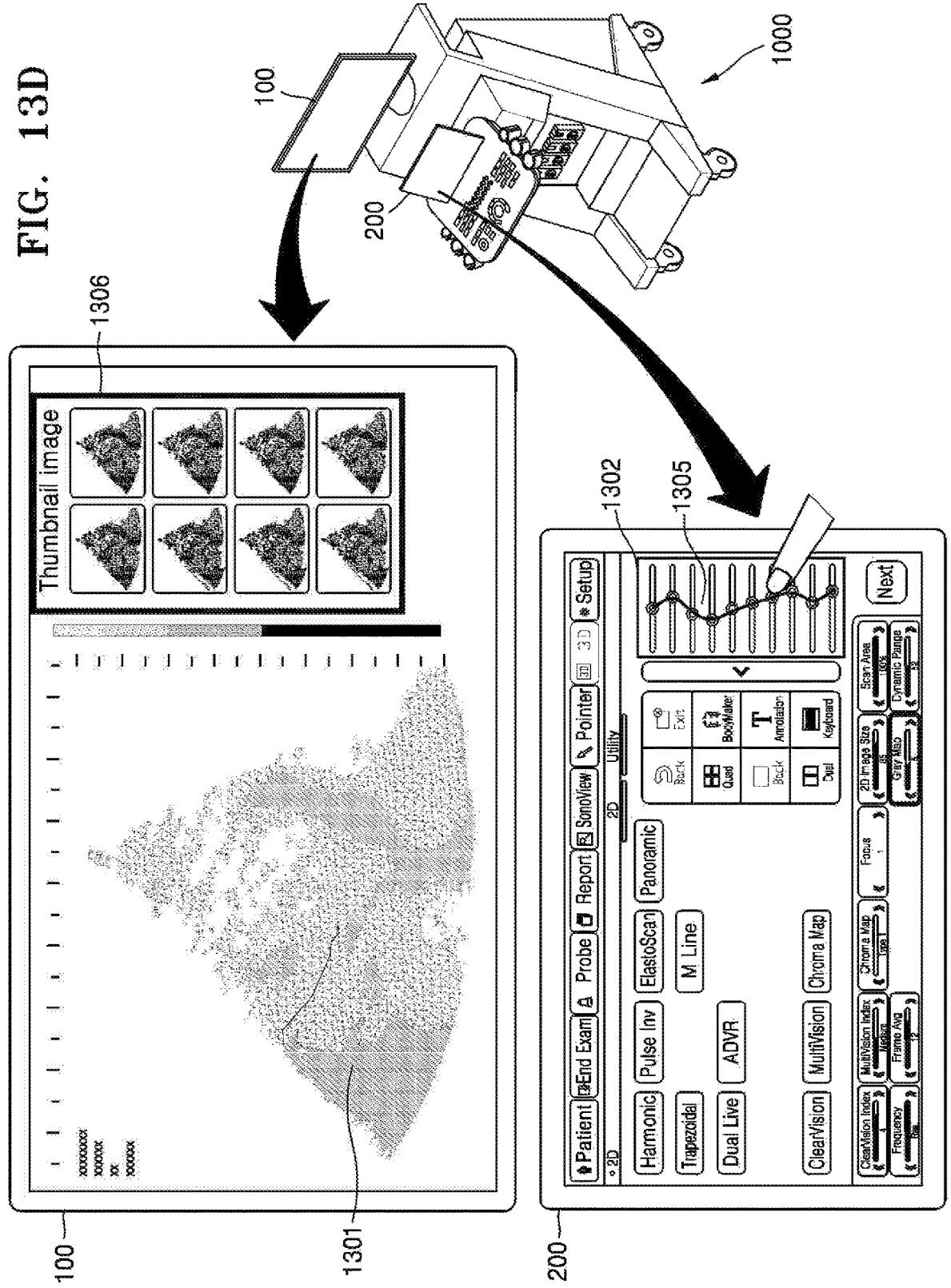
FIG. 13D is a diagram of ultrasound images that correspond to a selected prestored TGC value set.

FIG. 13D is a diagram of ultrasound images that correspond to a selected prestored TGC value set.

Referring to FIG. 13D, the ultrasound apparatus 1000 may display a list 1306 of ultrasound images that correspond to the second TGC value set 1305. For example, when a second ultrasound image, a third ultrasound image, and a fourth ultrasound image are matched to the second TGC value set 1305, the ultrasound apparatus 1000 may display respective thumbnail images of the second to fourth ultrasound images on a portion of the display 100. In this case, the user may simultaneously identify the ultrasound images generated by using the second TGC value set 1305.

Figure 14:
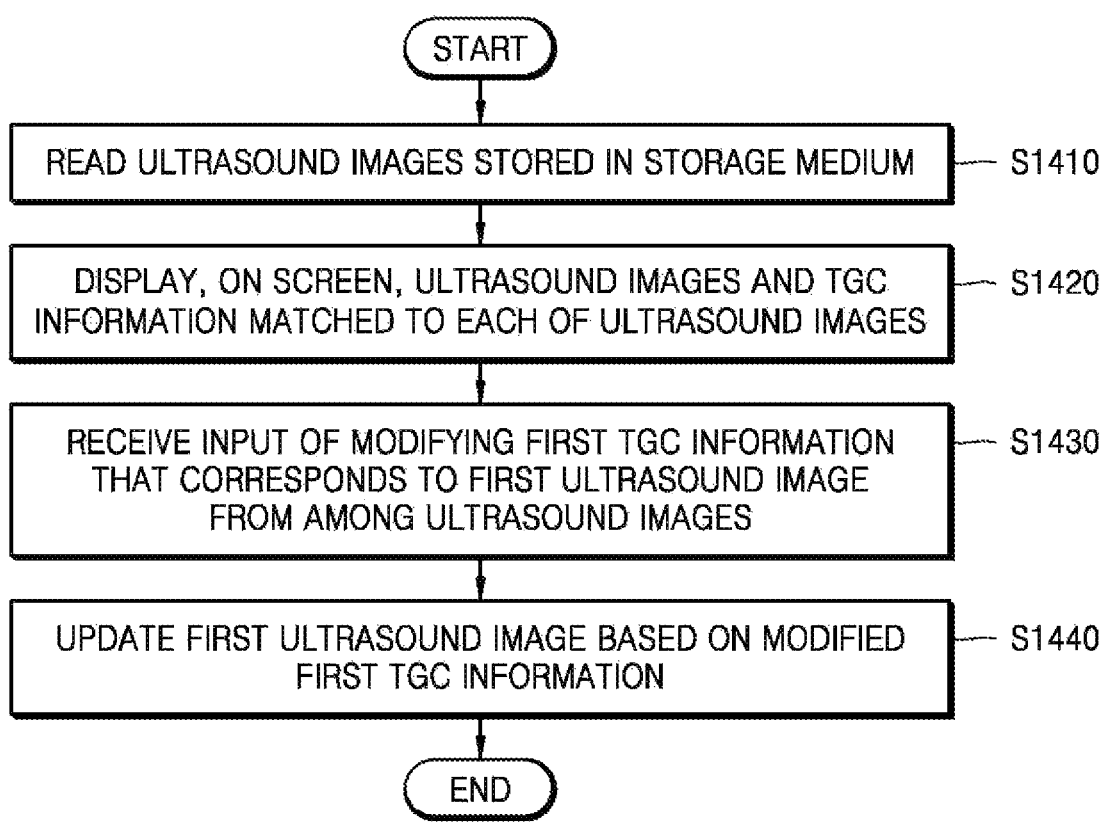
FIG. 14 is a flowchart of a method of providing TGC information that is matched to each of ultrasound images, according to an exemplary embodiment.

FIG. 14 is a flowchart of a method of providing TGC information that is matched to each of ultrasound images, according to an exemplary embodiment.

In operation S1410, the ultrasound apparatus 1000 may read a plurality of ultrasound images that are stored in a storage medium.

For example, the ultrasound apparatus 1000 may receive an input of selecting ultrasound images from a list of ultrasound images stored in the storage medium. In this case, the ultrasound apparatus 1000 may read, from the storage medium, the ultrasound images selected by the user. Also, the ultrasound apparatus 1000 may read TGC information corresponding to each of the ultrasound images and ultrasound echo signal data corresponding to each of the ultrasound images.

In operation S1420, the ultrasound apparatus 1000 may display, on a screen, the ultrasound images and the TGC information matched to each of the ultrasound image.

For example, a first ultrasound image and first TGC information corresponding to the first ultrasound image may be displayed in a first area, a second ultrasound image and second TGC information corresponding to the second ultrasound image may be displayed in a second area, and a third ultrasound image and third TGC information corresponding to the third ultrasound image may be displayed in a third area. The user may simultaneously identify the TGC information that corresponds to each of the prestored ultrasound image.

In operation S1430, the ultrasound apparatus 1000 may receive an input of modifying the first TGC information of the first ultrasound image among the ultrasound images. For example, the ultrasound apparatus 1000 may receive an input of adjusting at least one TGC value that corresponds to at least one depth value in the first TGC information.

According to an exemplary embodiment, the ultrasound apparatus 1000 may receive an input of adjusting locations of adjustment buttons on a plurality of slider bars. Also, according to an exemplary embodiment, the ultrasound apparatus 1000 may receive an input of modifying a first TGC value set to a second TGC value set, via a first TGC line corresponding to the first TGC information. Also, the ultrasound apparatus 1000 may receive an input of dragging in a depth axis direction within a predetermined area (e.g., gain setting area) displaying the first TGC line. According to an exemplary embodiment, the ultrasound apparatus 1000 may receive an input of selecting one TGC preset value set from a list of TGC preset value sets.

In operation S1440, the ultrasound apparatus 1000 may update the first ultrasound image according to the modified first TGC information. For example, the ultrasound apparatus 1000 may apply at least one TGC value in the modified first TGC information to first ultrasound echo signal data of the first ultrasound image. In this case, brightness of the entire or a portion of the first ultrasound image may be modified.

According to an exemplary embodiment, the ultrasound apparatus 1000 may receive an input of modifying the second TGC information corresponding to the second ultrasound image among the ultrasound images, and update the second ultrasound image according to the modified second TGC information.

In this case, the user may compare the ultrasound images or compare the TGC information corresponding to the ultrasound images.

Figure 15:
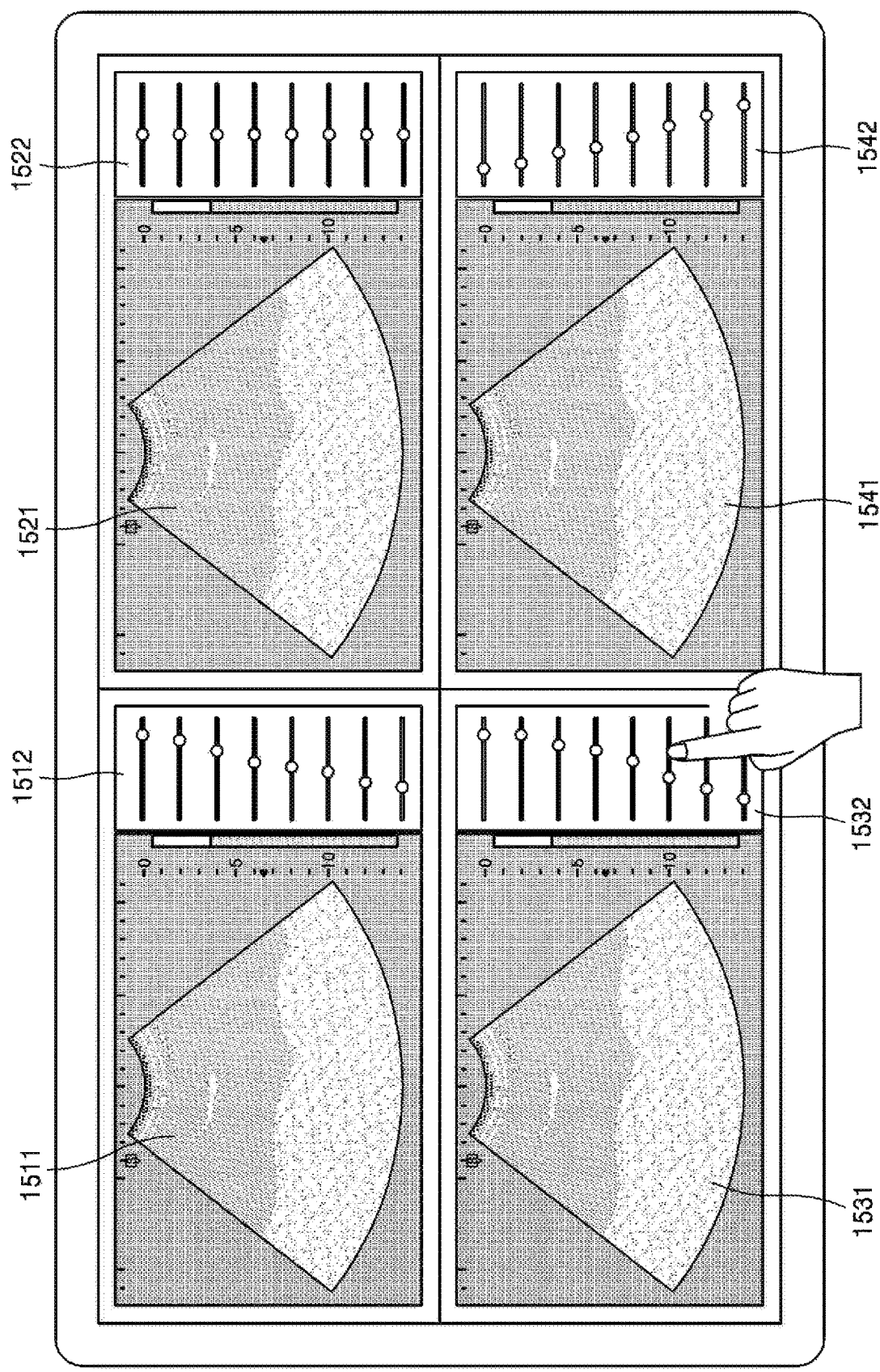
FIG. 15 is a diagram of TGC information that corresponds to each of ultrasound images.

FIG. 15 is a diagram of TGC information that corresponds to each of ultrasound images.

Referring to FIG. 15, the ultrasound apparatus 1000 may receive a user's input of selecting a first ultrasound image 1511, a second ultrasound image 1521, a third ultrasound image 1531, and a fourth ultrasound image 1541, which are stored in the storage medium. For example, a user may select the first to fourth ultrasound images from the displayed thumbnail images, as described above and shown in FIG. 5A.

In response to the user's input, the ultrasound apparatus 1000 may read the first to fourth ultrasound images 1511, 1521, 1531, and 1541 from the storage medium and display the first to fourth ultrasound images 1511, 1521, 1531, and 1541 on a screen.

Also, the ultrasound apparatus 1000 may display first TGC information 1512, which corresponds to the first ultrasound image 1511, at one side of the first ultrasound image 1511; second TGC information 1522, which corresponds to the second ultrasound image 1521, at one side of the second ultrasound image 1521; third TGC information 1532, which corresponds to the third ultrasound image 1531, at one side of the third ultrasound image 1531; and fourth TGC information 1542, which corresponds to the fourth ultrasound image 1541, at one side of the fourth ultrasound image 1541.

In this case, the user may modify at least one of the first TGC information 1512, the second TGC information 1522, the third TGC information 1532, and the fourth TGC information 1542 to adjust brightness of at least one of the first to fourth ultrasound images 1511, 1521, 1531, and 1541. For example, the ultrasound apparatus 1000 may receive an input of modifying the third TGC information 1532, and update the third ultrasound image 1531 by applying the modified third TGC information 1532 to ultrasound echo signal data of the third ultrasound image 1531.

Figure 16:
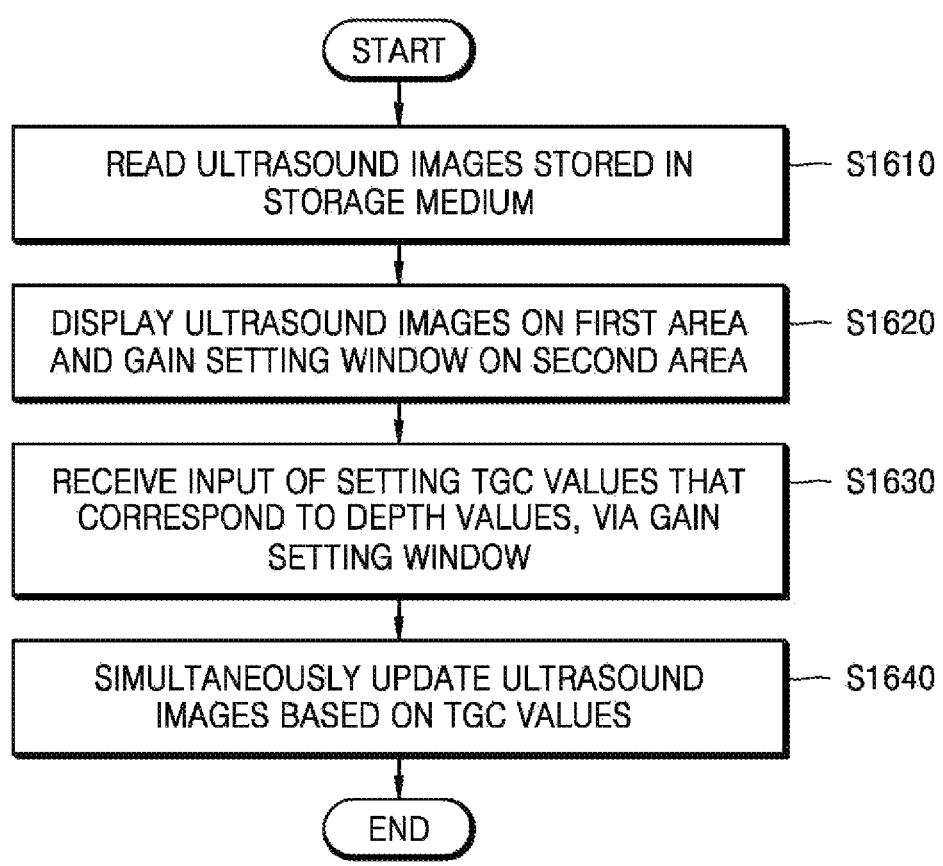
FIG. 16 is a flowchart of a method of simultaneously updating ultrasound images based on TGC values that correspond to depth values that are set via a gain setting window, according to an exemplary embodiment.

FIG. 16 is a flowchart of a method of simultaneously updating ultrasound images based on TGC values that correspond to depth values that are set via a gain setting window, according to an exemplary embodiment.

In operation S1610, the ultrasound apparatus 1000 may read a plurality of ultrasound images from the storage medium.

For example, the ultrasound apparatus 1000 may receive an input of selecting the ultrasound images from a list of ultrasound images stored in the storage medium. In this case, the ultrasound apparatus 1000 may read the ultrasound images selected by the user from the storage medium. Also, the ultrasound apparatus 1000 may read TGC information and ultrasound echo signal data that correspond to each of the ultrasound images.

In operation S1620, the ultrasound apparatus 1000 may display the ultrasound images on a first area, and display a gain setting window on a second area.

For example, when a first ultrasound image, a second ultrasound image, and a third ultrasound image are selected by the user, the ultrasound apparatus 1000 may display the first to third ultrasound images on the first area, and display the gain setting window for adjusting TGC values, which correspond to depth values, on the second area.

According to an exemplary embodiment, the first and second areas may be in a single screen or separate screens. For example, when the first and second areas are in the control panel 200, the ultrasound apparatus 1000 may display the ultrasound images and the gain setting window in the control panel 200. Alternatively, when the first area is in the display 100 and the second area is in the control panel 200, the ultrasound apparatus 1000 may display the ultrasound images in the display 100 and display the gain setting window in the control panel 200.

In operation S1630, the ultrasound apparatus 1000 may receive an input of setting the TGC values, which correspond to the depth values, via the gain setting window.

The ultrasound apparatus 1000 may receive an input of moving adjustment buttons on a plurality of slider bars included in the gain setting window. For example, the ultrasound apparatus 1000 may receive an input of dragging an adjustment button on the slider bar or tapping a location on the slider bar to adjust the TGC value. Also, when the user draws and drags a line or a curve which is drawn through the buttons of the slider bars in a direction perpendicular to the slider bars, the ultrasound apparatus 1000 may determine TGC values with respect to dragged locations and set the determined TGC values as TGC values corresponding to the depth values.

According to an exemplary embodiment, the ultrasound apparatus 1000 may receive an input of modifying a first TGC value set to a second TGC value set, via a vertical reference line which is drawn through the buttons of the slider bars in a direction in which the slider bars are arranged. For example, the vertical reference line may be a straight line or a curved line which curves along the direction in which the slider bars are arranged. For example, the ultrasound apparatus 1000 may receive an input of touching a point on the vertical reference line and dragging the touched point leftward or rightward. If the user touches the point on the vertical reference line and drags the touched point rightward, a TGC value corresponding to a depth value at the point may increase.

Also, ultrasound apparatus 1000 may receive a drag input in a depth axis direction within a portion of the gain setting window that does not include the slider bars. In this case, new TGC values may be set based on a location of the drag input.

According to an exemplary embodiment, the ultrasound apparatus 1000 may receive an input of selecting one TGC value set from a list of TGC preset value sets.

In operation S1640, the ultrasound apparatus 1000 may simultaneously update the ultrasound images according to the TGC values that correspond to the depth values set via the gain setting window.

For example, the ultrasound images may be simultaneously updated by applying the TGC values set via the gain setting window on ultrasound echo signal data that corresponds to each of the ultrasound images.

An operation of the ultrasound apparatus 1000 simultaneously updating the ultrasound images will be described below with reference to FIG. 17.

Figure 17:
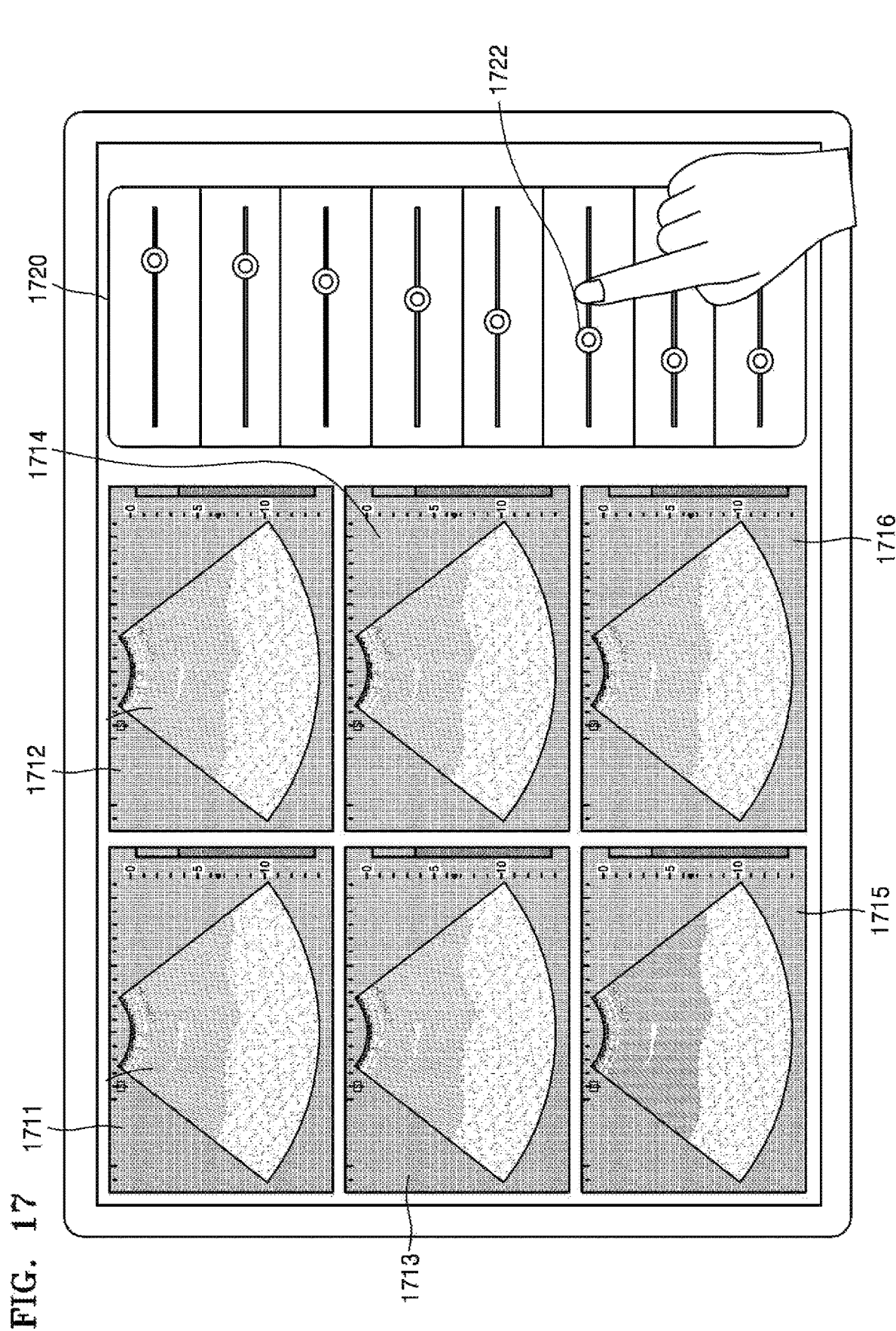
FIG. 17 is a diagram for describing an example of simultaneously updating ultrasound images based on TGC values that correspond to depth values that are set via a gain setting window.

FIG. 17 is a diagram for describing an example of simultaneously updating ultrasound images based on TGC values that correspond to depth values that are set via a gain setting window.

Referring to FIG. 17, the ultrasound apparatus 1000 may receive a user's input of selecting a first ultrasound image 1711, a second ultrasound image 1712, a third ultrasound image 1713, a fourth ultrasound image 1714, a fifth ultrasound image 1715, and a sixth ultrasound image 1716, which are stored in the storage medium.

In response to the user's input, the ultrasound apparatus 1000 may read the first to sixth ultrasound images 1711 to 1716 from the storage medium and display the first to sixth ultrasound images 1711 to 1716 in a first area of the screen.

Also, the ultrasound apparatus 1000 may display, in a second area, a gain setting window 1720 for adjusting TGC values corresponding to depth values in each of the first to sixth ultrasound images 1711 to 1716. According to an exemplary embodiment, locations of adjustment buttons displayed in the gain setting window 1720 may be reset and aligned at the center. The ultrasound apparatus 1000 may receive an input of adjusting at least one TGC value corresponding to at least one depth value, via the gain setting window 1720.

For example, the ultrasound apparatus 1000 may receive an input of moving a first button rightward by 3 cm. In this case, a TGC value of a depth value that corresponds to the first button 1722 may increase in each of the first to sixth ultrasound images 1711 to 1716. Therefore, an image of a depth corresponding to the first button in each of the first to sixth ultrasound images 1711 to 1716 may become brighter.

Also, the ultrasound apparatus 1000 may receive an input of selecting an icon corresponding to a first TGC value set from a user. For example, a user may select the icon from the displayed list of preset TGC values, as described above with reference to FIGS. 11 to 12C. In this case, the ultrasound apparatus 1000 may simultaneously adjust brightness of the first to sixth ultrasound images 1711 to 1716 by applying the first TGC value set to ultrasound echo signal data of each of the first to sixth ultrasound images 1711 to 1716.

Figure 18:
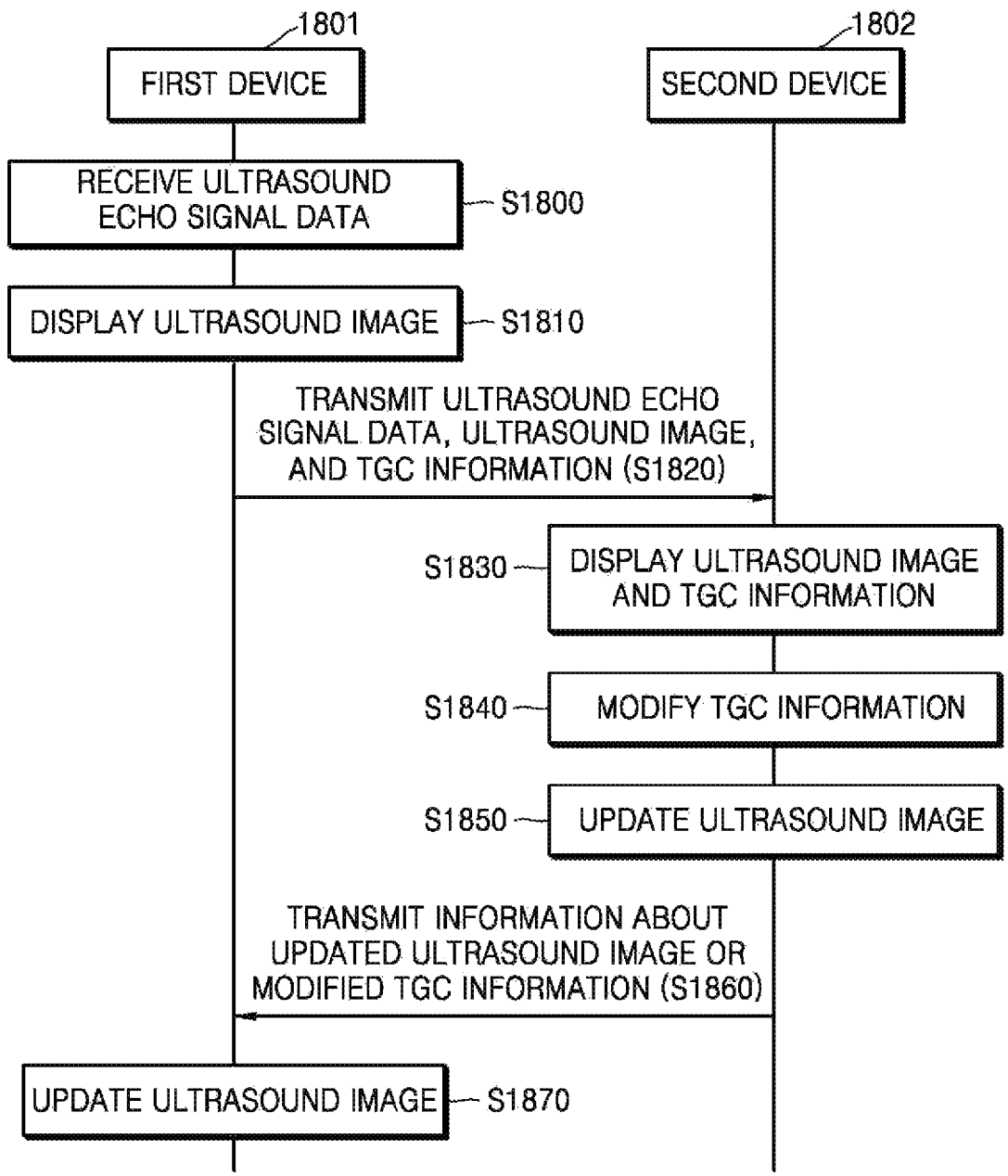
FIG. 18 is a flowchart of a method of updating an ultrasound image received from an external device by modifying TGC information that corresponds to the received ultrasound image.

FIG. 18 is a flowchart of a method of obtaining and updating an ultrasound image received by external devices, i.e., the devices disposed distally to one another and/or connected via a network.

In operation S1800, a first device 1801 may obtain ultrasound echo signal data.

According to an exemplary embodiment, the first device 1801 may obtain ultrasound echo signal data of an object. For example, the first device 1801 may send an ultrasound signal to the object, and generate the ultrasound echo signal data based on an ultrasound echo signal received from the object.

In operation S1810, the first device 1801 may display an ultrasound image based on the ultrasound echo signal data.

According to an exemplary embodiment, the ultrasound image may be at least one of, but is not limited to, a B mode image, a C mode image, a D mode image, and an elastic mode image.

In operation S1820, the first device 1801 may transmit the ultrasound echo signal data, the ultrasound image, and TGC information to a second device 1802. For example, the first device 1801 may transmit an ultrasound image correction request to the second device 1802.

According to an exemplary embodiment, the first device 1801 may transmit the ultrasound echo signal data, the ultrasound image, and the TGC information to the second device 1802 via short distance communication (e.g., Bluetooth, Wi-Fi, etc.).

According to an exemplary embodiment, the first device 1801 may transmit the ultrasound echo signal data, the ultrasound image, and the TGC information to the second device 1802 directly or via a server.

In operation S1830, the second device 1802 may display the ultrasound image and the TGC information.

According to an exemplary embodiment, the second device 1802 may display the ultrasound image and the TGC information matched to the ultrasound image on a single screen or separate screens.

In operation S1840, the second device 1802 may receive an input for modifying the TGC information. For example, the second device 1802 may receive an input of adjusting at least one TGC value in the TGC information which corresponds to at least one depth value.

In operation S1850, the second device 1802 may update the ultrasound image displayed on the second device 1802.

According to an exemplary embodiment, when the TGC information is modified, the second device 1802 may apply at least one modified TGC value to ultrasound echo signal data of the ultrasound image displayed on the screen. In this case, brightness of a portion of or the entire ultrasound image may be modified. For example, as the user increases a TGC value corresponding to a first depth value, the ultrasound image may become brighter at the first depth value. As the user decreases a TGC value corresponding to a second depth value, the ultrasound image may become darker at the second depth value.

Operations S1830 to S1850 correspond to operations S320 to S340 of FIG. 3, and thus, detailed description will be omitted herein.

In operation S1860, the second device 1802 may transmit information related to the updated ultrasound image or modified TGC information to the first device 1801.

According to an exemplary embodiment, the second device 1802 may transmit the information related to the updated ultrasound image or the modified TGC information to the first device 1801 via short distance communication (e.g., Bluetooth, Wi-Fi, etc.).

In operation S1870, the first device 1801 may update the ultrasound image.

For example, when the first device 1801 receives the information about the updated ultrasound image from the second device 1802, the first device 1801 may display, on a screen of the first device 1801, the ultrasound image that is updated by the second device 1802 based on the information about the updated ultrasound image.

Also, when the first device 1801 receives the modified TGC information from the second device 1802, the first device 1801 may update the ultrasound image displayed on the first device 1801 by applying the modified TGC information to ultrasound echo signal data of the ultrasound image displayed on the first device 1801.

According to an exemplary embodiment, some of the operations S1800 to S1870 may be omitted or be performed in a different order.

Hereinafter, an example in which the first device 1801 is a mobile ultrasound apparatus and the second device 1802 is an ultrasound apparatus of a medical facility will be described with reference to FIG. 19.

Figure 19:
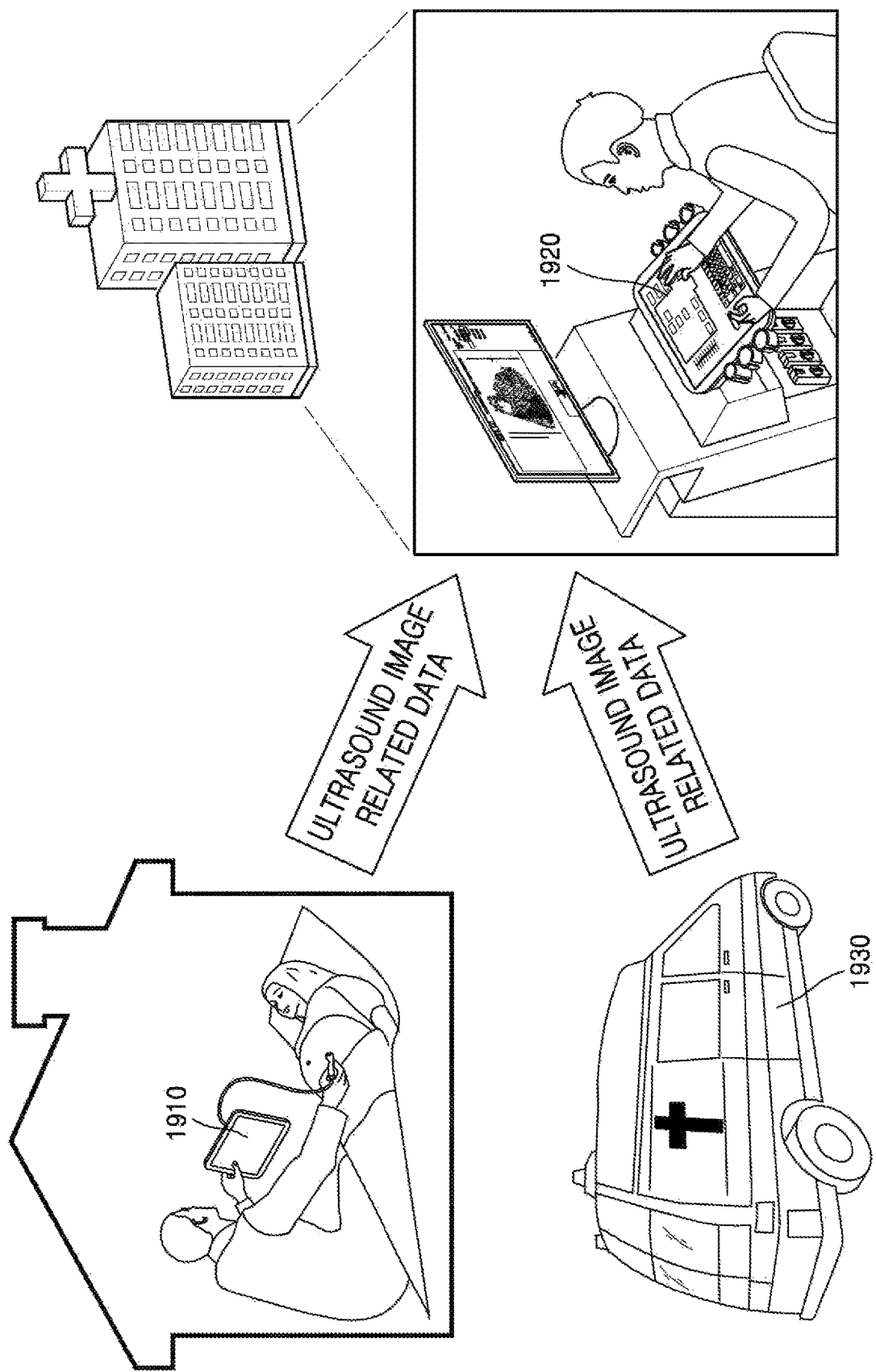
FIG. 19 is a diagram for describing an example of an ultrasound apparatus remotely receiving ultrasound image related data from an external source.

FIG. 19 is a diagram for describing an example of an ultrasound apparatus remotely receiving ultrasound image related data from an external source.

According to an exemplary embodiment, a first user may obtain an ultrasound image of a diagnosis target by using a first mobile ultrasound apparatus 1910 at home. The first mobile ultrasound apparatus 1910 may transmit acquired ultrasound image related data to an ultrasound apparatus 1920 of a medical facility. For example, the first mobile ultrasound apparatus 1910 may transmit the ultrasound image, ultrasound echo signal data, and TGC information to the ultrasound apparatus 1920.

According to an exemplary embodiment, the first mobile ultrasound apparatus 1910 may transmit the ultrasound image related data to the ultrasound apparatus 1920 via a server of a hospital.

A medical doctor may identify the ultrasound image of the diagnosis target from the first mobile ultrasound apparatus 1910 via the ultrasound apparatus 1920, and increase sensitivity of the ultrasound image by modifying TGC information matched to the ultrasound image. Also, the medical doctor may detect lesion by analyzing the ultrasound image of the diagnosis target received from the first mobile ultrasound apparatus 1910.

Also, according to an exemplary embodiment, a second user may obtain the ultrasound image of the diagnosis target by using a second mobile ultrasound apparatus 1930 in an ambulance. The second mobile ultrasound apparatus 1930 may transmit acquired ultrasound image related data to the ultrasound apparatus 1920. For example, the second mobile ultrasound apparatus 1930 may transmit the ultrasound image, ultrasound echo signal data, and TGC information to the ultrasound apparatus 1920.

The medical doctor may identify the ultrasound image of the diagnosis target from the second mobile ultrasound apparatus 1930 via the ultrasound apparatus 1920, and obtain an ultrasound image with desired sensitivity by modifying TGC information matched to the ultrasound image. In this case, the medical doctor may identify status of the diagnosis target before the ambulance arrives to the hospital by analyzing the ultrasound image of the diagnosis target received from the second mobile ultrasound apparatus 1930.

Therefore, according to an exemplary embodiment, the diagnosis target may remotely receive an ultrasound examination without going to a hospital.

Figure 20:
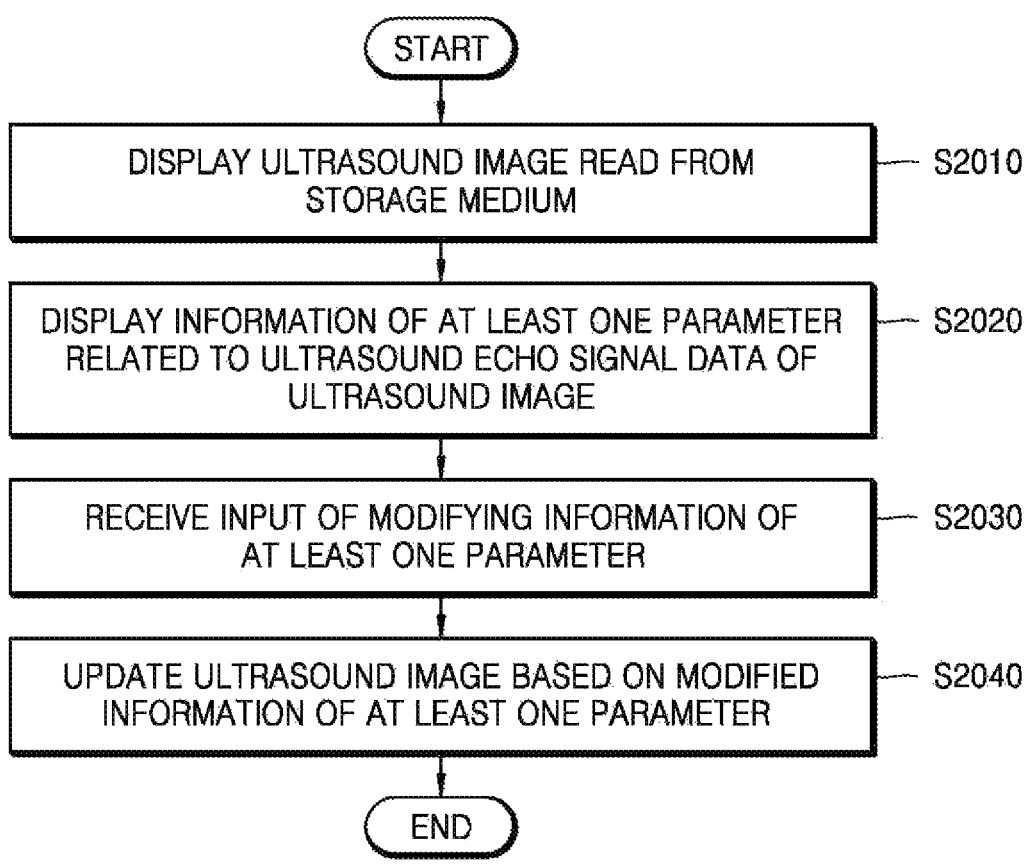
FIG. 20 is a flowchart of a method of updating an ultrasound image by modifying information of at least one parameter related to ultrasound echo signal data of a pre-stored ultrasound image, according to an exemplary embodiment.

FIG. 20 is a flowchart of a method of updating an ultrasound image by modifying information of at least one parameter related to ultrasound echo signal data of a pre-stored ultrasound image, according to an exemplary embodiment.

In operation S2010, the ultrasound apparatus 1000 may read an ultrasound image from the storage medium and display the ultrasound image. Since operation S2010 correspond to operations S310 and S320 of FIG. 3, detailed description thereof will be omitted.

In operation S2020, the ultrasound apparatus 1000 may display information of at least one parameter related to ultrasound echo signal data of an ultrasound image.

According to an exemplary embodiment, a parameter related to the ultrasound echo signal data refers to a parameter that may be applied to the ultrasound echo signal data to compensate for sensitivity of the ultrasound image. Examples of the parameter may include, but is not limited to, TGC, LGC, a reject level, a dynamic range, and a post-processing filter.

According to an exemplary embodiment, the ultrasound apparatus 1000 may display the ultrasound image and the information of at least one parameter on a single screen or separate screens.

In operation S2030, the ultrasound apparatus 1000 may receive an input of modifying the information of at least one parameter.

For example, the ultrasound apparatus 1000 may receive the input of modifying information of at least one parameter among TGC, LGC, a reject level, a dynamic range, and a post-processing filter. However, exemplary embodiments are not limited thereto.

According to an exemplary embodiment, the input of modifying information of at least one parameter may include, but is not limited to, a touch input, an audio input, a key input, and a bending input.

In operation S2040, the ultrasound apparatus 1000 may update the ultrasound image based on the modified information of at least one parameter.

For example, the ultrasound apparatus 1000 may compensate for sensitivity of the ultrasound image by applying the modified information of at least one parameter to ultrasound echo signal data of the ultrasound image.

The operation of the ultrasound apparatus 1000 updating the ultrasound image based on the modified information of at least one parameter will be further described below with reference to FIGS. 21A to 21C.

Figure 21A:
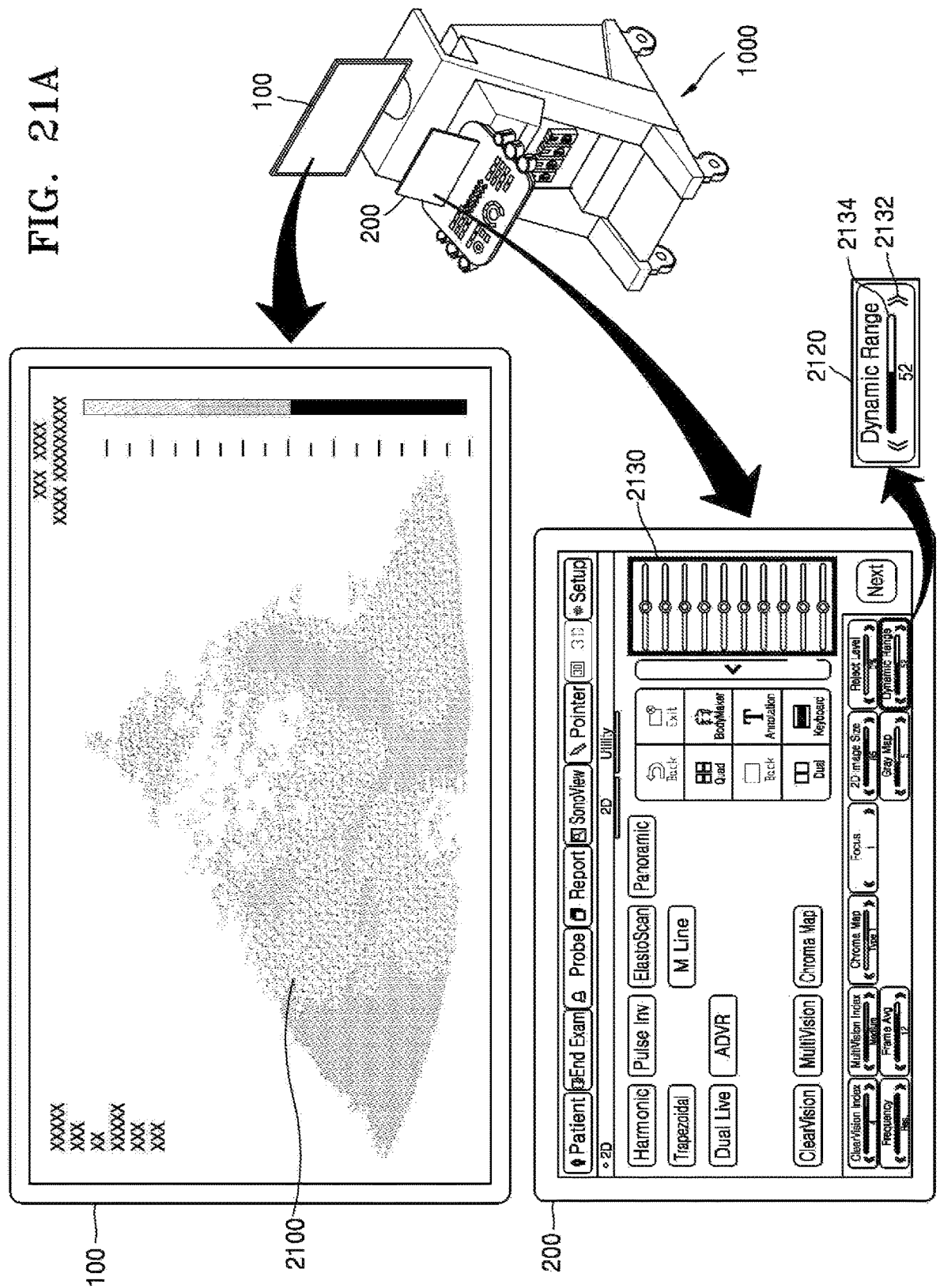
FIG. 21A is a diagram for describing an example of adjusting a dynamic range.
Figure 21B:
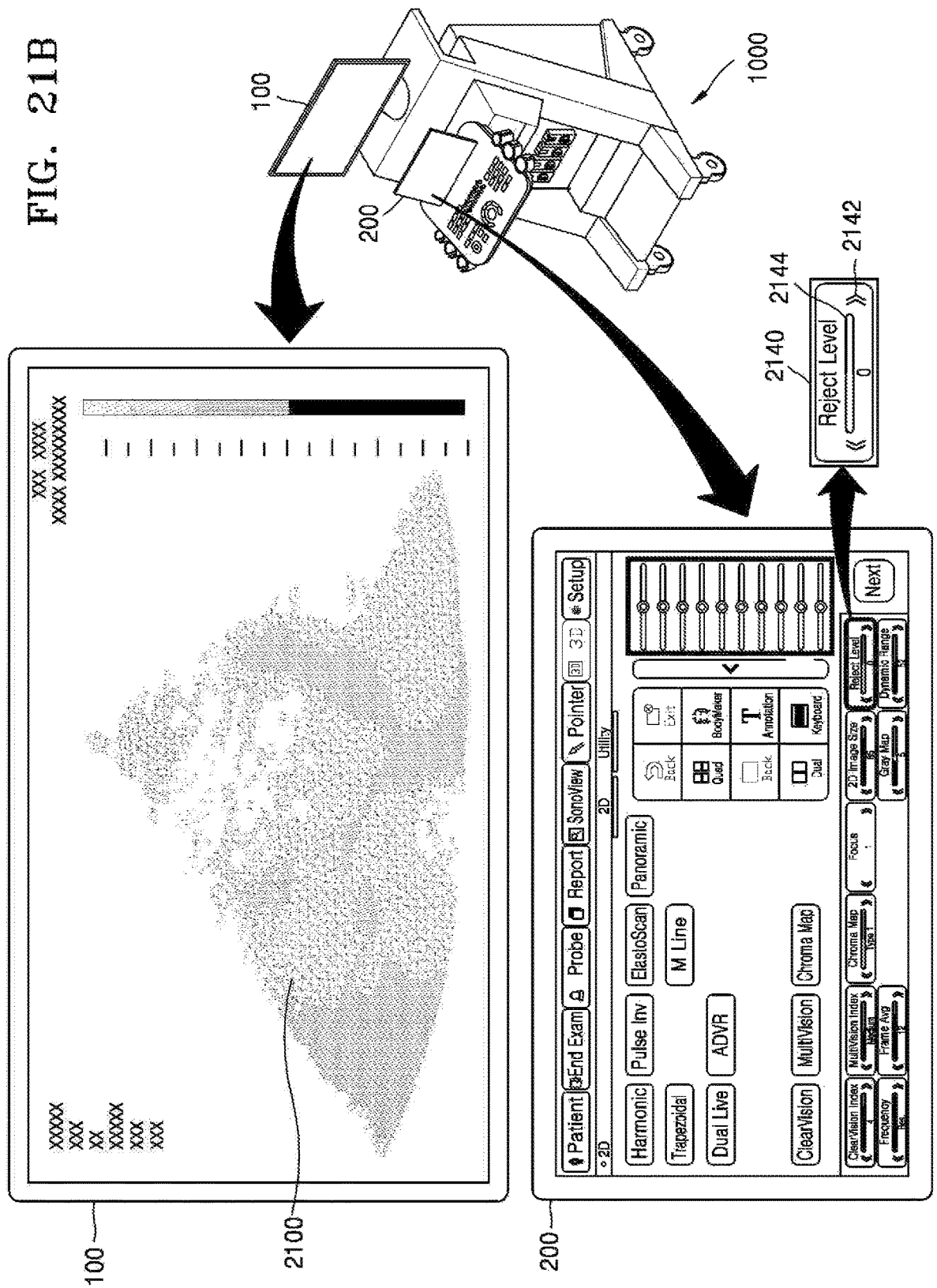
FIG. 21B is a diagram for describing an example of adjusting a reject level.
Figure 21C:
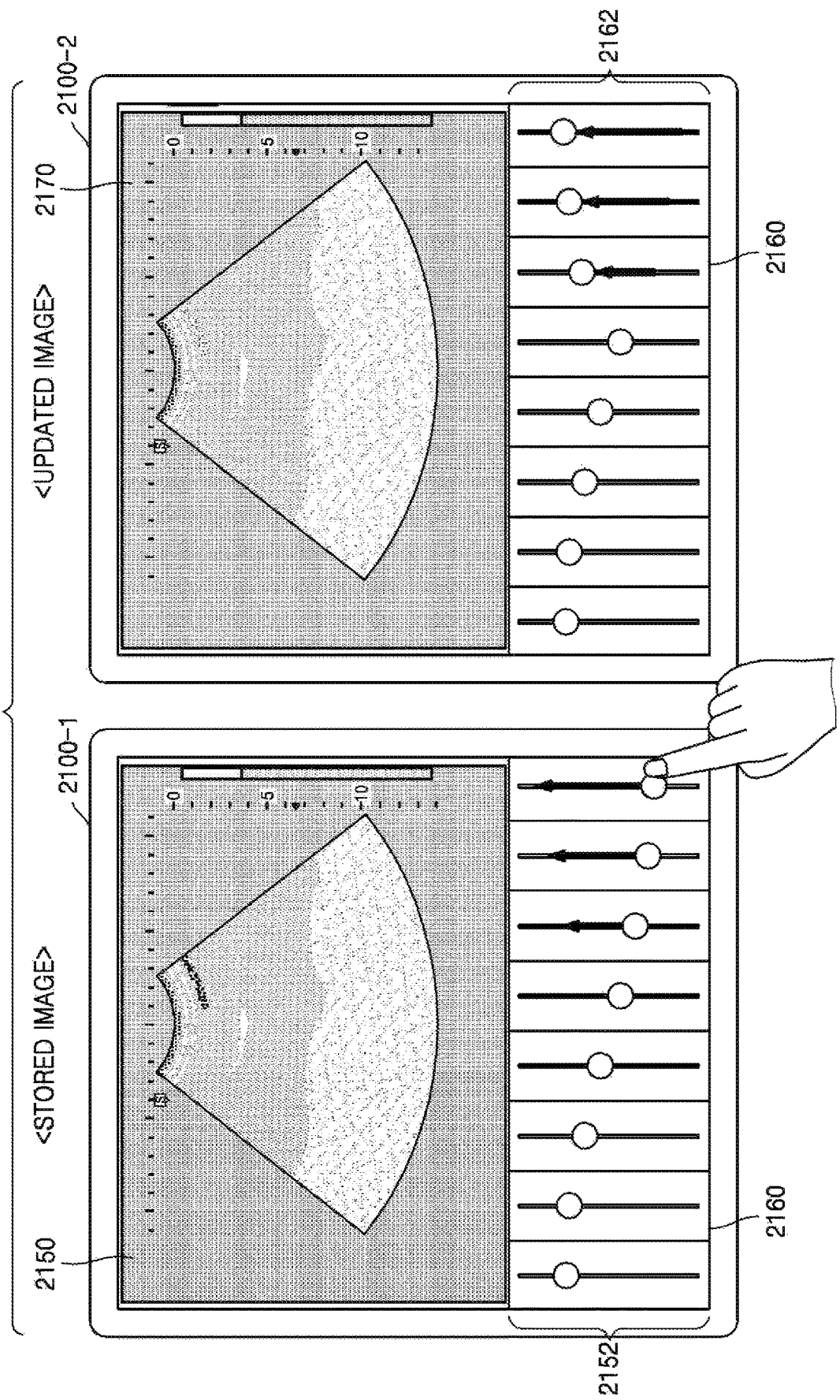
FIG. 21C is a diagram for describing an example of adjusting a lateral gain compensation (LGC) value.

FIG. 21A is a diagram for describing an example of adjusting a dynamic range, FIG. 21B is a diagram for describing an example of adjusting a reject level, and FIG. 21C is a diagram for describing an example of adjusting an LGC value.

Referring to FIG. 21A, the ultrasound apparatus 1000 may read a first ultrasound image 2100 from the storage medium and display the first ultrasound image 2100 on the display 100. Also, the ultrasound apparatus 1000 may display TGC information that is matched to the first ultrasound image 2100, on the control panel 200. For example, the ultrasound apparatus 1000 may display a first TGC value set that is matched to the first ultrasound image 2100 on a plurality of slider bars 2130 of the control panel 200.

Also, the ultrasound apparatus 1000 may display dynamic range information that is matched to the first ultrasound image 2100, on the control panel 200. For example, the ultrasound apparatus 1000 may display a dynamic range value that is matched to the first ultrasound image 2100, on a 'Dynamic Range' icon 2120 of the control panel 200.

The dynamic range is a parameter for adjusting brightness by modifying a ratio between the minimum and the maximum of an input signal. For example, the user may select one from 50 to 200 to set the dynamic range value.

According to an exemplary embodiment, the ultrasound apparatus 1000 may receive an input of modifying the dynamic range value via the 'Dynamic Range' icon 2120. For example, the ultrasound apparatus 1000 may receive an input of touching left and/or right direction keys 2132 of the 'Dynamic Range' icon 2120 or an input of dragging a scale 2134 in the 'Dynamic Range' icon 2120.

Then, the ultrasound apparatus 1000 may update the first ultrasound image 2100 by applying the modified dynamic range value to ultrasound echo signal data of the first ultrasound image 2100.

Referring to FIG. 21B, the ultrasound apparatus 1000 may display reject level information that is matched to the first ultrasound image 2100, on the control panel 200. For example, the ultrasound apparatus 1000 may display a reject level value that is matched to the first ultrasound image 2100 on a 'Reject Level' icon 2140 of the control panel 200.

The reject level is a parameter for removing noise of the ultrasound image. For example, the user may select one from 1 to 64 to set the reject level value.

According to an exemplary embodiment, the ultrasound apparatus 1000 may receive an input of modifying the reject level value via the 'Reject Level' icon 2140. For example, the ultrasound apparatus 1000 may receive an input of touching left and/or right direction keys 2142 of the 'Reject Level' icon 2140 or an input of dragging a scale 2144 inside the 'Reject Level' icon 2140.

Then, the ultrasound apparatus 1000 may update the first ultrasound image 2100 by applying the modified reject level value to ultrasound echo signal data of the first ultrasound image 2100.

Referring to a screen 2100-1 of FIG. 21C, the ultrasound apparatus 1000 may read a second ultrasound image 2150 from the storage medium and display the second ultrasound image 2150 on a first area of a screen. Also, the ultrasound apparatus 1000 may display LGC information that is matched to the second ultrasound image 2150 on a second area 2160 of the screen. For example, the ultrasound apparatus 1000 may display a first LGC value set 2152 that is matched to the second ultrasound image 2150, in the second area 2160.

According to an exemplary embodiment, the ultrasound apparatus 1000 may receive an input of modifying the LGC information in the second area 2160. For example, the ultrasound apparatus 1000 may receive an input of modifying the first LGC value set to a second LGC value set 2162.

Referring to a screen 2100-2 of FIG. 21C, the ultrasound apparatus 1000 may update the second ultrasound image 2150 by applying the second LGC value set to second ultrasound echo signal data of the second ultrasound image 2150, and display an updated second ultrasound image 2170.

Figure 22:
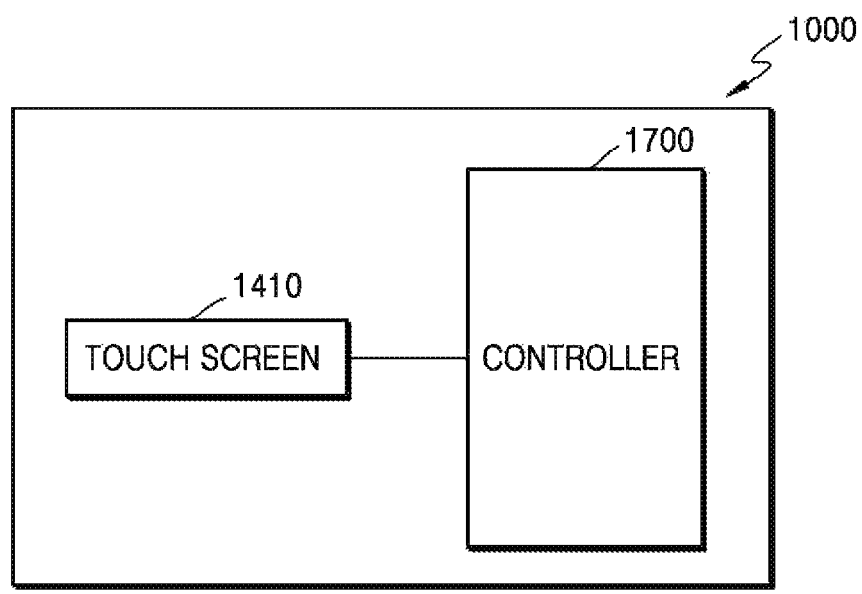
FIGS. 22 and 23 are block diagrams of an ultrasound apparatus, according to an exemplary embodiment.
Figure 23:
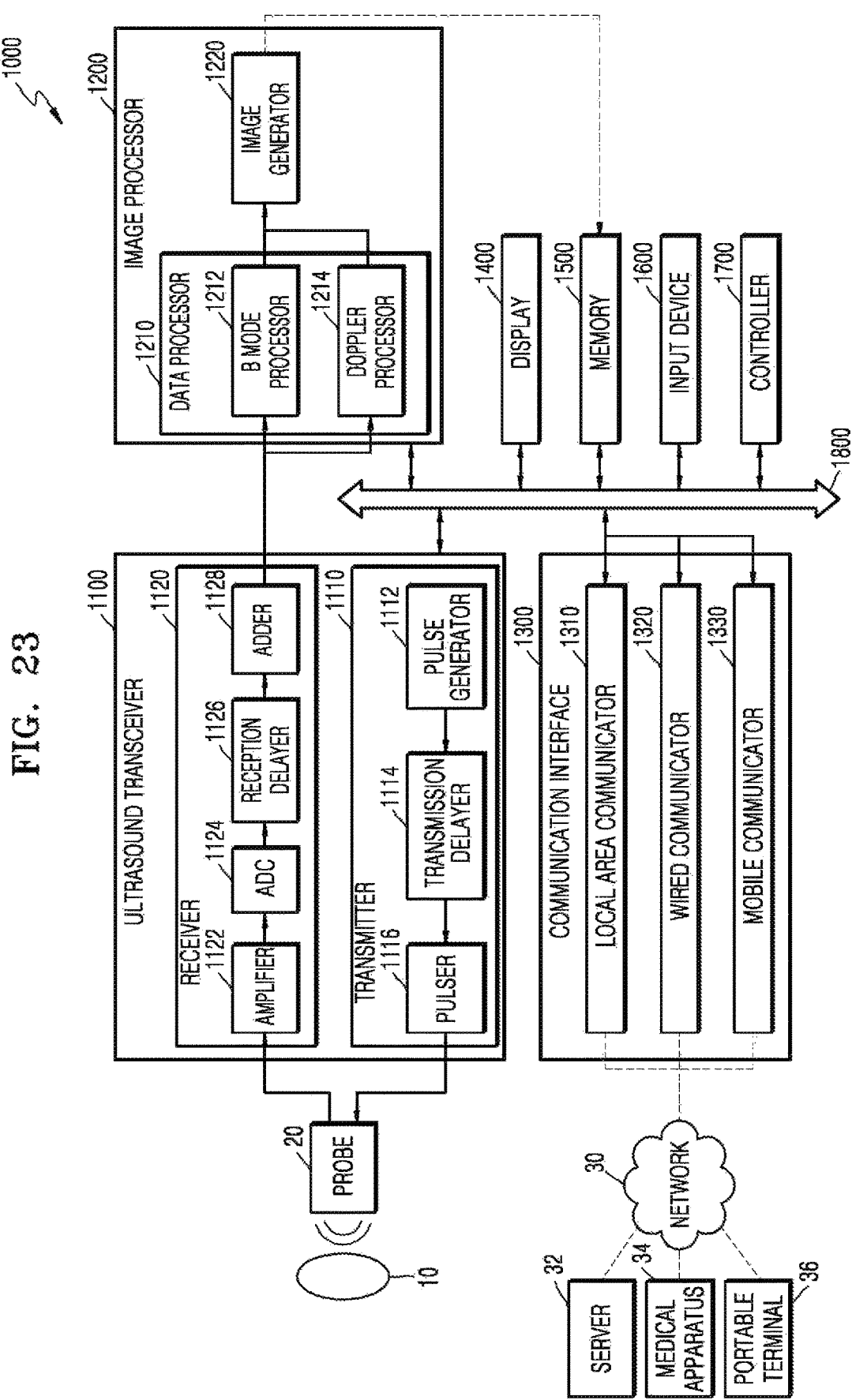

FIGS. 22 and 23 are block diagrams of an ultrasound apparatus, according to an exemplary embodiment.

Referring to FIG. 22, the ultrasound apparatus 1000 according to an exemplary embodiment may include a touch screen 1410 and a controller 1700. The touch screen 1410 may be included in a display (100 or 1400). However, not all of the illustrated components are necessarily required. More or less components may be included to configure the ultrasound apparatus 1000.

For example, as shown in FIG. 23, the ultrasound diagnostic apparatus 1000 may include a probe 20, an ultrasound transceiver 1100, an image processor 1200, a communication interface 1300, a display or displays 1400, a memory 1500, an input device 1600, and a controller 1700, which may be connected to one another via buses 1800.

The ultrasound apparatus 1000 may be a cart type apparatus or a portable type apparatus. Examples of portable ultrasound diagnostic apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillates in response to electrical signals and generates acoustic energy, that is, ultrasound waves. Furthermore, the probe 20 may be connected to the main body 22 of the ultrasound apparatus 1000 by wire or wirelessly, and according to exemplary embodiments, the ultrasound apparatus 1000 may include a plurality of probes 20.

A transmitter 1110 supplies a driving signal to the probe 20. The transmitter 1110 includes a pulse generator 1112, a transmission delayer 1114, and a pulser 1116. The pulse generator 1112 generates pulses for forming transmission ultrasound waves based on a predetermined pulse repetition frequency (PRF), and the transmission delayer 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delayer 1126, and an adder 1128. The amplifier 1122 amplifies echo signals in each transducer channel, and the ADC 1124 performs analog-to-digital conversion with respect to the amplified echo signals. The reception delayer 1126 delays digital echo signals output by the ADC 1124 by delay times necessary for determining reception directionality, and the adder 1128 generates ultrasound data by summing the echo signals processed by the reception delayer 1126. In some exemplary embodiments, the receiver 1120 does not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may be grayscale ultrasound image obtained by scanning an object in an amplitude (A) mode, a B mode, and a motion (M) mode, and also may be a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 extracts B mode components from ultrasound data and processes the B mode components. An image generator 1220 may generate an ultrasound image indicating signal intensities as brightness based on the extracted B mode components 1212.

Similarly, a Doppler processor 1214 may extract Doppler components from ultrasound data, and the image generator 1220 may generate a Doppler image indicating a movement of an object as colors or waveforms based on the extracted Doppler components.

According to an exemplary embodiment, the image generator 1220 may generate a 3D ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. The generated ultrasound image may be stored in the memory 1500.

A display 1400 displays the generated ultrasound image. The display 1400 may display an ultrasound image and various pieces of information processed by the ultrasound apparatus 1000 on a screen image via a GUI. The ultrasound apparatus 1000 may include two or more displays 1400 according to exemplary embodiments. For example, the ultrasound apparatus 1000 may include a first display and a second display. The first display may be a main screen for displaying an ultrasound image, and the second display may be a control screen for displaying a plurality of control items.

The display 1400 may include the touch screen 1410. In this case, the display 1400 may function as the input device 1600.

The communication interface 1300 is connected to a network 30 by wire or wirelessly to communicate with an external device or a server 32. For example, the communication interface 1300 is connected to the network 30 by wire or wirelessly to exchange data with an external medical apparatus 34 or a portable terminal 36.

The communication interface 1300 may exchange data with a hospital server or another medical apparatus in a hospital, which is connected thereto via a PACS. Furthermore, the communication interface 1300 may perform data communication according to the DICOM standard.

The communication interface 1300 may transmit or receive data related to diagnosis of an object 10, e.g., an ultrasound image, ultrasound data, and Doppler data of the object 10, via the network 30 and may also transmit or receive medical images captured by another medical apparatus of another modality, e.g., a computed tomography (CT) apparatus, a magnetic resonance imaging (MRI) apparatus, or an X-ray apparatus. Furthermore, the communication interface 1300 may receive information about a diagnosis history or medical treatment schedule of a patient from a server 32 and utilizes the received information to diagnose the patient. Furthermore, the communication interface 1300 may perform data communication with a server or a medical apparatus in a hospital, and also may perform data communication with a portable terminal of a medical doctor or patient.

The communication interface 1300 may include one or more components for communication with external devices. For example, the communication interface 1300 may include a local area communicator 1310, a wired communicator 1320, and a mobile communicator 1330.

The local area communicator 1310 refers to a module for local area communication within a predetermined distance. Examples of local area communication techniques according to an exemplary embodiment may include, but are not limited to, wireless LAN, Wi-Fi, Bluetooth, ZigBee, WFD, UWB, IrDA, BLE, and NFC.

The wired communicator 1320 refers to a module for communication using electrical signals or optical signals. Examples of wired communication techniques according to an exemplary embodiment may include communication via a twisted pair cable, a coaxial cable, an optical fiber cable, and an Ethernet cable.

The mobile communicator 1330 transmits or receives wireless signals to or from at least one of a base station, an external terminal, and a server on a mobile communication network. The wireless signals may be voice call signals, video call signals, or various types of data for transmission and reception of text and/or multimedia messages.

The memory 1500 stores various data processed by the ultrasound apparatus 1000. For example, the memory 1500 may store medical data related to diagnosis of an object, such as ultrasound data and an ultrasound image that are input or output, and may also store algorithms or programs which are to be executed in the ultrasound apparatus 1000. Also, the memory 1500 may store a plurality of control items for adjusting parameters related to an ultrasound image, information of a user interface related to each of the control items, information of a preset gain value (e.g., TGC preset or preset LGC), and information of a gesture matched to a specific function.

The memory 1500 may be any of various storage medium media, e.g., a flash memory, a hard disk drive, EEPROM, etc. Furthermore, the ultrasound apparatus 1000 may utilize web storage medium or a cloud server that performs the storage medium function of the memory 1500 online.

The input device 1600 refers to a means via which a user inputs data for controlling the ultrasound apparatus 1000. The input device 1600 may include hardware components, such as a keypad, a mouse, a touch pad, a touch screen 1410, and a jog switch. However, exemplary embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc. According to an exemplary embodiment, the input device 1600 may include the control panel 200 that displays the control items.

The controller 1700 may control all operations of the ultrasound apparatus 1000. In other words, the controller 1700 may control operations among the probe 20, the ultrasound transceiver 1100, the image processor 1200, the communication interface 1400, the display 1300, the memory 1500, and the input device 1600.

All or some of the probe 20, the ultrasound transceiver 1100, the image processor 1200, the communication interface 1300, the display 1400, the memory 1500, the input device 1600, and the controller 1700 may be implemented as software modules. Also, at least one of the ultrasound transceiver 1100, the image processor 1200, and the communication interface 1300 may be included in the controller 1600; however, exemplary embodiments are not limited thereto.

The controller 1700 may control the touch screen 1410 such that the ultrasound image is updated according to modified TGC information. For example, the controller 1700 may update the ultrasound image by applying at least one adjusted TGC value to ultrasound echo signal data of the ultrasound image. Among a plurality of ultrasound image frames that respectively correspond to a plurality of TGC value sets, the controller 1700 may select a second ultrasound image frame that corresponds to a second TGC value set. Also, the controller 1700 may update the ultrasound image by displaying the second ultrasound image frame instead of a first ultrasound image frame that corresponds to a first TGC value set.

From a storage medium, the controller 1700 may read the ultrasound image and TGC information that is matched to the ultrasound image and stored in the storage medium. Also, the controller 1700 may match updated ultrasound image to modified TGC information and store the updated ultrasound image in the storage medium.

The methods according to exemplary embodiments may be implemented through program instructions that are executable via various computer devices and recorded in computer-readable recording media. The computer-readable recording media may include program instructions, data files, data structures, or a combination thereof. The program instructions may be specifically designed or known to those skilled in the art of computer software. Examples of the computer-readable recording media include magnetic media (e.g., hard disks, floppy disks, or magnetic tapes), optical media (e.g., CD-ROMs or DVDs), magneto-optical media (e.g., floptical disks), and hardware devices specifically designed to store and execute the program instructions (e.g., ROM or RAM). Examples of the program instructions include machine codes that are made by compilers, and computer-executable high level language codes that may be executed by using an interpreter.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A method of displaying ultrasound images, the method comprising:
   receiving an ultrasound image and receiving ultrasound echo signal data and time gain compensation (TGC) information that correspond to the ultrasound image, from an external device based on a user's input;
   displaying, on a screen, the ultrasound image and the TGC information matched to the displayed ultrasound image;
   receiving an input of modifying the TGC information via a user adjustment of at least one TGC value in the displayed TGC information that corresponds to a respective depth value in the ultrasound image, thereby obtaining modified TGC information;
   applying the modified TGC information to the ultrasound echo signal data, to obtain modified ultrasound echo signal data;
   displaying, on the screen, an updated ultrasound image obtained based on the modified ultrasound echo signal data; and
   transmitting the modified TGC information for controlling the external device to display the updated ultrasound image on a display of the external device based on the modified TGC information.

2. The method of claim 1, wherein the receiving the ultrasound image, the ultrasound echo signal data, and the TGC information further comprises receiving the ultrasound image, the ultrasound echo signal data, and the TGC information by an ultrasound apparatus, and
   the external device includes an external storage medium and is provided externally to the ultrasound apparatus.

3. The method of claim 1, wherein the ultrasound image is one of a plurality of ultrasound images, and the method further comprises:
   prior to the receiving the ultrasound image, the ultrasound echo signal data, and the TGC information, displaying a list of the plurality of ultrasound images stored in the external device; and
   receiving the user's input of selecting the ultrasound image from the displayed list of the plurality of ultrasound images.

4. The method of claim 1, wherein the displaying the TGC information further comprises displaying, on an area of the screen, a TGC line that indicates a first TGC value set corresponding to the TGC information,
   the receiving the input of modifying the TGC information further comprises receiving the input of modifying the first TGC value set to a second TGC value set via adjusting the TGC line, and
   the second TGC value set corresponds to the modified TGC information.

5. The method of claim 4, wherein the receiving the input of modifying the first TGC value set to the second TGC value set further comprises:
receiving an input of moving at least one adjustment button among adjustment buttons located at an intersection of the TGC line and a TGC slider bar displayed within the area of the screen, the at least one adjustment button corresponding to the at least one TGC value.

6. The method of claim 4, wherein the receiving the input of modifying the first TGC value set to the second TGC value set further comprises:
displaying a list of TGC preset values sets; and
receiving an input of selecting the second TGC value set from the displayed list.

7. The method of claim 6, wherein the displaying the list of the TGC preset values sets comprises:
displaying a text that indicates values of the TGC preset values sets.

8. The method of claim 6, wherein the displaying the list of the TGC preset values sets comprises displaying TGC images including corresponding TGC lines intersecting a TGC slider bar displayed within the area of the screen, and each of the displayed TGC images respectively represents the TGC preset values sets.

9. The method of claim 4, wherein the displaying the ultrasound image further comprises displaying a first ultrasound image frame obtained by applying the first TGC value set to the ultrasound echo signal data, and
the displaying the ultrasound image further comprises:
applying the second TGC value set to the ultrasound echo signal data, to obtain a second ultrasound image frame, and
displaying the second ultrasound image frame instead of the first ultrasound image frame, as the updated ultrasound image.

10. The method of claim 1, wherein the applying the modified TGC information further comprises:
applying the at least one TGC value, which has been adjusted, to the ultrasound echo signal data.

11. The method of claim 1, further comprising matching the updated ultrasound image to the modified TGC information and storing the updated ultrasound image together with the matched modified TGC information.

12. The method of claim 1, wherein the method is performed in a medical facility, and
wherein the external device is located in at least one from among a home of a patient and an ambulance transporting the patient.

13. An ultrasound apparatus comprising:
a communication interface configured to receive an ultrasound image and receive ultrasound echo signal data and time gain compensation (TGC) information that correspond to the ultrasound image, from an external device;
a touch screen configured to display the ultrasound image received from the external device, display the TGC information matched to the displayed ultrasound image, and receive an input of modifying the TGC information via a user adjustment input of adjusting at least one TGC value in the displayed TGC information that corresponds to a depth value in the ultrasound image; and
a controller configured to:
obtain modified TGC information based on the user adjustment input,
apply the modified TGC information to the ultrasound echo signal data, to obtain modified ultrasound echo signal data,
control the touch screen to display an updated ultrasound image obtained based on the modified ultrasound echo signal data, and
control the communication interface to transmit the modified TGC information for controlling the external device to display the updated ultrasound image on a display of the external device based on the modified TGC information.

14. The ultrasound apparatus of claim 13, wherein the touch screen is further configured to display, on an area of the touch screen, a TGC line that indicates a first TGC value set corresponding to the TGC information, and receive an input of modifying the first TGC value set to a second TGC value set via adjusting the TGC line, and
wherein the second TGC value set corresponds to the modified TGC information.

15. The ultrasound apparatus of claim 14, wherein the touch screen is further configured to display a list of TGC preset values sets, and receive an input of selecting the second TGC value set from the displayed list.

16. The ultrasound apparatus of claim 15, wherein the touch screen is further configured to display a text which represents values of the TGC preset values sets, or TGC images respectively including TGC lines intersecting a TGC slider bar displayed on the touch screen, each of the displayed TGC images respectively representing the TGC preset values sets.

17. The ultrasound apparatus of claim 14, wherein, in the displaying the ultrasound image, the touch screen is configured to display a first ultrasound image frame obtained by applying the first TGC value set to the ultrasound echo signal data, and
the controller is further configured to apply the second TGC value set to the ultrasound echo signal data, to obtain a second ultrasound image frame, and control the touch screen to display the second ultrasound image frame instead of the first ultrasound image frame, as the updated ultrasound image.

18. The ultrasound apparatus of claim 13, wherein the controller is further configured to update the ultrasound image by applying the at least one TGC value, which has been adjusted, to the ultrasound echo signal data.

19. The ultrasound apparatus of claim 13, wherein the controller is further configured to match the updated ultrasound image to the modified TGC information and store the updated ultrasound image together with the matched modified TGC information.

20. A method of displaying ultrasound images, the method comprising:
receiving an ultrasound image and receiving a first time gain compensation (TGC) value set and ultrasound echo signal data that correspond to the ultrasound image, from an external device;
displaying, on a first area of a screen, the ultrasound image matched to the first TGC value set;
displaying, on a second area of the screen, a gain setting window for adjusting first TGC values that respectively correspond to depth values of the ultrasound image;
receiving a second TGC value set via the gain setting window;
applying second TGC values included in the second TGC value set to the ultrasound echo signal data, to obtain modified ultrasound echo signal data;

displaying, on the first area of the screen, an updated ultrasound image obtained based on the modified ultrasound echo signal data; and transmitting the second TGC value set for controlling the external device to display the updated ultrasound image on a display of the external device based on the second TGC value set.

21. The method of claim 20, wherein the displaying the gain setting window comprises:
displaying buttons corresponding to TGC slider bars; and
initializing locations of the buttons on the TGC slider bars.

22. The method of claim 21, wherein the receiving the second TGC value set via the gain setting window comprises:
receiving an input of adjusting the locations of the buttons on the TGC slider bars to correspond to TGC values in the second TGC value set.

23. The method of claim 20, wherein the receiving the second TGC value set via the gain setting window comprises:
displaying a list of TGC preset values sets; and
receiving an input of selecting the second TGC value set from the displayed list.

24. The method of claim 20, further comprising:
matching the updated ultrasound image to the second TGC value set and storing the updated ultrasound image together with the second TGC value set.

25. An ultrasound apparatus comprising:
a communication interface configured to receive an ultrasound image and receive a first time gain compensation (TGC) value set and ultrasound echo signal data that correspond to the ultrasound image, from an external device;
a touch screen configured to display, on a first area, the ultrasound image matched to the first TGC value set, display, on a second area, a gain setting window for adjusting first TGC values that respectively correspond to depth values of the ultrasound image, and receive an input of values of a second TGC value set via the gain setting window; and
a controller configured to:
apply second TGC values included in the second TGC value set to the ultrasound echo signal data, to obtain modified ultrasound echo signal data,
display, on the first area of the touch screen, an updated ultrasound image obtained based on the modified ultrasound echo signal data, and
control the communication interface to transmit the second TGC value set for controlling the external device to display the updated ultrasound image on a display of the external device based on the second TGC value set.

26. A method of displaying medical images, the method comprising:
receiving an ultrasound image and receiving ultrasound echo signal data and first time gain compensation (TGC) data set values, the ultrasound echo signal data and the first TGC data set values corresponding to the ultrasound image, from an external device;
displaying, on a screen, the ultrasound image and the first TGC data set values matched to depth levels of the displayed ultrasound image;
receiving a user's input for modifying the first TGC data set values to second TGC data set values, by receiving the user's input of adjusting at least one TGC value corresponding to a respective depth value, in the displayed first TGC data set values;
adjusting brightness in the displayed ultrasound image at corresponding depth levels, by applying the second TGC data set values to the ultrasound echo signal data; and
transmitting the second TGC data set values for controlling the external device to display the ultrasound image in which the brightness is adjusted on a display of the external device based on the second TGC data set values.

27. The method of claim 26, wherein the displaying the first TGC data set values further comprises displaying, on an area of the screen separate from an area on which the ultrasound image is displayed, first TGC slider bars corresponding to the depth levels and a TGC line intersecting the first TGC slider bars at first locations indicating the first TGC data set values, and
the receiving the user's input for modifying the first TGC data set values further comprises receiving an input corresponding to touching and dragging the one of the first locations on the TGC line to a second location on a respective slider bar, in correspondence to the user's input.

28. The method of claim 27, wherein the receiving the input corresponding to the touching and dragging further comprises:
moving all of the first locations indicating the first TGC data set values to second locations on respective second TGC slider bars, in correspondence to the TGC line being touched and dragged on the one of the first locations; and
modifying the first TGC data set values to the second TGC data set values to respectively correspond to values of the second locations at which the TGC line intersects the second TGC slider bars, after being touched and dragged on the one of the first locations.

29. The method of claim 26, wherein the first TGC data set values and the second TGC data set values are included into a plurality of TGC data sets, and
the method further comprises:
generating ultrasound image frames by applying values of the plurality of TGC data sets to the ultrasound echo signal data, and
prestoring the ultrasound image frames in correspondence with the plurality of TGC data sets which have been respectively applied to generate the ultrasound image frames.

30. The method of claim 29, wherein the receiving the ultrasound image, the ultrasound echo signal data, and first TGC data set values further comprises retrieving a first ultrasound image frame, from the prestored ultrasound image frames, that corresponds to the first TGC data set values,
the displaying the ultrasound image and the first TGC data set values comprises displaying the first ultrasound image frame matched to the first TGC data set values, and
the adjusting the brightness further comprises:
retrieving a second ultrasound image frame, from the prestored ultrasound image frames, that corresponds to the second TGC data set values, and
displaying the second ultrasound image frame instead of the first ultrasound image frame, thereby displaying brightness values at the corresponding depth levels in the ultrasound image in correspondence with the second TGC data set values.

\* \* \* \* \*